US010757937B2

(12) United States Patent
Cutler et al.

(10) Patent No.: US 10,757,937 B2
(45) Date of Patent: Sep. 1, 2020

(54) SULFONAMIDES THAT ACTIVATE ABA RECEPTORS

(71) Applicant: The Regents of the University of California, Oakland, CA (US)

(72) Inventors: Sean R. Cutler, Riverside, CA (US); Aditya Vaidya, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 6 days.

(21) Appl. No.: 15/582,101

(22) Filed: Apr. 28, 2017

(65) Prior Publication Data

US 2017/0231224 A1 Aug. 17, 2017

Related U.S. Application Data

(63) Continuation of application No. PCT/US2015/057637, filed on Oct. 27, 2015.

(60) Provisional application No. 62/069,774, filed on Oct. 28, 2014.

(51) Int. Cl.
| | | |
|---|---|---|
| *A01N 41/06* | (2006.01) | |
| *C07C 311/51* | (2006.01) | |
| *A01N 43/42* | (2006.01) | |
| *A01N 43/32* | (2006.01) | |
| *A01N 43/10* | (2006.01) | |
| *A01N 43/40* | (2006.01) | |
| *A01N 47/24* | (2006.01) | |
| *A01N 53/00* | (2006.01) | |

(52) U.S. Cl.
CPC ............ *A01N 41/06* (2013.01); *A01N 43/10* (2013.01); *A01N 43/32* (2013.01); *A01N 43/40* (2013.01); *A01N 43/42* (2013.01); *A01N 47/24* (2013.01); *A01N 53/00* (2013.01); *C07C 311/51* (2013.01)

(58) Field of Classification Search
None
See application file for complete search history.

(56) References Cited

U.S. PATENT DOCUMENTS

| | | | | |
|---|---|---|---|---|
| 8,592,427 B2 * | 11/2013 | Blumberg | ............ | A61K 47/545 514/253.07 |
| 9,345,245 B2 | 5/2016 | Cutler et al. | | |
| 2010/0009852 A1 | 1/2010 | Rosinger et al. | | |
| 2013/0045952 A1 | 2/2013 | Xu et al. | | |

FOREIGN PATENT DOCUMENTS

| | | | | |
|---|---|---|---|---|
| WO | WO1995009151 | * | 4/1995 | |
| WO | WO-2010046423 A2 | * | 4/2010 | ............. A01N 47/36 |
| WO | WO-2011163594 A2 | * | 12/2011 | ........... A61K 47/545 |
| WO | 2013037955 A1 | | 3/2013 | |
| WO | 2016069637 A1 | | 5/2016 | |

OTHER PUBLICATIONS

Cao, Minjie; et. al. "An ABA-mimicking ligand that reduces water loss and promotes drought resistance in plants" Cell Research, 2013, v. 23, 1043-1054 (Year: 2013).*
Patani, G. A. et. al . "Bioisosterism: A rational approach in drug design" Chemical Reviews 1996, 96, 3147-3176 (Year: 1996).*
Yadegari et al., "Comparative effects of abscisic acid and two Sulfonamide compounds on tomato under drought conditions," Iranian Journal of Plant Physiology 3(3), Jan. 1, 2013, pp. 757-763, XP055238816.
PCT/US2015/057637, International Search Report and Written Opinion, dated Jan. 26, 2016, pp. 1-10.

* cited by examiner

*Primary Examiner* — Erin E Hirt
(74) *Attorney, Agent, or Firm* — KilpatrickTownsend & Stockton LLP

(57) ABSTRACT

The present invention provides methods and compositions comprising agonist compounds that activate ABA receptors. In one aspect, the invention provides an agricultural formulation useful for inducing ABA responses in plant vegetative tissues, reducing abiotic stress in plants, and inhibiting germination of plant seeds. The compounds are also useful for inducing expression of ABA-responsive genes in cells that express endogenous or heterologous ABA receptors.

19 Claims, No Drawings
Specification includes a Sequence Listing.

SULFONAMIDES THAT ACTIVATE ABA RECEPTORS

CROSS-REFERENCES TO RELATED APPLICATIONS

The present application is a U.S. continuation of International Application No. PCT/US2015/057637, filed Oct. 27, 2015, which claims the benefit of U.S. Provisional Patent Application No. 62/069,774, filed Oct. 28, 2014. These applications are incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No. IOS: 1258175 awarded by the National Science Foundation. The government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SEQ_081906-216010US-1047647_ST25.TXT, created on Apr. 26, 2017, 218,691 bytes, machine format IBM-PC, MS-Windows operating system, is hereby incorporated by reference in its entirety for all purposes.

FIELD OF THE INVENTION

The present invention is directed to compositions and methods comprising compounds that modulate the abscisic acid (ABA) signaling pathway and physiological processes influenced by this pathway. Various aspects and embodiments relate generally to novel sulfonamides that activate this pathway and to methods of preparing or using such compounds.

BACKGROUND OF THE INVENTION

Abscisic acid (ABA) is a plant hormone that regulates signal transduction associated with abiotic stress responses (Cutler et al., 2010, Abscisic Acid: Emergence of a Core Signaling Network. *Annual Review of Plant Biology* 61:651-679). ABA regulates numerous physiological processes and plays a major role in abiotic stress responses and tolerance to water deficit (i.e., drought). ABA biosynthesis is stimulated by decreases in soil water content, which lead to elevated hormone levels that in turn stimulate large-scale alterations in transcript abundance, guard cell closure, increased production of protective osmolytes, and numerous other physiological changes (Cutler et al., 2010).

A land-plant specific signaling pathway composed of receptors, phosphatases and kinases mediates ABA responses (Cutler et al., 2010). ABA elicits many of its cellular responses by binding to a soluble family of receptors called PYR/PYL proteins. PYR/PYL proteins belong to a large family of ligand-binding proteins named the START superfamily (Iyer et al., 2001; Ponting et al., 1999). These proteins contain a conserved three-dimensional architecture consisting of seven anti-parallel beta sheets that surround a central alpha helix to form a "helix-grip" motif. Together, these structural elements form a ligand-binding pocket for binding ABA or other agonists.

In the ABA response pathway, the phosphorylation status of three closely related ABA-regulated SnRK2 protein kinases is tied to environmental stress. When activated by phosphorylation on a critical activation loop near their ATP-binding site, these kinases phosphorylate downstream transcription factors, ion channels and most likely other proteins involved in ABA action (Weiner et al., 2010). Under ideal growth conditions the SnRK2s are continuously dephosphorylated and inactivated by a family of protein phosphatases (clade A PP2Cs), which results in nearly undetectable SnRK2 kinase activity in the absence of abiotic stress. When PP2C activity is inhibited by ABA-bound receptors, SnRK2s become highly active, probably because of their intrinsic ability to autoactivate by cis- and trans-autophosphorylation on their activation loops (Ng et al., 2011). Thus, ABA ultimately controls SnRK2 activity by receptor-mediated inhibition of PP2C activity.

The ABA signaling pathway has been exploited to improve plant stress response and associated yield traits via numerous approaches (Yang et al., 2010). The direct application of ABA to plants improves their water use efficiency (Raedmacher et al., 1987). Natural ABA can be used for improving drought tolerance in horticultural species (U.S. Pat. Publ. No. 2008/0227645) as well as several other uses. ABA analogs with improved resistance to metabolic degradation have been disclosed (U.S. Pat. Publ. No. 2008/0200339; U.S. Pat. No. 6,004,905; U.S. patent application Ser. No. 14/385,695), and these compounds have provided more persistent effects than ABA itself.

Because of their potential for improving crop yield (Notman et al., 2009), the discovery of ABA agonists has received increasing attention (Park et al., 2009; Melcher et al., 2010, Identification and mechanism of ABA receptor antagonism. *Nature Structural & Molecular Biology* 17(9): 1102-1110). The first synthetic ABA agonist identified was the naphthalene sulfonamide pyrabactin (Park et al., 2009), which efficiently activates ABA signaling in seeds but has limited activity in vegetative tissues, where the most critical aspects of abiotic stress tolerance occur. Sulfonamides highly similar to pyrabactin have been disclosed as ABA agonists (see U.S. Pat. Publ. No. 2013/0045952) and abiotic stress modulating compounds (see U.S. Pat. Publ. No. 2011/0230350). Non-sulfonamide ABA agonists have also been described (see U.S. Pat. Publ. Nos. 2013/0045952 and 2011/0271408).

In *Arabidopsis*, the sulfonamide agonist quinabactin preferentially activates the three dimeric ABA receptors PYR1, PYL1 and PYL2. Its activity on these receptors is sufficient to induce drought tolerance, guard-cell closure, and ABA-mediated gene expression. Moreover, it has activity in crop species including soybean and maize. The activity of quinabactin in *Arabidopsis* is abolished in a mutant pyr1; pyl1;pyl2,pyl4 strain that removes the three ABA receptors with which quinabactin has highest potency. The preferential activity of quinabactin on the dimeric receptors combined with the necessity of these receptors for quinabactin action suggests that activating the dimeric ABA receptors is sufficient to elicit the major effects associated with ABA action.

Although quinabactin points to the dimeric receptors as targets for chemical control of ABA action and drought tolerance, genetic data indicate that the monomeric ABA receptors also play roles in ABA signaling. For example, a pyl8 loss-of-function mutants strain shows reduced root-growth inhibition by ABA (Antoni et al., 2012). In addition, the sequential removal of monomeric ABA receptors from a strain lacking the three dimeric receptors increases ABA insensitivity in proportion to the number of monomeric receptors removed (Gonzalez-Guzman et al., 2012). This argues that the ABA receptors may play additive roles in ABA signaling; however, the relative importance of each receptor class (dimeric versus monomeric) to ABA signaling is not clear, since mutant strains that selectively remove multiple monomeric receptors have not yet been described. Nonetheless, the monomeric receptors make contributions to ABA sensitivity and, as such, compounds that activate monomeric receptors may be useful for controlling drought tolerance, either on their own or in combination with compounds that activate the dimeric receptors such as quinabactin.

The present invention provides an N-acylsulfonamide scaffold that affords access to potent agonists of diverse monomeric ABA receptors. Compounds that preferentially activate PYL5 or PYL9 are disclosed as well as compounds that activate multiple monomeric receptors with relatively lower selectivity. Members of this compound class are bioactive in vivo; they are capable of inhibiting seed germination and can close guard cells in planta, a key physiological response necessary for chemical control of drought tolerance. The ability of this compound class to induce ABA responses in a plant demonstrates that monomeric receptors can be targeted for chemical control of ABA responses.

BRIEF SUMMARY OF THE INVENTION

The present invention provides for methods and compositions comprising small molecule ABA agonists, i.e., compounds that activate PYR/PYL proteins.

In one aspect, the present invention provides a method of increasing abiotic stress tolerance in a plant, the method comprising contacting a plant with an effective amount of a sulfonamide agonist compound to increase abiotic stress tolerance in the plant, thereby increasing abiotic stress tolerance, wherein the sulfonamide agonist compound is of Formula

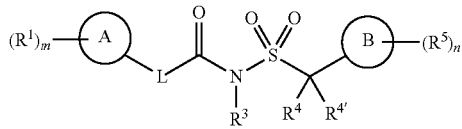

I wherein A is selected from the group consisting of alkyl, aryl, arylalkyl, heteroaryl, heteroarylalkyl, heterocyclyl, and cycloalkyl;

each $R^1$ is a substituent independently selected from the group including alkyl, alkenyl, alkynyl, cycloalkyl, heterocyclyl, aryl, heteroaryl, halo, fluoroalkyl, hydroxyl, hydroxyalkyl, alkoxy, fluoroalkoxy, alkoxyalkyl, amino, aminoalkyl, alkylthio, alkylthioalkyl, cyano, carboxyl, carboxyalkyl, alkoxycarbonyl, alkoxycarbonylalkyl, amido, and amidoalkyl; wherein the $R^1$ cycloalkyl, heterocyclyl, aryl, or heteroaryl is additionally substituted with from 0 to 3 $R^6$; or alternatively, two $R^1$ substituents join to form an additional $R^1$ ring, wherein the additional $R^1$ ring is selected from the group including aryl, heteroaryl, cycloalkyl, and heterocyclyl; and wherein the additional $R^1$ ring is additionally substituted with from 0 to 3 $R^6$; or alternatively, an $R^1$ and a $R^2$ substituent join to form an $R^{1,2}$ ring, wherein the $R^{1,2}$ ring is selected from the group including cycloalkyl and heterocyclyl; and wherein the $R^{1,2}$ ring is additionally substituted with from 0 to 3 $R^6$;

m is an integer selected from 0 to 5; wherein if A is not aryl or if at least two $R^1$ are not halo, m is an integer selected from 0 to 3;

L is a bond, —C($R^2$)($R^{2'}$)—, —O—, or —$NR^6$—; wherein if L is a bond, A is not alkyl; $R^2$ and $R^{2'}$ are each a substituent independently selected from the group including hydrogen, alkyl, fluoroalkyl, cycloalkyl, heterocycyl, heteroaryl, and aryl; wherein the cycloalkyl, heterocycyl, heteroaryl, and aryl is additionally substituted with from 0 to 3 $R^6$; or alternatively, an $R^2$ and an $R^{2'}$ join to form a geminal $R^2$ ring, wherein the geminal $R^2$ ring is selected from the group including cycloalkyl, cycloalkenyl, and heterocyclyl; and wherein the geminal $R^2$ ring is additionally substituted with from 0 to 4 $R^6$; or alternatively, the $R^2$ is joined into the $R^{1,2}$ ring;

$R^3$ is a substituent selected from the group including hydrogen, alkyl, and fluoroalkyl; and $R^4$ and $R^{4'}$ are each a substituent independently selected from the group including hydrogen, alkyl, chloro, fluoro, and fluoroalkyl; or alternatively, an $R^4$ and an $R^{4'}$ join to form a geminal $R^4$ ring, wherein the geminal $R^4$ ring is selected from the group including cycloalkyl, cycloalkenyl, and heterocyclyl; and wherein the geminal $R^4$ ring is additionally substituted with from 0 to 4 $R^6$;

B is selected from the group including aryl, heteroaryl, heterocyclyl, and cycloalkyl;

each $R^5$ is a substituent independently selected from the group including alkyl, alkenyl, alkynyl, cycloalkyl, heterocyclyl, aryl, heteroaryl, halo, fluoroalkyl, nitro, hydroxyl, hydroxyalkyl, alkoxy, alkoxyalkyl, amino, aminoalkyl, alkylthio, alkylthioalkyl, cyano, carboxyl, carboxyalkyl, alkoxycarbonyl, alkoxycarbonylalkyl, amido, and amidoalkyl; or alternatively, two $R^5$ join to form an additional $R^5$ ring, wherein the additional $R^5$ ring is selected from the group including aryl, heteroaryl, cycloalkyl, and heterocyclyl; and wherein the additional $R^5$ ring is additionally substituted with from 0 to 5 $R^6$;

n is an integer selected from 0 to 5; wherein if B is not aryl or if at least two $R^5$ are not halo, m is an integer selected from 0 to 3; and each $R^6$ is a substituent independently selected from the group including alkyl, aryl, halo, fluoroalkyl, hydroxyl, alkoxy, amino, cyano, carboxyl, alkoxycarbonyl, and amido.

In one aspect, the present invention provides a method of increasing abiotic stress tolerance in a plant, the method comprising a step of contacting a plant with an effective amount of a compound to increase abiotic stress tolerance in the plant, thereby increasing abiotic stress tolerance; where the compound is of Formula IB:

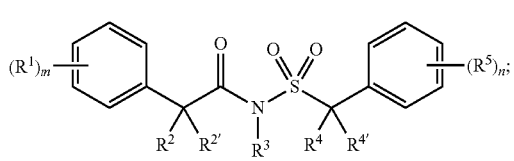

IB where each $R^1$ is a substituent independently selected from alkyl, alkenyl, alkynyl, cycloalkyl, heterocyclyl, aryl, heteroaryl, halo, fluoroalkyl, fluoroalkoxy, hydroxyl, hydroxyalkyl, alkoxy, alkoxyalkyl, amino, aminoalkyl, alkylthio, alkylthioalkyl, cyano, carboxyl, carboxyalkyl, alkoxycarbonyl, alkoxycarbonylalkyl, amido, or amidoalkyl; or, alternatively, two $R^1$ substituents join to form an additional $R^1$ ring, where the additional $R^1$ ring is selected from aryl, heteroaryl, cycloalkyl, or heterocyclyl; and where the additional $R^1$ ring is additionally substituted with from 0 to 3 $R^6$; or an $R^1$ and a $R^2$ substituent join to form an $R^{1,2}$ ring, where the $R^{1,2}$ ring is selected from cycloalkyl or heterocyclyl; and where the $R^{1,2}$ ring is additionally substituted with from 0 to 3 $R^6$;

m is an integer selected from 0 to 3;

$R^2$ and $R^{2'}$ are each a substituent independently selected from the group hydrogen, alkyl, or fluoroalkyl; or, alternatively, an $R^2$ and an $R^{2'}$ join to form a geminal $R^2$ ring, where the geminal $R^2$ ring is selected from the group cycloalkyl, cycloalkenyl, or heterocyclyl; and where the geminal $R^2$ ring is additionally substituted with from 0 to 3 $R^6$; or the $R^2$ is joined into the $R^{1,2}$ ring;

$R^3$ is a substituent selected from hydrogen, alkyl, or fluoroalkyl;

$R^4$ and $R^{4'}$ are each a substituent independently selected from hydrogen, alkyl, chloro, fluoro, or fluoroalkyl;

each $R^5$ is a substituent independently selected from alkyl, alkenyl, alkynyl, cycloalkyl, heterocyclyl, aryl, heteroaryl, halo, fluoroalkyl, nitro, hydroxyl, hydroxyalkyl, alkoxy, alkoxyalkyl, amino, aminoalkyl, alkylthio, alkylthioalkyl, cyano, carboxyl, carboxyalkyl, alkoxycarbonyl, alkoxycarbonylalkyl, amido, or amidoalkyl; or, alternatively, two $R^5$ join to form an additional $R^5$ ring, wherein the additional $R^5$ ring is selected from aryl, heteroaryl, cycloalkyl, or heterocyclyl; and wherein the additional $R^5$ ring is additionally substituted with from 0 to 3 $R^6$;

n is an integer selected from 0 to 3; and each $R^6$ is a substituent independently selected from the group alkyl, aryl, halo, fluoroalkyl, hydroxyl, alkoxy, amino, cyano, carboxyl, alkoxycarbonyl, or amido.

In one aspect, the present invention provides a method of inhibiting seed germination in a plant, the method comprising contacting a seed with a sufficient amount of the compound of Formula I, IB, II, III, IIIB, or IV as set forth herein, thereby inhibiting germination. In some embodiments, the method comprises contacting a seed with a sufficient amount of a formulation comprising a compound of Formula I, IB, II, III, IIIB, or IV.

In one aspect, the present invention provides a method of reducing transpiration in a plant, the method comprising contacting a plant with a sufficient amount of the compound of compound of Formula I, IB, II, III, IIIB, or IV as set forth herein, thereby reducing transpiration. In some embodiments, the method comprises contacting a plant with a sufficient amount of a formulation comprising a compound of Formula I, IB, II, III, IIIB, or IV as set forth herein.

In one aspect, the present invention provides a method of activating a PYR/PYL protein, the method comprising contacting the PYR/PYL protein with the compound of Formula I, IB, II, III, IIIB, or IV as set forth herein. In some embodiments, the PYR/PYL protein is selectively activated. In some embodiments, the method comprises contacting a protein with a sufficient amount of a formulation comprising a compound of Formula I, IB, II, III, IIIB, or IV as set forth herein.

In some embodiments, the PYR/PYL protein is expressed by a cell. In a further embodiment, the cell is a plant cell.

In some embodiments, the PYR/PYL protein is PYL-5. In some alternative embodiments, the PRY/PYL protein is PYL-8. In some alternative embodiments, the PYR/PYL protein is PYL-9.

In one aspect, the invention presents a formulation as set forth herein that further comprises a second active compound. In some embodiments, the invention presents a method as set forth herein that further comprises using a second active compound.

In some embodiments, the second active compound is a PYR/PYL receptor agonist. In some embodiments, the second active compound is a PYR/PYL receptor partial agonist. In some embodiments, the second active compound is a PYR/PYL receptor partial agonist.

In some embodiments, the second active compound is selected from the group quinabactin, racemic ABA, R-ABA, or S-ABA. In some embodiments, the second active compound is selected from the group benoxacor, benzothiadiazole, dichlorobenil, fludioxonil, or mandipropamid, In one aspect, the present invention provides a compound as set forth in one or more of the other aspects presented herein and their embodiments.

In one aspect, the present invention provides an agricultural formulation consisting of, consisting essentially of, or comprising a compound as set forth herein. In some embodiments, the agricultural formulation includes an agriculturally acceptable adjuvant.

In some embodiments, the formulation further comprises at least one of a fungicide, an herbicide, a pesticide, a nematicide, an insecticide, a plant activator, a synergist, an herbicide safener, a plant growth regulator, an insect repellant, an acaricide, a molluscicide, or a fertilizer.

In some embodiments, the formulation further comprises a surfactant.

In some embodiments, the formulation further comprises a carrier.

In one aspect, the present invention provides a method of increasing abiotic stress tolerance in a plant, the method comprising contacting a plant with a sufficient amount of a compound or formulation to increase abiotic stress tolerance in the plant compared to not contacting the plant with the compound or formulation, wherein the compound or formulation is as set forth herein.

In some embodiments, the plant is a monocot. In some alternative embodiments, the plant is a dicot.

In some embodiments, the abiotic stress tolerance comprises drought tolerance. In some embodiments, the contacting step comprises delivering the formulation to the plant by aircraft or irrigation.

In one aspect, the present invention provides a method of inhibiting seed germination in a plant, the method comprising contacting a seed with a sufficient amount of the compound or formulation to inhibit germination, wherein the compound or formulation is as set forth herein.

In one aspect, the present invention provides a plant in contact with a compound or formulation as set forth herein. In some embodiments, the plant is a monocot. In some alternative embodiments, the plant is a dicot.

In some embodiments, a seed, flower, leaf, fruit, processed food, or food ingredient from a plant as described herein is provided. In some embodiments, the plant is a seed.

In one aspect, the present invention provides a method of activating a PYR/PYL protein, the method comprising contacting the PYR/PYL protein with a compound or formulation as set forth herein.

In some embodiments, the PYR/PYL protein is expressed by a cell. In some embodiments, the cell is a plant cell. In some alternative embodiments, the cell is a plant, animal, mammalian, or fungal cell.

Further aspects, objects, and advantages of the invention will become apparent upon consideration of the detailed description and figures that follow.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of contradictory disclosure, the present specification, including these definitions, will control.

The terms "a," "an," or "the" as used herein not only include aspects with one member, but also include aspects with more than one member. For example, an embodiment of a method that comprises contacting a plant with an effective amount of a compound as set forth in claim 1 would include an aspect in which the method comprises using two or more compounds as set forth in claim 1.

As used herein, the terms "abiotic stress," "stress," or "stress condition" refer to the exposure of a plant, plant cell, or the like, to a non-living ("abiotic") physical or chemical agent that has an adverse effect on metabolism, growth, development, propagation, or survival of the plant (collectively, "growth"). A stress can be imposed on a plant due, for example, to an environmental factor such as water (e.g., flooding, drought, or dehydration), anaerobic conditions (e.g., a lower level of oxygen or high level of $CO_2$), abnormal osmotic conditions, salinity, or temperature (e.g., hot/heat, cold, freezing, or frost), a deficiency of nutrients or exposure to pollutants, or by a hormone, second messenger, or other molecule.

Anaerobic stress, for example, is due to a reduction in oxygen levels (hypoxia or anoxia) sufficient to produce a stress response. A flooding stress can be due to prolonged or transient immersion of a plant, plant part, tissue, or isolated cell in a liquid medium such as occurs during monsoon, wet season, flash flooding, or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Salinity-induced stress (salt-stress) can be associated with or induced by a perturbation in the osmotic potential of the intracellular or extracellular environment of a cell. As used herein, the term "abiotic stress tolerance" or "stress tolerance" refers to a plant's increased resistance or tolerance to abiotic stress as compared to plants under normal conditions and the ability to perform in a relatively superior manner when under abiotic stress conditions. As used herein, the terms "drought resistance" and "drought tolerance" are used to refer to a plant's increased resistance or tolerance to stress induced by a reduction in water availability, as compared to normal circumstances, and the ability of the plant to function and survive in lower-water environments, and perform in a relatively superior manner.

The term "about" as used herein to modify a numerical value indicates a defined range around that value. If "X" were the value, "about X" would indicate a value from 0.9X to 1.1X, and preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When the quantity "X" only allows whole-integer values (e.g., "X carbons") and X is at most 15, "about X" indicates from (X−1) to (X+1). In this case, "about X" as used herein specifically indicates at least the values X, X−1, and X+1. If X is at least 16, the values of 0.90X and 1.10X are rounded to the nearest whole-integer values to define the boundaries of the range.

When the modifier "about" is applied to describe the beginning of a numerical range, it applies to both ends of the range. Thus, "from about 50 to 100" is equivalent to "from about 50 to about 100." When "about" is applied to describe the first value of a set of values, it applies to all values in that set. Thus, "about 680, 700, or 750" is equivalent to "about 680, about 700, or about 750." However, when the modifier "about" is applied to describe only the end of the range or only a later value in the set of values, it applies only to that value or that end of the range. Thus, the range "about 3 to 6" is the same as "about 3 to about 6," but the range "3 to about 6" is not.

The term "activity assay" refers to any assay that measures or detects the activity of a PYR/PYL receptor polypeptide. An exemplary assay to measure PYR/PYL receptor activity is a yeast two-hybrid assay that detects binding of a PYR/PYL polypeptide to a type 2 protein phosphatase (PP2C) polypeptide, as described in the Examples.

"Agonists" are agents that, e.g., induce or activate the expression of a described target protein or bind to, stimulate, increase, open, activate, facilitate, enhance activation, sensitize or up-regulate the activity of one or more plant PYR/PYL proteins (or encoding polynucleotide). As used herein, "agonist" generally includes partial agonists, full agonists, and superagonists. Agonists can include naturally occurring and synthetic molecules. Assays for determining whether an agonist "agonizes" or "does not agonize" a PYR/PYL protein include, e.g., contacting putative agonists to purified PYR/PYL protein(s) and then determining the functional effects on the PYR/PYL protein activity, as described herein, or contacting putative agonists to cells expressing PYR/PYL protein(s) and then determining the functional effects on the described target protein activity, as described herein. One of skill in the art will be able to determine whether an assay is suitable for determining whether an agonist agonizes or does not agonize a PYR/PYL protein. Samples or assays comprising PYR/PYL proteins and a PP2C target enzyme are treated with a putative agonist and are compared to control samples without the agonist to examine the extent of effect on PP2C activity. Control samples (untreated with agonists) are assigned a relative activity value of 100%. The level of activity in the presence of saturating ABA (typically 5 to 10% PP2C activity) indicates the effect expected of a full agonist; super agonists are those that can elicit greater PP2C inihibition than ABA at saturating concentrations. Partial agonists inihibit PP2C activity less than ABA when compared at saturating concentrations. Agonism of the PYR/PYL protein is achieved when the activity value relative to the control is 80%, optionally 50%, optionally 40, 30%, 20%, 10%, or even lower (i.e., from the inhibition produced by PP2C agonism).

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

A "comparison window", as used herein, includes reference to a segment of any one of the number of contiguous positions selected from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. *Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 60% sequence identity with a reference sequence. Alternatively, percent identity can be any integer from 60% to 100%. Some embodiments include at least: 60%, 65%, 70%, 75%, 80%, 85%, 90%, 91%, 92%, 93%, 94% 95%, 96%, 97%, 98%, or 99%, compared to a reference sequence using the programs described herein, such as BLAST using standard parameters, e.g., as described below. Embodiments of the present invention provide for polypeptides, and nucleic acids encoding polypeptides, that are substantially identical to any of SEQ ID NO:1-119.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A polypeptide sequence is "heterologous" to an organism or a second polypeptide sequence if it originates from a foreign species, or, if from the same species, is modified from its original form.

As used herein, the term "drought-resistance" or "drought-tolerance," including any of their variations, refers to the ability of a plant to recover from periods of drought stress (i.e., little or no water for a period of days). Typically, the drought stress will be at least 5 days, and it can be as long as, for example, 18 to 20 days or more (e.g., at least 6, 7, 8, 9, 10, 11, 12, 13, 14, 15, 16, 17, 18, 19, 20 days), depending on, for example, the plant species.

The term "plant" includes whole plants, shoot vegetative organs or structures (e.g., leaves, stems and tubers), roots, flowers and floral organs (e.g., bracts, sepals, petals, stamens, carpels, anthers), ovules (including egg and central cells), seeds (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the methods of the invention includes angiosperms (monocotyledonous and dicotyledonous plants), gymnosperms, ferns, bryophytes, and multicellular and unicellular algae. It includes plants of a variety of ploidy levels, including aneuploid, polyploid, diploid, haploid, and hemizygous.

The term "PYR/PYL receptor polypeptide" refers to a protein characterized in part by the presence of one or more or all of a polyketide cyclase domain 2 (PF10604), a polyketide cyclase domain 1 (PF03364), and a Bet V I domain (PF03364), which in wild-type form mediates abscisic acid (ABA) and ABA analog signaling. A wide variety of PYR/PYL receptor polypeptide sequences are known in the art. In some embodiments, a PYR/PYL receptor polypeptide comprises a polypeptide that is substantially identical to any one of SEQ ID NOs:1-119. See, e.g., Int'l. Pat. Publ. No. WO 2011/139798; U.S. Pat. Publ. No. 2011/0271408.

As used herein, the term "transgenic" describes a non-naturally occurring plant that contains a genome modified by man, wherein the plant includes in its genome an exogenous nucleic acid molecule, which can be derived from the same or a different plant species. The exogenous nucleic acid molecule can be a gene regulatory element such as a promoter, enhancer, or other regulatory element, or can contain a coding sequence, which can be linked to a heterologous gene regulatory element. Transgenic plants that arise from sexual cross or by selfing are descendants of such a plant and are also considered "transgenic."

"Acyl" as used herein includes an alkanoyl, aroyl, heterocycloyl, or heteroaroyl group as defined herein. Representative acyl groups include acetyl, benzoyl, nicotinoyl, and the like.

"Alkanoyl" as used herein includes an alkyl-C(O)— group wherein the alkyl group is as defined herein. Representative alkanoyl groups include acetyl, ethanoyl, and the like.

"Alkenyl" as used herein includes a straight or branched aliphatic hydrocarbon group of 2 to about 15 carbon atoms that contains at least one carbon-carbon double bond (i.e., an alkene). In some embodiments, an alkenyl group has 2 to about 12 carbon atoms. In other embodiments, alkenyl groups contain 2 to about 6 carbon atoms. "Lower alkenyl" as used herein includes alkenyl of 2 to about 6 carbon atoms. Representative alkenyl groups include vinyl, allyl, methallyl, n-butenyl, 2-butenyl, 3-methylbutenyl, n-pentenyl, heptenyl, octenyl, decenyl, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" as used herein includes an alkyl-O— alkylene-group wherein alkyl and alkylene are as defined herein. Representative alkoxyalkyl include methoxymethyl, ethoxymethyl, 2-methoxyethyl, and the like.

"Alkoxycarbonyl" as used herein includes an alkyl or arylalkyl ester group; e.g., an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" as used herein includes an alkyl-O—CO-alkylene-group wherein alkyl and alkylene are as defined herein. Representative alkoxycarbonylalkyl include methoxycarbonylmethyl, ethoxycarbonylmethyl, methoxycarbonylethyl, and the like.

"Alkyl" as used herein includes an aliphatic hydrocarbon group, which may be straight or branched-chain, having 1 to about 20 carbon atoms in the chain. In some aspects, alkyl groups have 1 to about 12, 1 to 10, 1 to 8, or 1 to 6 carbon atoms in the chain. "Branched-chain" as used herein includes groups in which that one or more lower alkyl groups (such as methyl, ethyl or propyl) are attached to a linear alkyl chain. "Lower alkyl" as used herein includes 1 to about 6 carbon atoms, which may be straight or branched.

Representative alkyl groups include methyl, ethyl, n-propyl, isopropyl, n-butyl, t-butyl, n-pentyl, and 3-pentyl.

"Alkylene" as used herein includes a straight or branched bivalent hydrocarbon chain of 1 to about 6 carbon atoms in the group. In some further aspects, alkylene groups have 1 to about 4 carbon atoms. Representative alkylene groups include methylene, ethylene, and the like.

"Alkylthio" as used herein includes an alkyl-S-group wherein the alkyl group is as defined herein. In some aspects, an alkylthio groups is one wherein the alkyl group is lower alkyl. Representative alkylthio groups include methylthio, ethylthio, isopropylthio, heptylthio, and the like.

"Alkylthioalkyl" as used herein includes an alkylthio-alkylene-group wherein alkylthio and alkylene are defined herein. Representative alkylthioalkyl groups include methylthiomethyl, ethylthiopropyl, isopropylthioethyl, and the like.

"Alkynyl" as used herein includes a straight or branched aliphatic hydrocarbon group of 2 to about 15 carbon atoms that contains at least one carbon-carbon triple bond. In some aspects, an alkynyl group has 2 to about 12 carbon atoms. In some other aspect, an alkynyl group has 2 to about 6 carbon atoms. "Lower alkynyl" as used herein includes an alkynyl group of 2 to about 6 carbon atoms. Representative alkynyl groups include propynyl, 2-butynyl, 3-methylbutynyl, n-pentynyl, heptynyl, and the like.

"Amido" as used herein includes a group of formula $Y_1Y_2N—C(O)—$ wherein $Y_1$ and $Y_2$ are independently hydrogen, alkyl, or alkenyl; or $Y_1$ and $Y_2$, together with the nitrogen through which $Y_1$ and $Y_2$ are linked, join to form a 4- to 7-membered azaheterocyclyl group (e.g., piperidinyl). Representative amido groups include primary amido ($H_2N—C(O)—$), methylamido, dimethylamido, diethylamido, and the like. In some aspects, "amido" is an —C(O)NRR' group where R and R' are members independently selected from H or alkyl. In some aspects of the —C(O)NRR' group, at least one of R and R' is H.

"Amidoalkyl" as used herein includes an amido-alkylene-group wherein amido and alkylene are as defined herein. Representative amidoalkyl groups include amidomethyl, amidoethyl, dimethylamidomethyl, and the like.

"Amino" as used herein includes a group of formula $Y_1Y_2N—$ wherein $Y_1$ is hydrogen, acyl, aryl, alkyl, or arylalkyl, and wherein $Y_2$ is hydrogen, alkyl, or arylalkyl; or $Y_1$ and $Y_2$, together with the nitrogen through which $Y_1$ and $Y_2$ are linked, join to form a 4- to 7-membered azaheterocyclyl group (e.g., piperidinyl). In some aspects, amino is is an —NRR' group where R and R' are members independently selected from H or alkyl. In some aspects, at least one of R and R' is H. In some aspects, when $Y_1$ and $Y_2$ are independently hydrogen or alkyl, an additional substituent can be added to the nitrogen, making a quaternary ammonium ion. Representative amino groups include primary amino ($H_2N—$), methylamino, dimethylamino, diethylamino, tritylamino, and the like.

"Aminoalkyl" as used herein includes an amino-alkylene-group wherein amino and alkylene are defined herein. Representative aminoalkyl groups include aminomethyl, aminoethyl, dimethylaminomethyl, and the like.

"Aroyl" as used herein includes an aryl-CO— group wherein aryl is defined herein. Representative aroyl include benzoyl, naphth-1-oyl and naphth-2-oyl.

"Aryl" as used herein includes an aromatic monocyclic or multicyclic ring system of 6 to about 14 carbon atoms, or in some aspects, of 6 to about 10 carbon atoms. Aryl groups do not include aromatic ring heteroatoms (cf. heteroaryl groups). Representative aryl groups include phenyl and naphthyl.

"Arylalkyl" as used herein includes an alkyl group that is substituted by an aromatic monocyclic or multicyclic ring system of 6 to about 14 carbon atoms, or in some aspects, of 6 to about 10 carbon atoms. In some aspects, arylalkyl groups do not include aromatic ring heteroatoms in the aromatic ring system (cf. aryl and heteroaryl groups). Representative arylalkyl groups include benzyl, 4-cyanobenzyl, and the like.

"Aromatic ring" as used herein includes 5-12 membered $sp^2$-hybridized monocyclic or fused polycyclic moieties that may include from zero to four heteroatoms selected from oxygen, sulfur, selenium, or nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, and the like. In some aspects, an aromatic ring group can be substituted at one or more positions with up to five groups (but more frequently 1, 2, or 3) selected from halo, alkyl, alkoxy, alkoxycarbonyl, haloalkyl, cyano, sulfonato, amino sulfonyl, aryl, sulfonyl, aminocarbonyl, carboxy, acylamino, alkyl sulfonyl, amino, or the like.

"Carboxy" and "carboxyl" as used interchangeably herein include a HOC(O)— group (i.e., a carboxylic acid) or a salt thereof.

"Carboxyalkyl" as used herein includes a carboxyl-alkylene-group wherein carboxyl and alkylene are as defined herein. Representative carboxyalkyl groups include carboxymethyl (i.e., —$CH_2CO_2H$) and the like.

The term "comprising" or "comprises" as used herein is used non-exclusively. For example, a composition comprising A must include A, but could also include other components (e.g., A and B; A, B, and C; A, B, D, and E; and the like). A composition or method comprising certain claim elements presents an aspect that consists of those claim elements and an aspect that consists essentially of those claim elements. For example, the description of a method comprising the step A is intended to present (and provide support for) a method consisting of the step A and a method consisting essentially of the step A.

"Cycloalkyl" as used herein includes a non-aromatic mono- or multicyclic ring system of 3 to about 10 carbon atoms. In some aspects, the ring system is about 5 to about 10 carbon atoms. In some further aspects, a cycloalkyl ring contains a ring sytem of 5 or 6 ring carbon atoms. Representative monocyclic cycloalkyl groups include cyclopentyl, cyclohexyl, cycloheptyl, and the like. Representative multicyclic cycloalkyl groups include 1-decalin, norbornyl, adamantyl, and the like. In some aspects, cycloalkyl includes a spirocyclic ring (i.e., spirocycloalkyl).

"Cycloalkylalkyl" as used herein includes a cycloalkyl-alkylene-group wherein cycloalkyl and alkylene are as defined herein. Representative cycloalkylalkyl groups include cyclohexylmethyl, cyclopropylmethyl, and the like.

"Cycloalkenyl" as used herein includes a non-aromatic mono- or multicyclic ring system of 3 to about 10 carbon atoms that includes at least one $sp^2$-hybridized carbon and at least one $sp^3$-hybridized carbon (e.g., a non-aromatic ring incorporating an endocyclic or exocyclic olefin). In some aspects, the ring system is 5 to about 10 carbon atoms. In some further aspects, a cycloalkenyl ring contains a ring system of 5 or 6 ring carbon atoms.

Representative monocyclic cycloalkyl groups include cyclopent-3-enyl, cyclohexen-2-yl, and the like. Representative multicyclic cycloalkenyl include norbornenyl, 1,2,3,4-tetrahydronaphthalen-2-yl, and the like. In some aspects, cycloalkyl includes a spirocyclic ring (i.e., spirocycloalkenyl).

The term "effective amount" or "effective dose" as used herein includes an amount sufficient to achieve the desired result and accordingly will depend on the ingredient and its desired result. Nonetheless, once the desired effect is identified, determining the effective amount is generally within the skill of a person skilled in the art.

"Fluoroalkoxy" as used herein includes a fluoroalkyl-O— group wherein the fluoroalkyl group is as defined herein. Representative fluoroalkoxy groups include trifluoromethoxy, 2,2,2-trifluoroethoxy, perfluoroethoxy, and the like.

"Geminal" substituents as used herein include two or more substituents that are directly attached to the same atom. An example is 3,3-dimethyl substitution on a cyclohexyl ring or the ring junction of a spirocyclohexyl ring. If a "geminal" ring group (e.g., an $R^2$ geminal ring) sets forth possible rings (e.g., cycloalkyl, cycloalkenyl, and heterocyclyl for a geminal ring), this is intended to refer to a spirocyclic ring of the type indicated.

"Halo" or "halogen" as used herein includes fluoro, chloro, bromo, or iodo.

"Haloalkyl" as used herein includes an alkyl group wherein the alkyl group includes one or more halo-substituents. For example, a "fluoroalkyl" group would be an alkyl group that includes one or more fluoro substituents.

"Heteroaroyl" as used herein includes a heteroaryl-C(O)— group wherein heteroaryl is as defined herein. Representative heteroaroyl groups include thiophenoyl, nicotinoyl, pyrrol-2-ylcarbonyl, pyridinoyl, and the like.

"Heterocycloyl" as used herein includes a heterocyclyl-C(O)— group wherein heterocyclyl is as defined herein. Representative heterocycloyl groups include N-methyl prolinoyl, tetrahydrofuranoyl, and the like.

"Heterocyclyl" as used herein includes a non-aromatic, saturated or partially saturated, monocyclic or multicyclic ring system of 3 to about 10 ring atoms. In some aspects, a heterocycyl group includes 5 to about 10 ring atoms, in which one or more of the atoms in the ring system is an element or elements other than carbon, e.g., nitrogen, oxygen or sulfur. In some aspects, a heterocycyl group includes about 5 to about 6 ring atoms. In some aspects, a heterocyclyl group comprises one or more $sp^2$-hybridized atoms (e.g., a ring incorporating an carbonyl, endocyclic olefin, or exocyclic olefin). The prefix "aza," "oxa," or "thia" before heterocyclyl means that at least one nitrogen atom ("aza"), oxygen atom ("oxa"), or sulfur atom ("thia") is present as a heterocyclyl ring atom. In some aspects, the nitrogen or sulfur atom of the heterocyclyl group is oxidized to the corresponding N-oxide, S-oxide or S,S-dioxide. In some aspects, cycloalkyl includes a spirocyclic ring (i.e., spiroheterocyclyl). Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylalkyl" as used herein includes a heterocyclyl-alkylene-group wherein heterocyclyl and alkylene are as defined herein.

"Heteroaryl" as used herein includes an aromatic monocyclic or multicyclic ring system of 5 to about 14 ring atoms, in which at least one of the atoms in the ring system is an element other than carbon, i.e., nitrogen, oxygen or sulfur. In some aspects, the heteroaryl group includes 5 to about 10 ring atoms. In further aspects, the heteroaryl group contains 5 to 6 ring atoms.

The prefix "aza," "oxa," or "thia" before heteroaryl means that at least a nitrogen, oxygen or sulfur atom respectively is present as a ring atom. In some aspects, a nitrogen atom of a heteroaryl is oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Hydroxyalkyl" as used herein includes an alkyl group as defined herein substituted with one or more hydroxy groups (i.e., —OH). In some aspects, the alkyl group is lower alkyl. Representative hydroxyalkyl groups include hydroxymethyl and 2-hydroxyethyl.

When any two substituent groups or any two instances of the same substituent group are "independently selected" from a list of alternatives, they may be the same or different. For example, if $R^a$ and $R^b$ are independently selected from methyl, hydroxymethyl, ethyl, hydroxyethyl, or propyl, then a molecule with two $R^a$ groups and two $R^b$ groups could have all groups be methyl. Alternatively, the first $R^a$ could be methyl, the second $R^a$ could be ethyl, the first $R^b$ could be propyl, and the second $R^b$ could be hydroxymethyl (or any other substituents taken from the group). Alternatively, both $R^a$ and the first $R^b$ could be ethyl, while the second $R^b$ could be hydroxymethyl (i.e., some pairs of substituent groups may be the same, while other pairs may be different).

As used herein, "or" should in general be construed non-exclusively. For example, an embodiment of "a composition comprising A or B" would typically present an aspect with a composition comprising both A and B, and an embodiment of "a method to slow or stop germination biofilms" could slow germination, stop germination, or a combination of both (e.g., stop altogether for several days, after which it could proceed at a slower-than-usual rate). "Or" should, however, be construed to exclude those aspects presented that cannot be combined without contradiction (e.g., a formulation pH that is between 9 and 10 or between 7 and 8).

"Spirocyclic" as used herein includes a ring in which geminal substituents on an atom (typically, a carbon atom) form a 1,1-substituted ring. For example, "spirocycloalkyl" as used herein includes a cycloalkyl in which geminal substituents on a carbon atom form a 1,1-substituted ring (i.e., a "spirocyclic" cycloalkyl ring). In some aspects, a spirocyclic ring can have other substituents (e.g., 4,4-dimethylspirocyclohexyl).

In the Summary of the Invention above, Detailed Description, and the claims below, reference is made to particular features and aspects of the invention, including method steps. The disclosure of the invention in this specification is intended to include combinations of such particular features within the embodiments of the invention disclosed, at least to the extent that such combinations are non-contradictory. For example, if the Detailed Description presents aspects A, B, and C of an broader embodiment, it is understood that this also discloses particular embodiments including both aspects A and B, both aspects B and C, and both aspects A and C, as well as an embodiment with aspects A, B, and C.

DETAILED DESCRIPTION OF THE INVENTION

The present application provides selective abscisic acid (ABA) agonists. The agonists described herein activate the ABA pathway in plants (e.g., plant vegetative tissues) and induce abiotic stress tolerance. The new agonists can be used to induce stress tolerance in crop species of monocot or dicot plants.

Abscisic acid is a multifunctional phytohormone involved in a variety of phyto-protective functions including bud dormancy, seed dormancy or maturation, abscission of leaves and fruits, and response to a wide variety of biological stresses (e.g., cold, heat, salinity, and drought). ABA is also responsible for regulating stomatal closure by a mechanism independent of $CO_2$ concentration. The PYR/PYL family of ABA receptor proteins mediate ABA signaling. Plants examined to date express more than one PYR/PYL receptor protein family member, which have at least somewhat redundant activity. PYR/PYL receptor proteins mediate ABA signaling as a positive regulator in, for example, seed germination, post-germination growth, stomatal movement and plant tolerance to stress including, but not limited to, drought.

A wide variety of wild-type (naturally occurring) PYR/PYL polypeptide sequences are known in the art. Although PYR1 was originally identified as an abscisic acid (ABA) receptor in *Arabidopsis*, in fact, PYR1 is a member of a group of at least 14 proteins (PYR/PYL proteins) in the same protein family in *Arabidopsis* that also mediates ABA signaling. This protein family is also present in other plants (see, e.g., SEQUENCE LISTING) and is characterized in part by the presence of one or more or all of a polyketide cyclase domain 2 (PF10604), a polyketide cyclase domain 1 (PF03364), and a Bet V I domain (PF03364). START/Bet v 1 superfamily domain are described in, for example, Radauer, *BMC Evol. Biol.* 8:286 (2008). In some embodiments, a wild-type PYR/PYL receptor polypeptide comprises any of SEQ ID NOs:1-119. In some embodiments, a wild-type PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NOs:1-119. In some embodiments, a PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, or 119.

I. ABA Agonists

The present invention provides for small-molecule ABA agonists, i.e., compounds that activate PYR/PYL proteins. In some aspects, the present invention provides for a compound or a composition as set forth herein (i.e., in one or more of the other aspects, such as formulations or methods, and embodiments herein). In some aspects, the present invention provides a formulation comprising, consisting essentially of, or consisting of a compound as set forth herein. In some aspects, the present invention provides a method of using or use of a compound or formulation as set forth herein.

In one aspect, the present invention provides a method of increasing abiotic stress tolerance in a plant, the method comprising contacting a plant with an effective amount of a sulfonamide agonist compound to increase abiotic stress tolerance in the plant, thereby increasing abiotic stress tolerance, wherein the sulfonamide agonist compound is of Formula I:

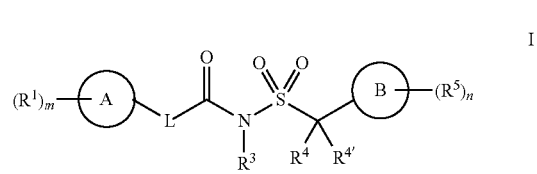

wherein:

A is selected from the group consisting of alkyl, aryl, arylalkyl, heteroaryl, heteroarylalkyl, heterocyclyl, and cycloalkyl;

each $R^1$ is a substituent independently selected from the group including alkyl, alkenyl, alkynyl, cycloalkyl, heterocyclyl, aryl, heteroaryl, halo, fluoroalkyl, hydroxyl, hydroxyalkyl, alkoxy, fluoroalkoxy, alkoxyalkyl, amino, aminoalkyl, alkylthio, alkylthioalkyl, cyano, carboxyl, carboxyalkyl, alkoxycarbonyl, alkoxycarbonylalkyl, amido, and amidoalkyl; wherein the $R^1$ cycloalkyl, heterocyclyl, aryl, or heteroaryl is additionally substituted with from 0 to 3 $R^6$; or alternatively, two $R^1$ substituents join to form an additional $R^1$ ring, wherein the additional $R^1$ ring is selected from the group including aryl, heteroaryl, cycloalkyl, and heterocyclyl; and wherein the additional $R^1$ ring is additionally substituted with from 0 to 3 $R^6$; or alternatively, an $R^1$ and a $R^2$ substituent join to form an $R^{1,2}$ ring, wherein the $R^{1,2}$ ring is selected from the group including cycloalkyl and heterocyclyl; and wherein the $R^{1,2}$ ring is additionally substituted with from 0 to 3 $R^6$;

m is an integer selected from 0 to 5; wherein if A is not aryl or if at least two $R^1$ are not halo, m is an integer selected from 0 to 3;

L is a bond, —C($R^2$)($R^{2'}$)—, —O—, or —$NR^6$—; wherein if L is a bond, A is not alkyl; $R^2$ and $R^{2'}$ are each a substituent independently selected from the group including hydrogen, alkyl, fluoroalkyl, cycloalkyl, heterocycyl, heteroaryl, and aryl; wherein the cycloalkyl, heterocycyl, heteroaryl, and aryl is additionally substituted with from 0 to 3 $R^6$; or alternatively, an $R^2$ and an $R^{2'}$ join to form a geminal $R^2$ ring, wherein the geminal $R^2$ ring is selected from the group including cycloalkyl, cycloalkenyl, and heterocyclyl; and wherein the geminal $R^2$ ring is additionally substituted with from 0 to 4 $R^6$; or alternatively, the $R^2$ is joined into the $R^{1,2}$ ring;

$R^3$ is a substituent selected from the group including hydrogen, alkyl, and fluoroalkyl; and $R^4$ and $R^{4'}$ are each a substituent independently selected from the group including hydrogen, alkyl, chloro, fluoro, and fluoroalkyl; or alternatively, an $R^4$ and an $R^{4'}$ join to form a geminal $R^4$ ring, wherein the geminal $R^4$ ring is selected from the group including cycloalkyl, cycloalkenyl, and heterocyclyl; and wherein the geminal $R^4$ ring is additionally substituted with from 0 to 4 $R^6$;

B is selected from the group including aryl, heteroaryl, heterocyclyl, and cycloalkyl;

each $R^5$ is a substituent independently selected from the group including alkyl, alkenyl, alkynyl, cycloalkyl, heterocyclyl, aryl, heteroaryl, halo, fluoroalkyl, nitro, hydroxyl, hydroxyalkyl, alkoxy, alkoxyalkyl, amino, aminoalkyl, alkylthio, alkylthioalkyl, cyano, carboxyl, carboxyalkyl, alkoxycarbonyl, alkoxycarbonylalkyl, amido, and amidoalkyl; or alternatively, two $R^5$ join to form an additional $R^5$ ring, wherein the additional $R^5$ ring is selected from the group including aryl, heteroaryl, cycloalkyl, and heterocyclyl; and wherein the additional $R^5$ ring is additionally substituted with from 0 to 5 $R^6$;

n is an integer selected from 0 to 5; wherein if B is not aryl or if at least two $R^5$ are not halo, m is an integer selected from 0 to 3; and each $R^6$ is a substituent independently selected from the group including alkyl, aryl, halo, fluoroalkyl, hydroxyl, alkoxy, amino, cyano, carboxyl, alkoxycarbonyl, and amido.

In one aspect, the present invention provides a method of increasing abiotic stress tolerance in a plant, the method comprising a step of contacting a plant with an effective amount of a compound to increase abiotic stress tolerance in the plant, where the compound is of Formula IB:

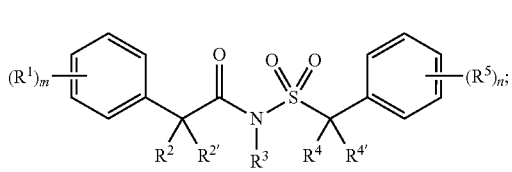

IB where each $R^1$ is a substituent independently selected from alkyl, alkenyl, alkynyl, cycloalkyl, heterocyclyl, aryl, heteroaryl, halo, fluoroalkyl, hydroxyl, hydroxyalkyl, alkoxy, alkoxyalkyl, amino, aminoalkyl, alkylthio, alkylthioalkyl, cyano, carboxyl, carboxyalkyl, alkoxycarbonyl, alkoxycarbonylalkyl, amido, or amidoalkyl; or, alternatively, two $R^1$ substituents join to form an additional $R^1$ ring, where the additional $R^1$ ring is selected from aryl, heteroaryl, cycloalkyl, or heterocyclyl; and where the additional $R^1$ ring is additionally substituted with from 0 to 3 $R^6$; or an $R^1$ and a $R^2$ substituent join to form an $R^{1,2}$ ring, where the $R^{1,2}$ ring is selected from cycloalkyl or heterocyclyl; and where the $R^{1,2}$ ring is additionally substituted with from 0 to 3 $R^6$;

m is an integer selected from 0 to 3;

$R^2$ and $R^{2'}$ are each a substituent independently selected from hydrogen, alkyl, or fluoroalkyl;

or, alternatively, an $R^2$ and an $R^{2'}$ join to form a geminal $R^2$ ring, where the geminal $R^2$ ring is selected from cycloalkyl, cycloalkenyl, or heterocyclyl; and where the geminal $R^2$ ring is additionally substituted with from 0 to 3 $R^6$; or the $R^2$ is joined into the $R^{1,2}$ ring;

$R^3$ is a substituent selected from hydrogen, alkyl, or fluoroalkyl;

$R^4$ and $R^{4'}$ are each a substituent independently selected from hydrogen, alkyl, chloro, fluoro, or fluoroalkyl;

each $R^5$ is a substituent independently selected alkyl, alkenyl, alkynyl, cycloalkyl, heterocyclyl, aryl, heteroaryl, halo, fluoroalkyl, nitro, hydroxyl, hydroxyalkyl, alkoxy, alkoxyalkyl, amino, aminoalkyl, alkylthio, alkylthioalkyl, cyano, carboxyl, carboxyalkyl, alkoxycarbonyl, alkoxycarbonylalkyl, amido, or amidoalkyl; or, alternatively, two $R^5$ join to form an additional $R^5$ ring, wherein the additional $R^5$ ring is selected from aryl, heteroaryl, cycloalkyl, or heterocyclyl; and wherein the additional $R^5$ ring is additionally substituted with from 0 to 3 $R^6$;

n is an integer selected from 0 to 3; and each $R^6$ is a substituent independently selected from alkyl, aryl, halo, fluoroalkyl, hydroxyl, alkoxy, amino, cyano, carboxyl, alkoxycarbonyl, or amido.

As previously discussed, the embodiments (and further aspects) set forth herein may generally be applied to either Formula I, IB, II, III, IIIB, or IV, except when such application is impossible (e.g., Formula IB does not include A or B as Markush groups) and may be further combined to create subgenera of the embodiments as disclosed.

In some embodiments, L is —O—. In some embodiments, L is —C($R^2$)($R^{2'}$)—. In some embodiments, L is a bond; in some embodiments, A is not alkyl. In some embodiments, L is —$NR^6$—.

In some embodiments, A is alkyl or arylalkyl. In some embodiments, A is isobutyl. In some embodiments, A is lower alkyl (e.g., methyl).

In some embodiments, A is aryl. In some embodiments, A is phenyl, 4-cyanophenyl, 4-nitrophenyl, or 4-fluorophenyl.

In some embodiments, A is heteroaryl. In some embodiments, A is 2-, 3-, or 4-pyridyl.

In some embodiments, the sulfonamide agonist compound is

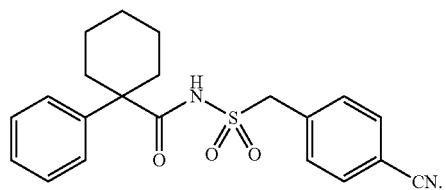 [SMILES: N#Cc1ccc(CS(=O)(=O)NC(=O)C2(c3ccccc3)CCCCC2)cc1]

In some embodiments, the sulfonamide agonist compound is of Formula II:

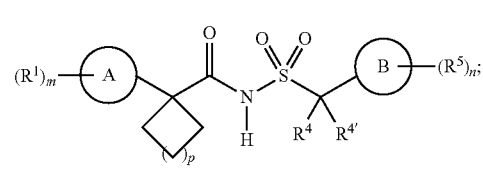

II wherein:

p is an integer selected from 0 to 4;

$R^4$ and $R^{4'}$ are independently hydrogen or lower alkyl; and

B is heteroaryl.

In some embodiments, the sulfonamide agonist compound is of Formula III:

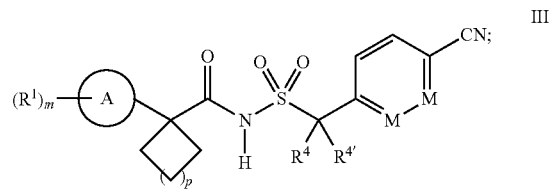

III wherein:

p is an integer selected from 0 to 4;

$R^4$ and $R^{4'}$ are independently hydrogen or lower alkyl; and each M is independently C or N.

In some embodiments, A is selected from the group including 2-thiophenyl, 3-thiophenyl, 2-furanyl, and 3-furanyl. In some embodiments, A is selected from the group including 2-thiophenyl, 3-thiophenyl, 2-furanyl, 3-furanyl, 2-pyrrolyl, and 3-pyrrolyl. In some embodiments, A is selected from the group including 2-thiophenyl and 3-thiophenyl.

In some embodiments, the sulfonamide agonist compound is of Formula IIIB:

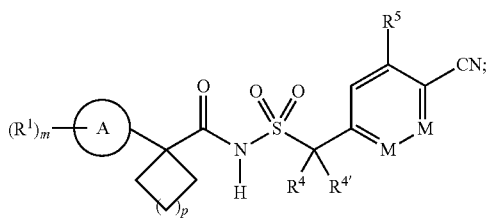

IIIB wherein:

p is an integer selected from 0 to 4;

$R^4$ and $R^{4'}$ are independently hydrogen or lower alkyl; and each M is independently CH, $CR^5$, or N.

In some embodiments, each M is independently CH or N. In some embodiments, each M is independently CH or $CR^5$. In some embodiments, each M is CH.

In some embodiments, A is selected from the group including 2-thiophenyl, 3-thiophenyl, 2-furanyl, and 3-furanyl. In some embodiments, A is selected from the group including 2-thiophenyl, 3-thiophenyl, 2-furanyl, 3-furanyl, 2-pyrrolyl, and 3-pyrrolyl. In some embodiments, A is selected from the group including 2-thiophenyl and 3-thiophenyl.

In some embodiments, $R^5$ is a meta-substituent (e.g., 3-halo, such as 3-chloro).

In some embodiments, the sulfonamide agonist compound is of Formula IV:

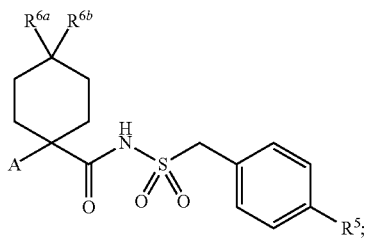

IV wherein $R^{6a}$ and $R^{6b}$ are each independently selected from the group including hydrogen, hydroxyl, alkoxy, alkyl, fluoroalkyl, and halo.

In some embodiments, the sulfonamide agonist compound is selected from the group including

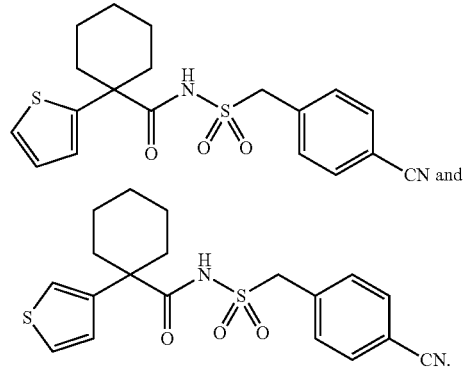

In some embodiments, A is cycloalkyl. In some embodiments, A is cyclohexyl.

In some embodiments, $R^1$ is selected from the group including alkyl, fluoroalkyl, alkoxy, and cyano.

In some embodiments, $R^1$ is a substituent independently selected from alkyl, alkenyl, cycloalkyl, heterocyclyl, aryl, heteroaryl (e.g., pyridyl), halo (e.g., fluoro, chloro), fluoroalkyl, hydroxyl, hydroxyalkyl, alkoxy, fluoroalkoxy, alkoxyalkyl, amino, aminoalkyl, cyano, carboxyl, carboxyalkyl, alkoxycarbonyl, alkoxycarbonylalkyl, amido, or amidoalkyl. In some embodiments, $R^1$ is alkyl, alkoxy, cyano, or halo.

In some embodiments, $R^1$ is independently selected from alkyl, fluoroalkyl, alkoxy, fluoroalkoxy, or cyano. In some embodiments, at least one $R^1$ is alkyl (e.g., methyl, ethyl, propyl, isopropyl, butyl, or isobutyl). In some embodiments, at least one $R^1$ is fluoroalkyl (e.g., trifluoromethyl, perfluoroethyl, or 2,2,2-trifluoroethyl). In some embodiments, at least one $R^1$ is alkoxy (e.g., methoxy, ethoxy, propoxy, isopropoxy, butoxy, or isobutoxy). In some embodiments, at least one $R^1$ is fluoroalkoxy (e.g., trifluoromethoxy or 2,2,2-trifluoroethoxy). In some embodiments, at least one $R^1$ is cyano (e.g., 4-cyano). In some embodiments, at least one $R^1$ is selected from cyano, halo, or nitro.

In some embodiments, $R^1$ is a para-substituent (e.g., 4-cyano). In some embodiments, $R^1$ is a meta-substituent. In some embodiments, $R^1$ is an ortho-substituent.

In some embodiments, two $R^1$ substituents (e.g., adjacent $R^1$ substituents) join to form an additional $R^1$ ring, where the additional $R^1$ ring is selected from aryl, heteroaryl, cycloalkyl, or heterocyclyl; and where the additional $R^1$ ring is additionally substituted with 0, 1, 2, or 3 $R^6$. In some embodiments, the additional $R^1$ ring is cyclohexyl or cyclopentyl (e.g., cyclohexyl). In some embodiments, the additional $R^1$ ring is heteroaryl (e.g., pyridyl, as in 62). In some embodiments, the additional $R^1$ ring is substituted with 0 or 1 $R^6$ (e.g., alkyl, such as methyl; halo, such as chloro).

In some embodiments, an $R^1$ and a $R^2$ substituent join to form an $R^{1,2}$ ring, where the $R^{1,2}$ ring is selected from cycloalkyl or heterocyclyl; and where the $R^{1,2}$ ring is additionally substituted with 0, 1, 2, or 3 $R^6$. In some embodiments, the $R^{1,2}$ ring is cyclohexyl or cyclopentyl (e.g., cyclohexyl). In some embodiments, the $R^{1,2}$ ring is substituted with 0 or 1 $R^6$ (e.g., alkyl, such as methyl).

In some embodiments, m is 0. In some embodiments, m is 1. In some embodiments, m is 2. In some embodiments, m is 3.

In some embodiments, $R^2$ is alkyl. In some embodiments, $R^2$ and $R^{2'}$ are selected from the group including methyl, ethyl, and propyl.

In some embodiments, $R^2$ and $R^{2'}$ join to form the geminal $R^2$ ring. In some embodiments, $R^2$ and $R^{2'}$ join to form a geminal cyclopropyl ring. In some embodiments, $R^2$ and $R^{2'}$ join to form a geminal cyclobutyl ring. In some embodiments, $R^2$ and $R^{2'}$ join to form a geminal cyclopenyl ring. In some embodiments, $R^2$ and $R^{2'}$ join to form a geminal cyclohexyl ring. In some embodiments, $R^2$ and $R^{2'}$ join to form a geminal 4-methylcyclohexyl ring. In some embodiments, $R^2$ and $R^{2'}$ join to form a geminal 4,4-dimethylcyclohexyl ring. In some embodiments, $R^2$ and $R^{2'}$ join to form a geminal piperidinyl, N-acylpiperidinyl, or N-alkylpiperidinyl ring. In some embodiments, $R^2$ and $R^{2'}$ join to form a geminal tetrahydro-2H-pyranyl ring. In some embodiments, $R^2$ and $R^{2'}$ join to form a geminal cycloheptyl ring.

In some embodiments, $R^2$ is cycloalkyl. In some embodiments, $R^2$ is cyclohexyl.

In some embodiments, $R^2$ is aryl. In some embodiments, $R^2$ is 4-fluorophenyl.

In some embodiments, $R^2$ and $R^{2'}$ are each a substituent independently selected from the group hydrogen, alkyl, or fluoroalkyl. In some embodiments, $R^2$ is hydrogen. In some embodiments, $R^2$ and $R^{2'}$ are hydrogen. In some embodiments, $R^2$ is alkyl. In a further aspect, $R^2$ and $R^{2'}$ are each a substituent independently selected from methyl, ethyl, or propyl. In some embodiments, $R^2$ is fluoroalkyl (e.g., trifluoromethyl).

In some embodiments, $R^2$ and $R^{2'}$ join to form a geminal $R^2$ ring, where the geminal $R^2$ ring is selected from the group cycloalkyl, cycloalkenyl, or heterocyclyl; and where the geminal $R^2$ ring is additionally substituted with from 0 to 3 $R^6$. In some embodiments, $R^2$ and $R^{2'}$ join to form a geminal $R^2$ ring. In some further aspects, $R^2$ and $R^{2'}$ join to form a geminal cyclopropyl, cyclobutyl, cyclopentyl, cyclohexyl, or cycloheptyl ring (e.g., cyclopropyl). In an alternative further aspect, $R^2$ and $R^{2'}$ join to form a geminal piperidinyl, N-acylpiperidinyl, or N-alkylpiperidinyl ring. In some embodiments, $R^2$ and $R^{2'}$ join to form a geminal ring, where the geminal $R^2$ ring is additionally substituted with from 0, 1, 2, or 3 $R^6$ (e.g., alkyl, such as methyl).

In some embodiments, $R^2$ is joined into the $R^{1,2'}$ ring.

In some embodiments, $R^2$ is alkyl. In some embodiments, $R^2$ and $R^{2'}$ are each a substituent independently selected from methyl, ethyl, or propyl.

In some embodiments, $R^2$ and $R^{2'}$ join to form a geminal $R^2$ ring. In some embodiments, $R^2$ and $R^{2'}$ join to form a geminal cyclopropyl, cyclobutyl, cyclopentyl, cyclohexyl, or cycloheptyl ring. In some alternative embodiments, $R^2$ and $R^{2'}$ join to form a geminal piperidinyl, N-acylpiperidinyl, or N-alkylpiperidinyl ring. In some alternative embodiments, $R^2$ and $R^{2'}$ join to form a geminal tetrahydro-2H-pyranyl ring.

In some embodiments, the compound is achiral (e.g., when $R^2$ and $R^{2'}$ are both hydrogen, and the compound contains no other enantiomeric centers). In some embodiments, the compound is racemic at the carbon substituted with $R^2$ and $R^{2'}$. In some embodiments, the compound is enantiomerically enriched with the R-stereocenter (i.e., at least 1% enantiomeric excess of the R-stereoisomer at this site, and in some embodiments, at least 10%, 20% 30%, 40%, 50%, 60% 70%, 80%, 90%, 93%, 95%, 97%, 98%, or 99% enantiomeric excess). In some embodiments, the steroecenter is enantiomerically enriched with the S-stereocenter (i.e., at least 1% enantiomeric excess of the S-stereoisomer at this site, and in some embodiments, at least 10%, 20% 30%, 40%, 50%, 60% 70%, 80%, 90%, 93%, 95%, 97%, 98%, or 99% enantiomeric excess).

In some embodiments, $R^3$ is hydrogen.

In some embodiments, $R^3$ is a substituent selected from the group hydrogen, alkyl, or fluoroalkyl. In some embodiments, $R^3$ is hydrogen. In some embodiments, $R^3$ is alkyl (e.g., methyl, ethyl, propyl, isopropyl, butyl, or isobutyl). In some embodiments, $R^3$ is fluoroalkyl (e.g., trifluoromethyl, perfluoroethyl, or 2,2,2-trifluoroethyl).

In some embodiments, $R^4$ is hydrogen or alkyl. In some embodiments, $R^4$ and $R^{4'}$ are methyl.

In some embodiments, $R^4$ and $R^{4'}$ are each a substituent independently selected from hydrogen, alkyl, chloro, fluoro, or fluoroalkyl. In some embodiments, $R^4$ and $R^{4'}$ are each independently hydrogen or alkyl. In some embodiments, $R^4$ is alkyl (e.g., methyl, ethyl, propyl, isopropyl, butyl, or isobutyl). In some embodiments, $R^4$ is fluoroalkyl (e.g., trifluoromethyl, perfluoroethyl, or 2,2,2-trifluoroethyl).

In some embodiments, the compound is achiral (e.g., when $R^4$ and $R^{4'}$ are both hydrogen, and the compound contains no other enantiomeric centers). In some embodiments, the compound is racemic at the carbon substituted with $R^4$ and $R^{4'}$. In some embodiments, the compound is enantiomerically enriched with the R-stereocenter (i.e., at least 1% enantiomeric excess of the R-stereoisomer at this site, and in some embodiments, at least 10%, 20% 30%, 40%, 50%, 60% 70%, 80%, 90%, 93%, 95%, 97%, 98%, or 99% enantiomeric excess). In some embodiments, the steroecenter is enantiomerically enriched with the S-stereocenter (i.e., at least 1% enantiomeric excess of the S-stereoisomer at this site, and in some embodiments, at least 10%, 20% 30%, 40%, 50%, 60% 70%, 80%, 90%, 93%, 95%, 97%, 98%, or 99% enantiomeric excess).

In some embodiments, the compound is racemic at a site other than the $R^2/R^{2'}$ carbon or the $R^4/R^{4'}$ carbon. In some embodiments, the compound is enantiomerically enriched with the R-stereocenter (i.e., at least 1% enantiomeric excess of the R-stereoisomer at this site, and in some embodiments, at least 10%, 20% 30%, 40%, 50%, 60% 70%, 80%, 90%, 93%, 95%, 97%, 98%, or 99% enantiomeric excess). In some embodiments, the steroecenter is enantiomerically enriched with the S-stereocenter (i.e., at least 1% enantiomeric excess of the S-stereoisomer at this site, and in some embodiments, at least 10%, 20% 30%, 40%, 50%, 60% 70%, 80%, 90%, 93%, 95%, 97%, 98%, or 99% enantiomeric excess).

In some embodiments, B is aryl. In some embodiments, B is phenyl.

In some embodiments, B is heteroaryl.

In some embodiments, B is a species or Markush that is set forth herein as an embodiment of A.

In some embodiments, n is 0. In some embodiments, n is 1. In some embodiments, n is 2 (e.g., independently selected para- and meta-substituents). In some embodiments, n is 3.

In some embodiments, $R^5$ is a para-substituent. In some embodiments, $R^5$ is independently selected from the group including cyano, fluoro, halo, and nitro.

In some embodiments, $R^5$ is a substituent independently selected from alkyl, alkenyl, cycloalkyl, heterocyclyl, aryl, heteroaryl (e.g., pyridyl), halo (e.g., fluoro, chloro), fluoroalkyl, hydroxyl, hydroxyalkyl, alkoxy, fluoroalkoxy, alkoxyalkyl, amino, aminoalkyl, cyano, carboxyl, carboxyalkyl, alkoxycarbonyl, alkoxycarbonylalkyl, amido, or amidoalkyl. In some embodiments, $R^5$ is alkyl, alkoxy, cyano, or halo. In some embodiments, $R^5$ is selected from cyano, halo, or nitro.

In some embodiments, $R^5$ is independently selected from alkyl, fluoroalkyl, alkoxy, fluoroalkoxy, or cyano. In some embodiments, at least one $R^5$ is alkyl (e.g., methyl, ethyl, propyl, isopropyl, butyl, or isobutyl). In some embodiments, at least one R[5] is fluoroalkyl (e.g., trifluoromethyl, perfluoroethyl, or 2,2,2-trifluoroethyl). In some embodiments, at least one R[5] is alkoxy (e.g., methoxy, ethoxy, propoxy, isopropoxy, butoxy, or isobutoxy). In some embodiments, at least one R[5] is fluoroalkoxy (e.g., trifluoromethoxy or 2,2,2-trifluoroethoxy). In some embodiments, at least one R[5] is cyano (e.g., 4-cyano).

In some embodiments, R[5] is selected from cyano, halo, or nitro. In some embodiments, R[5] is halo. In some embodiments, R[5] is cyano. In some embodiments, R[5] is nitro. In some embodiments, R[5] is para-.

In some embodiments, R[5] is a hydrogen bond acceptor (i.e., a group that includes an electron pair on a electronegative heteroatom, such as N, O, S, or a halogen). In some embodiments, R[5] is hydroxyl. In some embodiments, R[5] is lower alkoxy or cyclopropyloxy.

In some embodiments, R[5] is amino. In some embodiments, R[5] is lower alkylamino. In some embodiments, R[5] is carboxy. In some embodiments, R[5] is lower alkoxycarbonyl. In some embodiments, R[5] is amido. In some embodiments, R[5] is lower alkylamido. In some embodiments, R[5] is thio. In some embodiments, R[5] is lower alkylthio. In some embodiments, the R[5] acceptor is para-.

In some embodiments, R[5] is a para-substituent (e.g., 4-cyano). In some embodiments, R[5] is a meta-substituent (e.g., 3-halo). In some embodiments, R[5] is an ortho-substituent.

In some embodiments, the ring includes para- and meta-R[5] substituents. In some embodiments, one of the R[5] substituents is a cyano group (e.g., 4-cyano). In some embodiments, one of the R[5] substituents is a halo group (e.g., 3-chloro).

In some embodiments, two R[5] substituents (e.g., adjacent R[5] substituents) join to form an additional R[5] ring, where the additional R[5] ring is selected from aryl, heteroaryl, cycloalkyl, or heterocyclyl; and where the additional R[5] ring is additionally substituted with 0, 1, 2, or 3 R[6]. In some embodiments, the additional R[5] ring is cyclohexyl or cyclopentyl (e.g., cyclohexyl). In some embodiments, the additional R[5] ring is heteroaryl (e.g., pyridyl). In some embodiments, the additional R[5] ring is substituted with 0 or 1 R[6] (e.g., alkyl, such as methyl; halo, such as chloro).

In some embodiments, each R[6] is a substituent independently selected from alkyl, aryl, halo, fluoroalkyl, hydroxyl, alkoxy, amino, cyano, carboxyl, alkoxycarbonyl, or amido. In some embodiments, each R[6] is a substituent independently selected from alkyl, halo, fluoroalkyl, cyano, or carboxyl. In some embodiments, each R[6] is a substituent independently selected from the group alkyl, halo, or fluoroalkyl. In some embodiments, each R[6] is a substituent independently selected from alkyl or halo.

In some embodiments, the sulfonamide agonist compound is any compound or set of compounds set forth in the specification and drawings of the instant application.

In some embodiments, the plant is a monocot. In some embodiments, the plant is a dicot.

In some embodiments, the abiotic stress tolerance comprises drought tolerance.

In some embodiments, the contacting step comprises delivering the formulation to the plant by aircraft or irrigation.

In some aspects, the present invention provides a method of inhibiting seed germination in a plant, the method comprising contacting a seed with a sufficient amount of the sulfonamide agonist compound set forth herein to inhibit germination. In some embodiments, the method comprises contacting a plant with a sufficient amount of the agricultural formulation set forth herein to inhibit germination.

In some aspects, the present invention provides a method of reducing transpiration in a plant, the method comprising contacting a plant with a sufficient amount of the sulfonamide agonist compound set forth herein to reduce transpiration. In some embodiments, the method comprises contacting a plant with a sufficient amount of the agricultural formulation set forth herein to reduce transpiration.

In some aspects, the present invention provides a method of activating a PYR/PYL protein, the method comprising contacting the PYR/PYL protein with the sulfonamide agonist compound set forth herein.

In some embodiments, the PYR/PYL protein is selectively activated.

In some embodiments, the PYR/PYL protein is expressed by a cell. In some aspects, the cell is a plant cell.

In some embodiments, the PYR/PYL protein is PYL-5. In some embodiments, the PYR/PYL protein is PYL-8. In some embodiments, the PYR/PYL protein is PYL-9.

In some aspects, the method further comprises using a second active compound.

In some embodiments, the second active compound is a PYR/PYL receptor full agonist. In some embodiments, the second active compound is a PYR/PYL receptor partial agonist.

In some embodiments, the second active compound is a PYR/PYL receptor superagonist.

In some embodiments, the second active compound is selected from the group including quinabactin, racemic ABA, R-ABA, and S-ABA.

In some embodiments, the second active compound is selected from the group including benoxacor, benzothiadiazole, dichlorobenil, fludioxonil, and mandipropamid.

In some aspects, the present invention provides the sulfonamide agonist compound as disclosed herein, with the proviso that the compound is not selected from the group including:

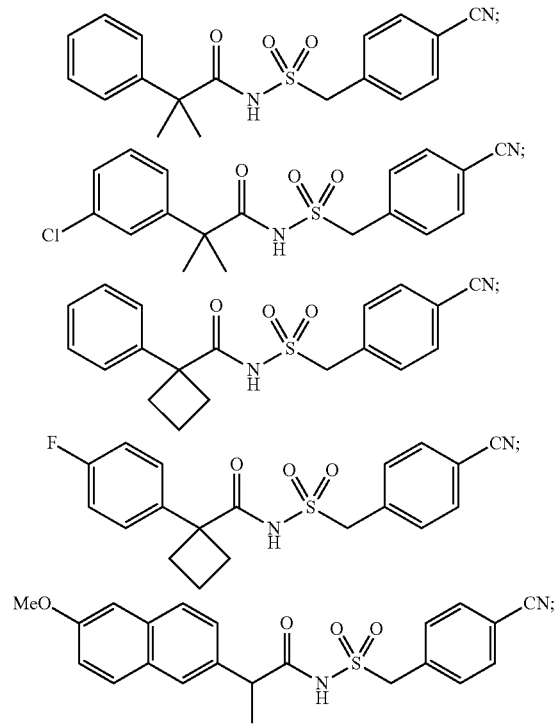

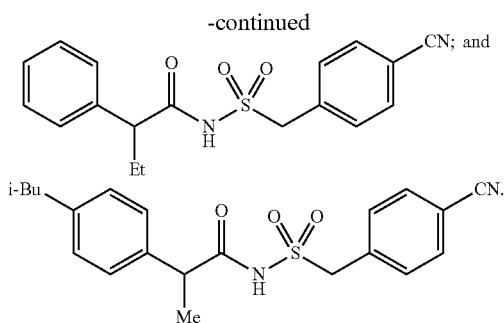

In some aspects, the present invention provides a method of increasing abiotic stress tolerance in a plant, the method comprising: contacting a plant with a sufficient amount of the sulfonamide agonist compound as disclosed herein or the agricultural formulation as disclosed herein, thereby increasing abiotic stress tolerance in the plant.

In some aspects, the abiotic stress tolerance comprises drought tolerance.

In some aspects, the method comprises: delivering the compound or the formulation to the plant by aircraft or irrigation.

In some aspects, the present invention provides a method of inhibiting seed germination in a plant, the method comprising: contacting a seed with a sufficient amount of the sulfonamide agonist composition as disclosed herein.

In some aspects, the present invention provides a plant in contact with the sulfonamide agonist compound as disclosed herein or the agricultural formulation as disclosed herein. In some aspects, the plant is a seed.

In some aspects, the present invention provides a method of activating a PYR/PYL protein, the method comprising: contacting the PYR/PYL protein with the sulfonamide agonist compound as disclosed herein or the agricultural formulation as disclosed herein. In some embodiments, the PYR/PYL protein is expressed by a cell. In some embodiments, the cell is a plant cell.

Exemplary compounds according to the formulas above are shown below in Tables I to V, X, and XI. In some embodiments, each of the substituents included in Tables I to V, X, and XI can be combined with the other substituents described. For example, certain embodiments include compounds of Formula I with the $R^1$, $R^2$, and $R^{2'}$ substitution pattern set forth in exemplary compound 24 (i.e., $R^1$=4-fluoro; $R^2$ and $R^{2'}$ join to form a geminal cyclopentyl ring).

In some embodiments, the contacting step comprises delivering the formulation to the plant by aircraft or irrigation.

In some embodiments, the abiotic stress tolerance comprises drought tolerance.

In some aspects, the present invention provides a plant in contact with a compound or formulation as set forth herein.

II. ABA Agonist Formulations

The present invention provides agricultural chemical formulations formulated for contacting to plants, wherein the formulation comprises an ABA agonist of the present invention. In some embodiments, the plants that are contacted with the agonists comprise or express an endogenous PYR/PYL polypeptide. In some embodiments, the plants that are contacted with the agonists do not comprise or express a heterologous PYR/PYL polypeptide (e.g., the plants are not transgenic or are transgenic but express heterologous proteins other than heterologous PYR/PYL proteins). In some embodiments, the plants that are contacted with the agonists do comprise or express a heterologous PYR/PYL polypeptide.

The formulations can be suitable for treating plants or plant propagation material, such as seeds, in accordance with the present invention, e.g., in a carrier. Suitable additives include buffering agents, wetting agents, coating agents, polysaccharides, and abrading agents. In some embodiments, the formulation further comprises a carrier. Exemplary carriers include water, aqueous solutions, slurries, solids and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal. Any agriculturally suitable carrier known to one skilled in the art would be acceptable and is contemplated for use in the present invention). Optionally, the formulations can also include at least one surfactant, herbicide, fungicide, pesticide, or fertilizer.

In some aspects, the present invention provides an agricultural formulation consisting of, consisting essentially of, or comprising a compound as set forth herein.

In some aspects, the present invention provides an agricultural formulation comprising the sulfonamide agonist compound as disclosed herein and an agriculturally acceptable adjuvant.

In some embodiments, the formulation further comprises at least one of a fungicide, an herbicide, a pesticide, a nematicide, an insecticide, a plant activator, a synergist, an herbicide safener, a plant growth regulator, an insect repellant, an acaricide, a molluscicide, or a fertilizer.

In some aspects, the agricultural formulation further comprises a surfactant.

In some aspects, the agricultural formulation further comprises a carrier.

In some embodiments, the agricultural chemical formulation comprises at least one of a surfactant, an herbicide, a pesticide, such as but not limited to a fungicide, a bactericide, an insecticide, an acaricide, and a nematicide, a plant activator, a synergist, an herbicide safener, a plant growth regulator, an insect repellant, or a fertilizer. In some embodiments, the formulation further comprises a surfactant.

In some embodiments, the agricultural chemical formulation comprises an effective amount of one or more herbicides selected from paraquat (592), mesotrione (500), sulcotrione (710), clomazone (159), fentrazamide (340), mefenacet (491), oxaziclomefone (583), indanofan (450), glyphosate (407), prosulfocarb (656), molinate (542), triasulfuron (773), halosulfuron-methyl (414), or pretilachlor (632). The above herbicidal active ingredients are described, for example, in "The Pesticide Manual", Editor C. D. S. Tomlin, 12th Edition, British Crop Protection Council, 2000, under the entry numbers added in parentheses; for example, mesotrione (500) is described therein under entry number 500. The above compounds are described, for example, in U.S. Pat. No. 7,338,920, which is incorporated by reference herein in its entirety.

In some embodiments, the agricultural chemical formulation comprises an effective amount of one or more fungicides selected from sedaxane, fludioxonil, penthiopyrad, prothioconazole, flutriafol, difenoconazole, azoxystrobin, captan, cyproconazole, cyprodinil, boscalid, diniconazole, epoxiconazole, fluoxastrobin, trifloxystrobin, metalaxyl, metalaxyl-M (mefenoxam), fluquinconazole, fenarimol, nuarimol, pyrifenox, pyraclostrobin, thiabendazole, tebuconazole, triadimenol, benalaxyl, benalaxyl-M, benomyl, carbendazim, carboxin, flutolanil, fuberizadole, guazatine, myclobutanil, tetraconazole, imazalil, metconazole, bitertanol, cymoxanil, ipconazole, iprodione, prochloraz, pencycuron, propamocarb, silthiofam, thiram, triazoxide, triticonazole, tolylfluanid, or a manganese compound (such as mancozeb, maneb). In some embodiments, the agricultural chemical formulation comprises an effective amount of one or more of an insecticide, an acaricide, or a nematcide selected from thiamethoxam, imidacloprid, clothianidin, lamda-cyhalothrin, tefluthrin, beta-cyfluthrin, permethrin, abamectin, fipronil, or spinosad. Details (e.g., structure, chemical name, commercial names, etc) of each of the above pesticides with a common name can be found in the e-Pesticide Manual, version 3.1, 13th Edition, Ed. CDC Tomlin, British Crop Protection Council, 2004-05. The above compounds are described, for example, in U.S. Pat. No. 8,124,565, which is incorporated by reference herein in its entirety.

In some embodiments, the agricultural chemical formulation comprises an effective amount of one or more fungicides selected from cyprodinil ((4-cyclopropyl-6-methyl-pyrimidin-2-yl)-phenyl-amine) (208), dodine (289); chlorothalonil (142); folpet (400); prothioconazole (685); boscalid (88); proquinazid (682); dithianon (279); fluazinam (363); ipconazole (468); or metrafenone. Some of the above compounds are described, for example, in "The Pesticide Manual" [The Pesticide Manual—A World Compendium; Thirteenth Edition; Editor: C. D. S. Tomlin; The British Crop Protection Council, 2003], under the entry numbers added in parentheses. The above compounds also are described, for example, in U.S. Pat. No. 8,349,345, which is incorporated by reference herein in its entirety.

In some embodiments, the agricultural chemical formulation comprises an effective amount of one or more fungicides selected from fludioxonil, metalaxyl, or a strobilurin fungicide, or a mixture thereof. In some embodiments, the strobilurin fungicide is azoxystrobin, picoxystrobin, kresoxim-methyl, or trifloxystorbin. In some embodiments, the agricultural chemical formulation comprises an effective amount of one or more of an insecticide selected from a phenylpyrazole or a neonicotinoid. In some embodiments, the phenylpyrazole is fipronil and the neonicotinoid is selected from thiamethoxam, imidacloprid, thiacloprid, clothianidin, nitenpyram or acetamiprid. The above compounds are described, for example, in U.S. Pat. No. 7,071,188, which is incorporated by reference herein in its entirety. In some embodiments, the agricultural chemical formulation comprises an effective amount of one or more biological pesticide, including but not limited to, *Pasteuria* spp., *Paeciliomyces, Pochonia chlamydosporia, Myrothecium metabolites, Muscodor volatiles, Tagetes* spp., *Bacillus firmus*, including *Bacillus firmus* CNCM 1-1582.

In some aspects, the invention presents a formulation or method as set forth herein that further comprises using a second active compound. In some embodiments, the second active compound is a PYR/PYL receptor agonist. In some embodiments, the second active compound is a PYR/PYL receptor partial agonist. In some embodiments, the second active compound is a PYR/PYL receptor partial agonist.

In some embodiments, the second active compound is selected from the group quinabactin, racemic ABA, R-ABA, or S-ABA. In some embodiments, the second active compound is selected from the group benoxacor, benzothiadiazole, dichlorobenil, fludioxonil, or mandipropamid. In some embodiments, the second active compound is set forth in U.S. Pat. Publ. No. 2010/0216643 or 2013/0324409, which are incorporated by reference herein in their entirety.

III. Application to Plants

In some embodiments, the agricultural chemical formulations contemplated are formulated for contacting to plants. The formulations can be suitable for treating plants or plant propagation material, such as seeds, in accordance with the present invention, e.g., in a carrier. Suitable additives include buffering agents, wetting agents, coating agents, polysaccharides, and abrading agents. Exemplary carriers include water, aqueous solutions, slurries, solids and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal). Any agriculturally suitable carrier known to one skilled in the art would be acceptable and is contemplated for use in the present invention. Optionally, the formulations can also include at least one surfactant, herbicide, fungicide, pesticide, or fertilizer.

In some aspects, the present invention provides a method of reducing transpiration in a plant, the method comprising contacting a plant with a sufficient amount of the compound of compound of Formula I, IB, II, III, IIIB, or IV as set forth herein, thereby reducing transpiration.

In some embodiments, a seed, flower, leaf, fruit, processed food, or food ingredient from a plant as described herein is provided. In some embodiments, the plant is a seed.

In some aspects, the present invention provides a method of activating a PYR/PYL protein, the method comprising contacting the PYR/PYL protein with a compound as set forth herein (e.g., a compound of Formula I). In some embodiments, the method comprises contacting the PYR/PYL protein with a formulation comprising a compound of Formula I, IB, II, III, IIIB, or IV. In some embodiments, the PYR/PYL protein is selectively activated. In some embodiments, the PYR/PYL protein is expressed by a cell. In a further embodiment, the cell is a plant cell. In some embodiments, the PYR/PYL protein is PYL-5. In some alternative embodiments, the PRY/PYL protein is PYL-8. In some alternative embodiments, the PYR/PYL protein is PYL-9.

Contacting the agricultural chemical formulation to the PYR/PYL receptor polypeptide can be performed in vitro (e.g., wherein the PYR/PYL receptor polypeptide exists in a purified form or is expressed in yeast cells) or in vivo (e.g., wherein the PYR/PYL receptor polypeptide is expressed by a plant). Contacting the agricultural chemical formulation to the PYR/PYL receptor polypeptide in vitro can be performed using a variety of known methods, e.g., by applying the formulation to protein binding assays, mammalian or yeast two-hybrid assays, competition assays, or cell-based assays using other organisms.

Contacting the agricultural chemical formulation to the PYR/PYL receptor polypeptide in vivo (e.g., to a plant) can be performed using a variety of known methods, e.g., by spraying, atomizing, dusting or scattering the formulations over the propagation material or brushing or pouring or otherwise contacting the formulations over the plant or, in the event of seed, by coating, encapsulating, or otherwise treating the seed. In an alternative to directly treating a plant or seed before planting, the formulations of the invention can also be introduced into the soil or other media into which the seed is to be planted. In some embodiments, a carrier is also used in this embodiment. The carrier can be solid or liquid, as noted above. In some embodiments peat is suspended in water as a carrier of the chemical agonist, and this mixture is sprayed into the soil or planting media or over the seed as it is planted.

The ABA agonist compounds or formulations can be applied to plants using a variety of known methods, e.g., by spraying, atomizing, dipping, pouring, irrigating, dusting or scattering the formulations over the propagation material, or brushing or pouring or otherwise contacting the formulations over the plant or, in the event of seed, by coating, encapsulating, spraying, dipping, immersing the seed in a liquid formulation, or otherwise treating the seed. In an alternative to directly treating a plant or seed before planting, the formulations of the invention can also be introduced into the soil or other media into which the seed is to be planted. For example, the formulations can be introduced into the soil by spraying, scattering, pouring, irrigating or otherwise treating the soil. In some embodiments, a carrier is also used in this embodiment. The carrier can be solid or liquid, as noted above.

In some embodiments peat is suspended in water as a carrier of the ABA agonist, and this mixture is sprayed into the soil or planting media or over the seed as it is planted.

The types of plant that can be treated with the ABA agonists described herein include both monocotyledonous (i.e., monocot) and dicotyledonous (i.e., dicot) plant species including cereals such as barley, rye, sorghum, tritcale, oats, rice, wheat, soybean and corn; beets (for example sugar beet and fodder beet); cucurbits including cucumber, muskmelon, cantaloupe, squash and watermelon; cole crops including broccoli, cabbage, cauliflower, bok choi, and other leafy greens, other vegetables including tomato, pepper, lettuce, beans, pea, onion, garlic and peanut; oil crops including canola, peanut, sunflower, rape, and soybean; solanaceous plants including tobacco; tuber and root crops including potato, yam, radish, beets, carrots and sweet potatoes; fruits including strawberry; fiber crops including cotton and hemp; other plants including coffee, bedding plants, perennials, woody ornamentals, turf and cut flowers including carnation and roses; sugar cane; containerized tree crops; evergreen trees including fir and pine; deciduous trees including maple and oak; and fruit and nut trees including cherry, apple, pear, almond, peach, walnut and citrus.

It will be understood that the ABA agonists described herein mimic the function of ABA on cells. Thus, it is expected that one or more cellular responses triggered by contacting the cell with ABA will also be triggered be contacting the cell with the ABA agonists described herein. The ABA agonists described herein mimic the function of ABA and are provided in a useful formulation.

In some embodiments, application of the ABA agonists described herein increases the abiotic stress resistance of a plant.

In some embodiments, application of the ABA agonists described herein to seeds inhibits germination of the seeds.

The present invention also provides plants in contact with the ABA formulations described herein. The plant in contact with the ABA formulation can include a plant part or a seed.

IV. Testing ABA Agonists and Antagonists

Embodiments of the present invention also provide for methods of screening putative chemical agonists to determine whether the putative agonist agonizes a PYR/PYL receptor polypeptide, when the putative agonist is contacted to the PYR/PYL receptor polypeptide. As used herein, an agent "agonizes" a PYR/PYL receptor protein if the presence of the agent results in activation or up-regulation of activity of the receptor, e.g., to increase downstream signaling from the PYR/PYL receptor. For the present invention, an agent agonizes a PYR/PYL receptor if, when the agent is present at a concentration no greater than 200 μM, contacting the agent to the PYR/PYL receptor results in activation or up-regulation of the activity of the PYR/PYL receptor as indicated by a substantial decrease in PP2C activity if measured in vitro, or induction of an ABA-regulated marker gene, or other physiological response (e.g., guard cell closure), if measured in vivo. If an agent does not activate a PYR/PYL receptor protein's activity when the agent is present at a concentration no greater than 200 μM, then the agent does not significantly agonize the PYR/PYL receptor. As used herein, "activation" requires a minimum threshold of activity to be induced by the agent. Determining whether this minimum threshold of activity has been met can be accomplished, e.g., by using an enzymatic phosphatase assay that sets a minimum value for the level of enzymatic activity that must be induced, or by using an enzymatic phosphatase assay in the presence of a colorimetric detection reagent (e.g., para-nitrophenylphosphate) wherein the minimum threshold of activity has been met if a color change is observed.

The present invention also provides methods of screening for ABA agonists and antagonists by screening for a molecule's ability to induce PYR/PYL-PP2C binding in the case of agonists, or to disrupt the ability of ABA and other agonists to promote PYR/PYL-PP2C binding in the case of antagonists. A number of different screening protocols can be utilized to identify agents that agonize or antagonize a PYR/PYL polypeptide.

Screening can take place using isolated, purified or partially purified reagents. In some embodiments, purified or partially purified PYR/PYL polypeptide can be used.

Alternatively, cell-based methods of screening can be used. For example, cells that naturally-express a PYR/PYL polypeptide or that recombinantly express a PYR/PYL polypeptide can be used. In some embodiments, the cells used are plant cells, animal cells, bacterial cells, fungal cells, including but not limited to yeast cells, insect cells, or mammalian cells. In general terms, the screening methods involve screening a plurality of agents to identify an agent that modulates the activity of a PYR/PYL polypeptide by, e.g., binding to PYR/PYL polypeptide, or activating a PYR/PYL polypeptide or increasing expression of a PYR/PYL polypeptide, or a transcript encoding a PYR/PYL polypeptide.

1. PYR/PYL Polypeptide Binding Assays

Optionally, preliminary screens can be conducted by screening for agents capable of binding to a PYR/PYL polypeptide, as at least some of the agents so identified are likely PYR/PYL polypeptide modulators.

Binding assays can involve contacting a PYR/PYL polypeptide with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89). Other binding assays involve the use of mass spectrometry or NMR techniques to identify molecules bound to PYR/PYL polypeptide or displacement of labeled substrates (e.g., labeled ABA). The PYR/PYL polypeptide protein utilized in such assays can be naturally expressed, cloned or synthesized.

2. Activity

PYR/PYL polypeptide agonists can be identified by screening for agents that activate or increase activity of a PYR/PYL polypeptide. Antagonists can be identified by their reducing activity.

One activity assay involves testing whether a candidate agonist can induce binding of a PYR/PYL protein to a type 2 protein phosphatase (PP2C) polypeptide in an agonist-specific fashion. Mammalian or yeast two-hybrid approaches (see, e.g., Bartel, P. L. et. al. *Methods Enzymol*, 254:241 (1995)) can be used to identify polypeptides or other molecules that interact or bind when expressed together in a cell. In some embodiments, agents that agonize a PYR/PYL polypeptide are identified in a two-hybrid assay between a PYR/PYL polypeptide and a type 2 protein phosphatase (PP2C) polypeptide (e.g., ABI1 or 2 or homologs thereof, e.g., from the group A subfamily of PP2Cs), wherein an ABA agonist is identified as an agent that activates or enables binding of the PYR/PYL polypeptide and the PP2C polypeptide. Thus, the two polypeptides bind in the presence, but not in the absence of the agent. In some embodiments, a chemical compound or agent is identified as an agonist of a PYR/PYL protein if the yeast cell turns blue in the yeast two hybrid assay.

The biochemical function of PYR1, and PYR/PYL proteins in general, is to inhibit PP2C activity. This can be measured in live cells using the yeast two hybrid or other cell-based methods. It can also be measured in vitro using enzymatic phosphatase assays in the presence of a colorimetric detection reagent (for example, para-nitrophenyl-phosphate). The yeast-based assay used above provides an indirect indicator of ligand binding. To address this potential limitation, one can use in vitro receptor-mediated phosphatase inhibition assays, or cell-based assays using other organisms, as alternative approaches for identifying weak binding target compounds.

3. Expression Assays

Screening for a compound that increases the expression of a PYR/PYL polypeptide is also provided. Screening methods generally involve conducting cell-based or plant-based assays in which test compounds are contacted with one or more cells expressing PYR/PYL polypeptide, and then detecting an increase in PYR/PYL expression (either transcript or translation product). Assays can be performed with cells that naturally express PYR/PYL or in cells recombinantly altered to express PYR/PYL, or in cells recombinantly altered to express a reporter gene under the control of the PYR/PYL promoter.

Various controls can be conducted to ensure that an observed activity is authentic, including running parallel reactions with cells that lack the reporter construct or by not contacting a cell harboring the reporter construct with test compound.

4. Validation

Agents that are initially identified by any of the foregoing screening methods can be further tested to validate the apparent activity or determine other biological effects of the agent. In some cases, the identified agent is tested for the ability to effect plant stress (e.g., drought tolerance), seed germination, or another phenotype affected by ABA. A number of such assays and phenotypes are known in the art and can be employed according to the methods of the invention.

5. Solid Phase and Soluble High-Throughput Assays

In the high-throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

The molecule of interest (e.g., PYR/PYL or a cell expressing a PYR/PYL polypeptide) can be bound to the solid-state component, directly or indirectly, via covalent or non-covalent linkage.

The invention provides in vitro assays for identifying, in a high-throughput format, compounds that can modulate the expression or activity of PYR/PYL.

Abiotic stress resistance can be assayed according to any of a number of well-known techniques. For example, for drought tolerance, plants can be grown under conditions in which less than optimum water is provided to the plant. Drought resistance can be determined by any of a number of standard measures including turgor pressure, growth, yield, and the like.

V. Methods of Increasing Abiotic Stress Tolerance in Plants

The present invention also provides methods of increasing abiotic stress tolerance in a plant. Thus, in some embodiments, a plant is contacted with an ABA agonist compound as set forth herein, or an ABA agonist formulation as set forth herein, in sufficient amount to increase the abiotic stress tolerance in the plant. The amount of the ABA agonist compound or formulation applied to the plant can be sufficient to increase the abiotic stress tolerance compared to not contacting the plant with the ABA agonist compound or formulation. The plant can be contacted with the ABA agonist compound or formulation using any of the methods described herein. The increase in abiotic stress tolerance can improve the plants growth or survival to abiotic stress conditions that adversely affect the plant's growth or survival. Abiotic stress includes physical or chemical conditions described herein.

In some embodiments, the plant is a monocot. In some alternative embodiments, the plant is a dicot. In some embodiments, the abiotic stress tolerance comprises drought tolerance.

In some embodiments, the contacting step comprises delivering the formulation to the plant by aircraft or irrigation.

VI. Methods of Inhibiting Seed Germination in a Plant

The present invention also provides methods of inhibiting seed germination. Thus, in some embodiments, a plant, plant part, or a seed is contacted with an ABA agonist formulation in an amount sufficient to inhibit seed germination. The seed can be contacted with the ABA formulation using any of the methods described herein. In some embodiments, the seed is directly contacted with the ABA agonist formulation. In some embodiments, the ground or soil is contacted with the ABA agonist formulation either prior to or after planting or sowing the seeds. In some embodiments, a plant is contacted with sufficient ABA agonist formulation to inhibit germination of seeds that later develop from the plant. In some aspects, the present invention provides a method of inhibiting seed germination in a plant, the method comprising contacting a seed with a sufficient amount of the compound or formulation as set forth herein, thereby inhibiting germination.

VII. Methods of Activating a PYR/PYL Receptor Protein

The present invention also provides methods of activating a PYR/PYL receptor protein. In some embodiments, a PYR/PYL protein is contacted with a compound or formulation set forth herein. In some embodiments, the activated PYR/PYL protein binds to a PP2C polypeptide. In some embodiments, the PYR/PYL protein that is activated is substantially identical to any one of SEQ ID NOs:1-119. Examples of sequences of ABA receptors from various plants are provided in U.S. Patent Publication 2011/0271408, which is incorporated by reference herein in its entirety.

In some embodiments, the PYR/PYL protein is an endogenous protein. In some embodiments, the PYR/PYL protein is a heterologous protein. In some embodiments, the cell further expresses a type 2 protein phosphatase (PP2C). In some embodiments, the type 2 protein phosphatase is HAB1 (Homology to ABI1), ABI1 (Abscisic acid insensitive 1), or ABI2 (Abscisic acid insensitive 2).

In some embodiments, the PYR/PYL protein is expressed by a cell. In some embodiments, the cell is a plant cell. In some alternative embodiments, the cell is a plant, animal, mammalian, or fungal cell.

In some embodiments, the method activates a PYR/PYL receptor in a cell free in vitro assay. In some embodiments, the method activates a PYR/PYL receptor expressed in a cell. In some embodiments, the cell also expresses a PP2C polypeptide. In some embodiments, the cell is a plant cell. In some embodiments, the cell is an animal or mammalian cell. In some embodiments, the cell expresses an endogenous PYR/PYL protein. In some embodiments, the cell is engineered to express a heterologous PYR/PYL polypeptide. In some embodiments, the cell expresses a heterologous PP2C polypeptide. In some embodiments, the cell expresses a PP2C polypeptide selected from HAB1 (homology to ABI1), ABI1, or ABI2.

In some embodiments, the activated PYR/PYL polypeptide induces expression of heterologous genes. In some embodiments, the heterologous genes are ABA responsive genes. In some embodiments, the induced gene expression occurs in cells that express an endogenous PYR/PYL polypeptide. In some embodiments, the induced gene expression occurs in cells that express a heterologous PYR/PYL polypeptide.

It is understood that the examples and embodiments described herein are for illustrative purposes only. Various modifications or changes in light thereof will be suggested to persons skilled in the art and are to be included within the spirit and purview of this application and the scope of the appended claims. All publications, sequence accession numbers, patents, and patent applications cited herein are hereby incorporated by reference in their entirety for all purposes.

EXAMPLES

Example 1

ABA Activity of N-Acylsulfonamide Derivatives

1. N-Acylsulfonamide agonists of Monomeric Receptor Activity

A family of 62 structurally related N-acyl sulfonamides (Tables I-V) were tested for ABA agonist activity using multiple receptor-mediated PP2C inhibition in vitro assays (Park et al., 2009). Recombinant proteins for all *Arabidopsis* receptors were prepared, with the exceptions of PYL7 and PYL12, which failed to yield active proteins. The constructs utilized for protein expression have been previously described (Okamoto et al. 2013). For constructs encoding 6X-His-fusion proteins (all receptors except PYL11), the coding sequences were of the receptors were cloned in the vector pET28, expressed in BL21[DE3]pLysS *E. coli* host cells at 18° C. overnight, and subsequently purified from sonicated lysates using Ni-NTA agarose (Qiagen, USA), according to the manufacturer's instructions. PYL11 was constructed as a maltose binding protein fusion in the vector pMAL-c, expressed in BL21[DE3]pLysS host cells and purified using amylose resin (New England Biolabs) as described by the manufacturer. Recombinant GST-HAB1 was expressed and purified as described previously (Park et al., 2009). PP2C activity assays were conducted using the fluorogenic phosphatase substrate 4-methylumbelliferyl-phosphate. Recombinant receptors and HAB1 were used to examine ligand-induced PP2C inactivation in response to multiple test compounds. Enzyme inhibition assays were conducted using the following assay conditions: 50 nM GST-PP2C, 100 mM Tris-OAc (pH 7.9), 100 mM NaCl, 1 mM $MnCl_2$, 1% β-mercaptoethanol. The activity of recombinant ABA receptors dropped rapidly in the 24-48 hours after purification and then stabilized, suggesting inactivation of a subset of the receptors after purification. Because of this, the ratio of each receptor used in the PP2C-inhibitions assays was established empirically as the minimum fold-excess of receptor required to elicit maximal PP2C inhibition at a saturating ABA concentration (10 µM).

Based on this criterion, we used a ratio of 2:1 receptor in the assays described herein.

Using the above assay conditions, compounds were tested at 25 µM for agonist activity on PYL4, PYL5, PYL8 and PYL9. As shown in Table VI, most of the compounds tested showed activity on at least one of the receptors tested. Consequently, a subset of the compounds was tested at multiple concentrations against 11 receptors so that $IC_{50}$ values and receptor selectivity profiles could be examined. As shown in Table VII, these assays revealed many compounds with nanomolar $IC_{50}$ values (shown in bold in Table VII); thus, the N-acylsulfonamide agonists disclosed include potent activators of monomeric ABA receptors. Importantly, none of the compounds tested appreciably activated dimeric ABA receptors (i.e., none possessed $IC_{50}$ values less than 50 µM). Thus, the N-acylsulfonamide agonists disclosed are selective for monomeric receptors.

The tricyclic N-acylsulfonaimdes shown in Table II incorporated rings into the alpha carbon of their phenacyl substructures (position n in Table II). Compounds with cyclopropyl rings (n=3) provided potent and relatively selective PYL5 agonists (i.e., compounds 30, 50 and 44). Moreover, compounds incorporating five- and six-membered rings into the same position provided potent and relatively selective PYL9 agonists (i.e., compounds 51 and 24). These data define the alpha carbon as a valuable site for controlling both agonist selectivity and potency.

2. N-Acylsulfonamides Regulate ABA Signaling in Planta

To examine if the agonists identified possess bioactivity in vivo, we examined the effects of several compounds on *Arabidopsis* seed germination and hypocotyl growth. We germinated seeds from wild type on ½× strength Murashige and Skoog salts growth medium containing either 10 or 50 µM for all 62 compounds as well as 1 µM (+)-ABA and mock controls. As shown in Table VIII, 41 of the 62 compounds tested inhibit seed germination or hypocotyl growth, as expected of ABA agonists. To investigate if the any of the compounds are sufficient to control vegetative ABA responses, we treated three week old *Arabidopsis* plants with aqueous solutions containing 0.02% Silwet and either 50 μM of selected N-acylsulfonamides, 50 μM ABA or 0.1% DMSO (the carrier solvent for the compounds tested). The leaf temperatures were subsequently examined using a thermal imaging camera 24 hours after treatment. It is well known that ABA-induced guard cell closure reduces transpiration, which leads to increases in leaf temperatures. It has been estimated that a 1° C. increase in leaf temperature correlates with a decrease in transpiration rates by approximately 50% (Sirault et al., 2009). Since guard cell aperture is the primary determinant of transpiration rates, thermal imaging is a useful way to indirectly infer relative transpiration rates and, indirectly, relative degrees of guard cell opening at the whole plant level. As shown in Table IX, several N-acylsulfonamides altered leaf temperature within 24 hours of treatment, indicating they reduced transpiration by inducing guard cell closure, as expected for ABA agonists. These biological data indicate broad potency of the N-acylsulfonamide agonist family in vivo.

TABLE I

Exemplary Structures

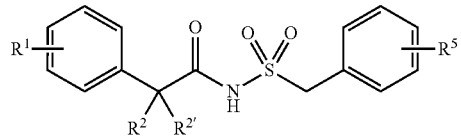

| Cmpd. No. | $R^1$ | $R^2$ | $R^{2'}$ | $R^5$ |
|---|---|---|---|---|
| 1 | H | Me | Me | 2-CN |
| 2 | 4-Br | Me | Me | 4-CN |
| 3 | H | Me | Me | 4-NO$_2$ |
| 4 | H | Me | Me | 4-F |
| 5 | H | Me | Me | H |
| 6 | 4-Cl | Me | Me | 4-CN |
| 7 | 3,4-dichloro | Me | Me | 4-CN |
| 8 | 2-F | Me | Me | 4-CN |
| 9 | 3-Br | Me | Me | 4-CN |
| 10 | 4-Cl | Et | Et | 4-CN |
| 11 | 4-CF$_3$ | Me | Me | 4-CN |
| 12 | 4-Me | Me | Me | 4-CN |
| 13 | 4-F | Me | Me | 4-CN |
| 14 | 4-isobutoxy | Me | Me | 4-CN |
| 15 | 3-Cl | Me | Me | 4-CN |
| 16 | 3-F | Me | Me | 4-CN |
| 17 | H | Et | Et | 2-CN |
| 18 | 3-cyano | Me | Me | 4-CN |
| 19 | H | Et | Et | 4-NO$_2$ |
| 20 | 4-Et | Me | Me | 4-CN |
| 21 | 3,4-dimethoxy | Me | Me | 4-CN |

TABLE I-continued

Exemplary Structures

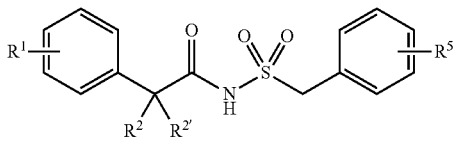

| Cmpd. No. | $R^1$ | $R^2$ | $R^{2'}$ | $R^5$ |
|---|---|---|---|---|
| 22 | 4-methoxy | Me | Me | 4-CN |
| 23 | H | Me | Me | 4-CN |

TABLE II

Exemplary Structures

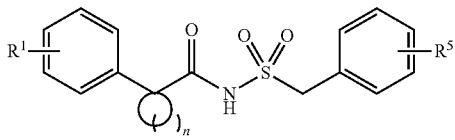

| Cmpd. No. | $R^1$ | n | $R^5$ |
|---|---|---|---|
| 24 | 4-F | 5 | 4-CN |
| 25 | 2-F | 5 | 4-CN |
| 26 | 3-F | 5 | 4-CN |
| 27 | H | 3 | 4-CN |
| 28 | 4-Cl | 4 | 4-CN |
| 29 | H | 4 | 4-CN |
| 30 | 4-Br | 3 | 4-CN |
| 31 | 4-Br | 4 | 4-CN |
| 32 | 4-F | 4 | 4-CN |
| 33 | 3-F | 4 | 4-CN |
| 34 | 4-t-Bu | 3 | 4-CN |
| 35 | 4-F | 3 | 4-CN |
| 36 | 3,5-dimethyl | 3 | 4-CN |
| 37 | H | 2 | 4-NO$_2$ |
| 38 | 3-Me | 3 | 4-CN |
| 39 | 4-methoxy | 5 | 4-CN |
| 40 | 4-t-Bu | 3 | 4-CN |
| 41 | 2-methoxy | 3 | 4-CN |
| 42 | 2-methoxy | 4 | 4-CN |
| 43 | 3-Me | 5 | 4-CN |
| 44 | 2-Me | 3 | 4-CN |
| 45 | 4-CF$_3$ | 3 | 4-CN |
| 46 | 3-F | 3 | 4-CN |
| 47 | 2-F | 3 | 4-CN |
| 48 | 4-CF$_3$ | 4 | 4-CN |
| 49 | 3,4-dichloro | 4 | 4-CN |
| 50 | 3-CN | 3 | 4-CN |
| 51 | 4-F | 6 | 4-CN |
| 52 | 4-OEt | 3 | 4-CN |

TABLE III

Exemplary Structures

| Cmpd. No. | $R^A$ | $R^2$ | $R^{2'}$ | $R^B$ |
|---|---|---|---|---|
| 53 | 2,3-dihydro-1,4-benzodioxin-6-yl | Me | Me | 4-cyanobenzyl |
| 54 | 2-naphthyl | Me | Me | 4-cyanobenzyl |
| 55 | Ph | Me | Me | quinolin-7-ylmethyl |

TABLE IV

Exemplary Structures

| Cmpd. No. | $R^1$ | X | Y | $R^5$ |
|---|---|---|---|---|
| 56 | H | N | COCH$_3$ | 4-CN |
| 57 | 3-F | O | — | 4-CN |
| 58 | 3-Cl | O | — | 4-CN |
| 59 | 4-CF$_3$ | O | — | 4-CN |
| 60 | H | N | SO$_2$Ph | 4-CN |

TABLE V

Exemplary Structures

| Cmpd. No. | Structure |
|---|---|
| 61 | (4-cyanobenzyl sulfonamide of 1-methyl-1,2,3,4-tetrahydronaphthalene-1-carboxylic acid) |
| 62 | (1-phenylcyclopropane-1-carboxylic acid N-(quinolin-8-ylmethylsulfonyl)amide) |

TABLE VI

PP2C Activity (25 μm)

| Cmpd. No. | PYL4 | PYL5 | PYL8 | PYL9 |
|---|---|---|---|---|
| 1 | 96 | 106 | 89 | 83 |
| 24 | 92 | 99 | 21 | 10 |
| 25 | 94 | 102 | 37 | 21 |
| 26 | 99 | 105 | 33 | 18 |
| 27 | 97 | 39 | 77 | 63 |
| 56 | 94 | 105 | 106 | 108 |
| 28 | 96 | 65 | 55 | 37 |
| 29 | 96 | 90 | 28 | 14 |
| 30 | 90 | 12 | 82 | 69 |
| 31 | 97 | 77 | 80 | 74 |
| 32 | 92 | 74 | 24 | 12 |
| 33 | 98 | 81 | 39 | 24 |
| 34 | 95 | 99 | 103 | 107 |
| 35 | 94 | 20 | 62 | 49 |
| 2 | 89 | 23 | 69 | 47 |
| 36 | 91 | 34 | 98 | 94 |
| 37 | 84 | 30 | 78 | 60 |
| 3 | 90 | 47 | 35 | 18 |
| 4 | 97 | 106 | 59 | 36 |
| 5 | 89 | 86 | 83 | 61 |
| 6 | 90 | 21 | 52 | 32 |
| 57 | 91 | 100 | 56 | 39 |
| 38 | 92 | 41 | 77 | 66 |
| 58 | 96 | 83 | 84 | 83 |
| 59 | 92 | 65 | 97 | 98 |
| 39 | 98 | 110 | 71 | 66 |
| 53 | 89 | 95 | 99 | 98 |

TABLE VI-continued

| PP2C Activity (25 μm) | | | | |
|---|---|---|---|---|
| Cmpd. No. | PYL4 | PYL5 | PYL8 | PYL9 |
| 7 | 90 | 33 | 54 | 38 |
| 40 | 92 | 101 | 106 | 103 |
| 41 | 93 | 27 | 89 | 81 |
| 42 | 88 | 45 | 65 | 42 |
| 8 | 91 | 41 | 77 | 69 |
| 61 | 91 | 16 | 75 | 68 |
| 9 | 91 | 43 | 58 | 47 |
| 43 | 95 | 95 | 41 | 46 |
| 10 | 93 | 75 | 83 | 73 |
| 44 | 89 | 18 | 63 | 50 |
| 11 | 93 | 44 | 62 | 58 |
| 45 | 93 | 30 | 74 | 53 |
| 12 | 92 | 43 | 62 | 47 |
| 13 | 98 | 37 | 32 | 17 |
| 14 | 97 | 103 | 108 | 108 |
| 46 | 95 | 24 | 73 | 55 |
| 47 | 95 | 28 | 86 | 75 |
| 15 | 96 | 51 | 57 | 46 |
| 16 | 93 | 47 | 43 | 30 |
| 17 | 85 | 96 | 95 | 94 |
| 18 | 91 | 12 | 52 | 34 |
| 54 | 97 | 68 | 106 | 109 |
| 48 | 93 | 76 | 60 | 59 |
| 19 | 86 | 85 | 36 | 15 |
| 20 | 95 | 88 | 104 | 98 |
| 49 | 92 | 77 | 93 | 81 |
| 21 | 89 | 89 | 98 | 102 |
| 22 | 95 | 85 | 91 | 92 |
| 50 | 67 | 7 | 36 | 18 |
| 51 | 93 | 97 | 16 | 8 |
| 52 | 94 | 99 | 91 | 98 |
| 62 | 98 | 103 | 100 | 100 |
| 55 | 96 | 95 | 72 | 49 |
| 60 | 90 | 70 | 101 | 101 |
| 23 | ND | ND | ND | ND |

TABLE VIII

| Germination Effects | | |
|---|---|---|
| Compound No. | Germination Inhibition | Hypocotyl Growth Inhibition |
| Mock | – | – |
| ABA | 1 | |
| 1 | – | 50 |
| 24 | 10 | |
| 25 | 50 | 10 |
| 26 | 50 | 10 |
| 27 | – | 50 |
| 56 | – | – |
| 28 | – | 10 |
| 29 | 50 | 10 |
| 30 | – | 50 |
| 31 | – | – |
| 32 | 50 | 10 |
| 33 | – | 10 |
| 34 | 50 | |
| 35 | – | 10 |
| 2 | 50 | 10 |
| 36 | – | – |
| 37 | – | 50 |
| 3 | 50 | 10 |
| 4 | – | 50 |
| 5 | – | 50 |
| 6 | 50 | 10 |
| 57 | – | – |
| 38 | – | 50 |
| 58 | – | – |
| 59 | – | – |
| 39 | 50 | 10 |
| 53 | – | 50 |
| 7 | 50 | 10 |
| 40 | – | – |
| 41 | – | 10 |
| 42 | 50 | 10 |
| 8 | 50 | 10 |
| 61 | – | 50 |
| 9 | – | 10 |

TABLE VII

| PP2C Dose Curves | | | | | | | | | | | |
|---|---|---|---|---|---|---|---|---|---|---|---|
| Cmpd. No. | PYR1 | PYL1 | PYL2 | PYL3 | PYL4 | PYL5 | PYL6 | PYL8 | PYL9 | PYL10 | PYL11 |
| 24 | >50 | >50 | — | — | >50 | >50 | >50 | 6.38 | 0.60 | 14.77 | 4.09 |
| 25 | — | — | — | — | — | — | — | 12.56 | 6.69 | >50 | 12.71 |
| 26 | — | — | — | — | — | — | — | 11.51 | 7.11 | 41.60 | 7.52 |
| 29 | — | — | — | — | — | >50 | >50 | 3.36 | 1.27 | >50 | 1.77 |
| 30 | — | — | >50 | >50 | — | 0.86 | >50 | >50 | >50 | — | 4.63 |
| 32 | — | — | — | — | — | >50 | >50 | 3.23 | 1.40 | >50 | 2.25 |
| 35 | — | — | — | — | — | 3.91 | 34.70 | >50 | 27.18 | >50 | 3.29 |
| 3 | — | — | — | — | — | 29.51 | 45.53 | 8.58 | 3.00 | — | 1.94 |
| 6 | — | — | >50 | — | — | >50 | >50 | 26.28 | 8.96 | >50 | 4.16 |
| 7 | — | — | >50 | — | — | 10.71 | >50 | 40.04 | 18.45 | — | 13.95 |
| 42 | — | — | — | — | — | 29.40 | >50 | 52.41 | 17.39 | 17.89 | 14.70 |
| 43 | — | — | — | — | — | — | — | 22.69 | 28.24 | >50 | >50 |
| 44 | — | — | >50 | — | — | 2.48 | 12.17 | 49.47 | 21.15 | 79.12 | 13.26 |
| 13 | — | — | >50 | — | — | 11.09 | 18.92 | 4.45 | 1.62 | >50 | 2.48 |
| 46 | — | — | — | — | — | 7.06 | 15.27 | 111.47 | 39.62 | — | 18.51 |
| 18 | — | — | >50 | >50 | >50 | 1.95 | 12.60 | 18.61 | 8.29 | 31.48 | 14.92 |
| 19 | >50 | >50 | >50 | >50 | >50 | >50 | 57.13 | 9.65 | 3.90 | 50.83 | 2.44 |
| 50 | — | — | 54.71 | 20.84 | >50 | 0.39 | 2.43 | 8.39 | 5.76 | >50 | 2.52 |
| 51 | — | — | — | — | — | >50 | >50 | 1.11 | 0.04 | 4.46 | 5.33 |
| 23 | — | — | — | — | — | 39.63 | >50 | 48.92 | 1.88 | >50 | 7.84 |

TABLE VIII-continued

Germination Effects

| Compound No. | Germination Inhibition | Hypocotyl Growth Inhibition |
|---|---|---|
| 43 | 50 | 10 |
| 10 | – | 50 |
| 44 | – | 50 |
| 11 | – | – |
| 45 | – | – |
| 12 | – | 50 |
| 13 | 10 | 10 |
| 14 | – | – |
| 46 | – | – |
| 47 | – | – |
| 15 | – | 10 |
| 16 | 50 | 10 |
| 17 | – | 50 |
| 18 | – | – |
| 54 | – | 50 |
| 48 | | 50 |
| 19 | 10 | |
| 20 | – | – |
| 49 | – | – |
| 21 | – | – |
| 22 | – | 10 |
| 50 | – | |
| 51 | 10 | |
| 52 | – | – |
| 62 | – | – |
| 55 | – | – |
| 60 | – | – |
| 23 | 50 | 10 |

TABLE IX

Thermal Response

| Compound No. | Thermal Response |
|---|---|
| Mock | – |
| ABA | ++++ |
| 29 | +++ |
| 30 | + |
| 32 | +++ |
| 35 | – |
| 13 | +++ |
| 18 | ++ |
| 50 | + |
| 51 | + |

Example 2

Synthesis of N-Acylsulfonamide Derivatives and N-Sulfonylcarbamate Derivatives Schemes 1 and 2 below show the general route for the preparation of N-acylsulfonamide and N-sulfonyl carbamate derivatives. A series of exemplary derivatives are set forth in Tables X and XI.

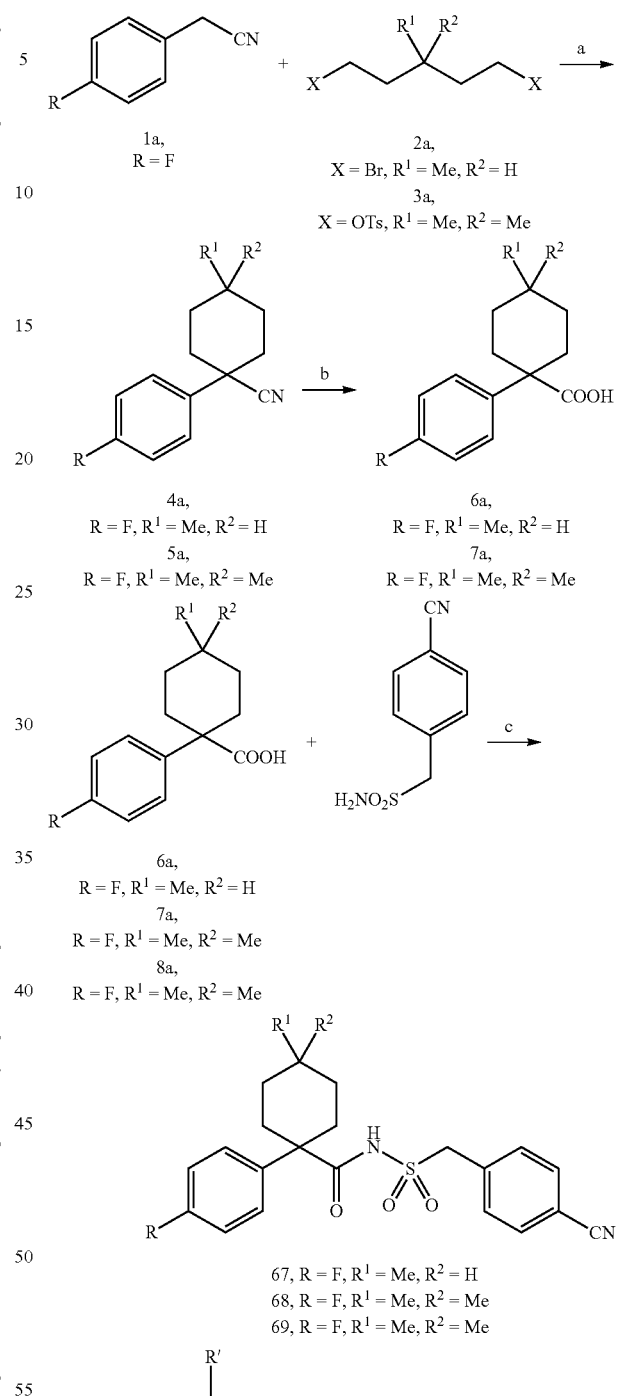

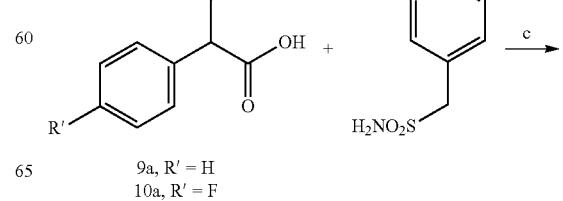

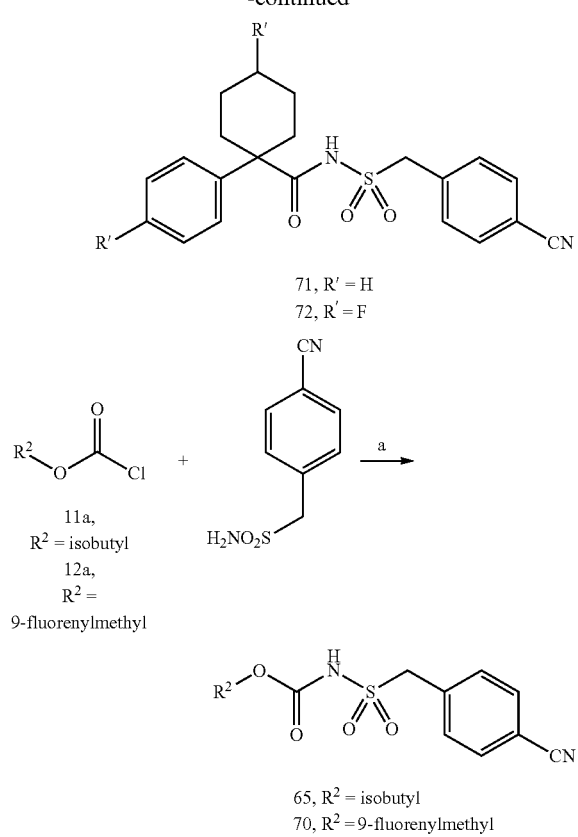

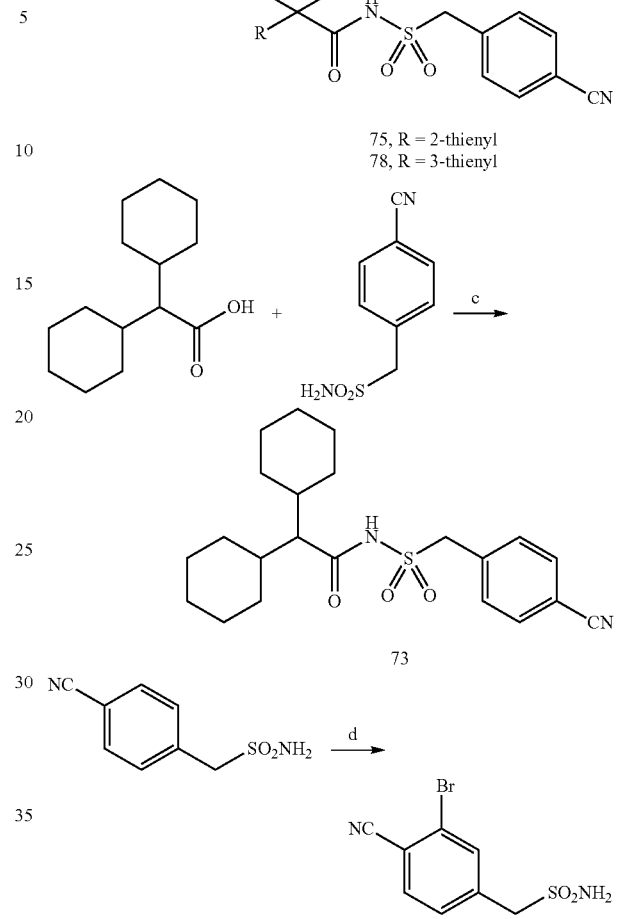

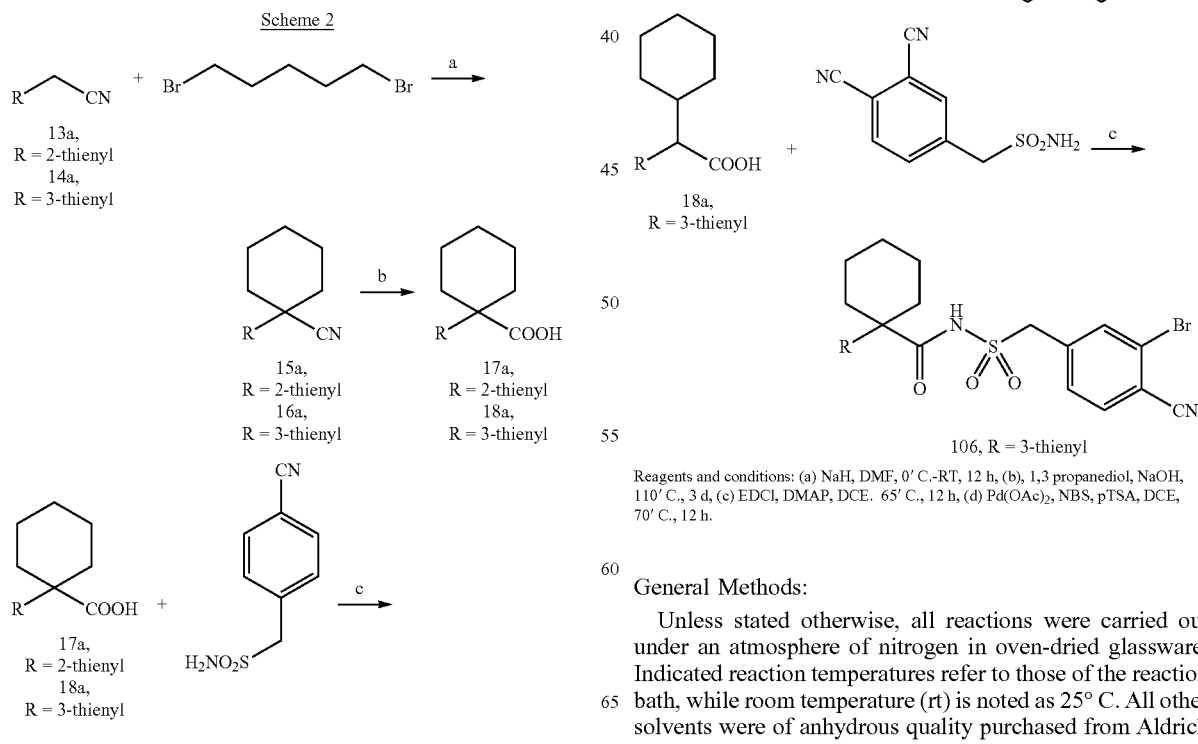

Reagents and Conditions: (a) NaH, DMF, 0' C.-RT, 12 h, (b), 1,3 propanediol, NaOH, 110' C., 3 d, (c) EDCl, DMAP, DCE, 65' C., 12 h.

Reagents and conditions: (a) NaH, DMF, 0' C.-RT, 12 h, (b), 1,3 propanediol, NaOH, 110' C., 3 d, (c) EDCl, DMAP, DCE. 65' C., 12 h, (d) Pd(OAc)$_2$, NBS, pTSA, DCE, 70' C., 12 h.

General Methods:

Unless stated otherwise, all reactions were carried out under an atmosphere of nitrogen in oven-dried glassware. Indicated reaction temperatures refer to those of the reaction bath, while room temperature (rt) is noted as 25° C. All other solvents were of anhydrous quality purchased from Aldrich Chemical Co. and used as received. Pure reaction products were typically dried under high vacuum. Commercially available starting materials and reagents were purchased from Aldrich, TCI and Fisher Scientific and were used as received unless specified otherwise. Analytical thin layer chromatography (TLC) was performed with (5×20 cm, 60 Å, 250 µm). Visualization was accomplished using a 254 nm UV lamp. $^1$H NMR spectra were recorded on Inova 400 MHz spectrophotometer. Chemical shifts are reported in ppm with the solvent resonance as internal standard ([CDCl$_3$ 7.27 ppm, 77.23 ppm] [DMSO-d$_6$ 2.5 ppm, 39.51 ppm] and [MeODd$_4$ 4.78, 49.0] for $^1$H, $^{13}$C respectively). Data are reported as follows: chemical shift, multiplicity (s=singlet, d=doublet, dd=doublet of doublet, t=triplet, q=quartet, br=broad, m=multiplet, abq=ab quartet), number of protons, and coupling constants. High resolution mass spectral data was collected using a Agilent 6224 LC-TOF. All compounds submitted for biological testing were found to be ≥95% pure.

1-(4-Fluorophenyl)-4-methylcyclohexanecarbonitrile (4a). To a solution of 2a (4.8 g, 0.019 mol) and 1a (2.5 g, 0.019 mol) in anhydrous DMF was added NaH (1.85 g, 0.046 mol) portion wise at 0° C. and the reaction allowed to attain room temperature and stirred for 12 h. The reaction was quenched with water and extracted with EtOAc (3×30 mL). The combined organic extracts were washed with brine, dried (Na$_2$SO$_4$), filtered, and concentrated under reduced pressure. The crude was purified by flash chromatography (100:0→80:20, hexanes:EtOAc) to a give compound 4a as a pale yellow oil (3.2 g, 80%). $^1$H NMR (400 MHz, CDCl3): δ 7.40-7.48 (m, 2H), 7.01-7.10 (m, 2H), 2.07-2.17 (m, 2H), 1.92-2.02 (m, 2H), 1.77-1.88 (m, 3H), 1.39-1.59 (m, 3H), 0.95-0.93 (m, 3H).

1-(4-Fluorophenyl)-4,4-dimethylcyclohexanecarbonitrile (5a). The synthesis of intermediate 5a is similar to that reported for intermediate 4a, and 5a is obtained as a white solid in 70% yield. $^1$H NMR (400 MHz, CDCl3): δ 7.39-7.51 (m, 2H), 7.02-7.11 (m, 2H), 2.01-1.47 (m, 8H), 1.03 (s, 3H), 0.97 (s, 3H).

1-(Thiophen-2-yl)-1-cyclohexane-1-carbonitrile (15a) The synthesis of intermediate 15a is similar to that reported for intermediate 4a, and 15a is obtained as a yellow oil in 75% yield. $^1$H-NMR (400 MHz, DMSO-d$_6$): δ 7.48-7.54 (m, 1H), 7.13-7.19 (m, 1H), 6.99-7.04 (m, 1H), 2.22 (d, J=12.87 Hz, 2H), 1.8-1.54 (m, 8H).

1-(Thiophen-3-yl)-1-cyclohexane-1-carbonitrile (16a) The synthesis of intermediate 16a is similar to that reported for intermediate 4a, and 16a is obtained as a yellow oil in 88% yield. $^1$H NMR (400 MHz, DMSO-d$_6$): δ 7.54-7.60 (m, 1H), 7.49 (dd, J=2.73, 1.56 Hz, 1H), 7.19-7.26 (m, 1H), 2.07-2.16 (m, 2H), 1.63-1.80 (m, 6H), 1.48-1.63 (m, 2H).

1-(4-Fluorophenyl)-4-methylcyclohexanecarboxylic acid (6a). To a solution of 4a (2 g, 9.2 mmole) in 20 mL of 1,3 propanediol was added freshly powdered NaOH (3.7 g, 92 mmol) and the mixture stirred in a pressure vessel for 3 days at 110° C. Upon completion, the reaction is cooled to room temperature, quenched with concentrated hydrochloric and cooled for an hour at 0° C. to give compound 6a as a white solid (1.5 g, 68%) which is filtered off and used without further purification.

1-(4-Fluorophenyl)-4,4-dimethylcyclohexanecarboxylic acid (7a). The synthesis of intermediate 7a is similar to that reported for intermediate 6a, and 7a is obtained as a white solid in 55% yield.

1-(Thiophen-2-yl)-1-cyclohexane-1-carboxylic acid (17a) The synthesis of intermediate 17a is similar to that reported for intermediate 6a, and 17a is obtained as a white solid in 75% yield.

1-(Thiophen-3-yl)-1-cyclohexane-1-carboxylic acid (18a) The synthesis of intermediate 18a is similar to that reported for intermediate 6a, and 18a is obtained as a white solid in 60% yield.

1-(3-Bromo-4-cyanophenyl)methanesulfonamide. To a suspension of 1-(4-cyanophenyl)-methanesulfonamide (2 g, 0.01 mol) in anhydrous dichloroethane was added N-bromosuccinimide (3.26 g, 0.0183 mol), Pd(OAc)$_2$ (0.228 g, 0.00102 mol) and p-toluenesulfonic acid (1.938 g, 0.0102). The suspension was heated in a sealed pressure vessel at 70'C for 12 h. After cooling to room temperature, the volatiles were removed under pressure, and the residue was purified by flash chromatography chromatography (100:0→10:90, hexanes:EtOAc) to give the brominated sulfonamide as a white solid (2.5 g, 89% yield.). $^1$H NMR (400 MHz, DMSO-d$_6$): 7.98-7.91 (m, 1H), 7.79-7.86 (m, 1H), 7.58-7.50 (m, 1H), 6.93 (s, 2H), 4.34 (s, 2H).

General Procedure for Synthesis of N-Acylsulfonamide Derivatives.

To a solution of acid (1 equiv) was added EDCI (1.5 equiv) and DMAP (2 equiv) in anhydrous dichloroethane (10 mL/mmol of acid) and stirred at room temperature for an hour. The 4-cyanobenzyl sulfonamide (1.2 equiv) is added to the reaction mixture and the reaction heated at 65° C. overnight. The reaction quenched by adding brine and extracted with EtOAc (30 mL/mmole of acid). The organic extracts were washed with brine, dried (Na$_2$SO$_4$), filtered, and concentrated under reduced pressure. The crude was purified by flash chromatography (100:0→50:50, hexanes: EtOAc) to give compounds 67, 68, 69, 71, 73, 75, and 78 as white foamy solids in 65-70% yields. The compound 72 was obtained in 20% yield.

N-[(4-Cyanophenyl)methanesulfonyl]-1-(4-fluorophenyl)-4-methylcyclohexane-1-carboxamide (67) $^1$H NMR (400 MHz, DMSO-d$_6$): δ 10.93 (bs, 1H), 7.60-7.70 (m, 2H), 7.35-7.42 (m, 2H), 7.14-7.24 (m, 4H), 4.74 (s, 2H), 1.76-1.35 (m, 4H), 0.99-0.73 (m, 6H). HRMS (ESI) m/z [M+H]$^+$ for C$_{22}$H$_{23}$FN$_2$O$_3$S, found 415.15.

N-[(4-Cyanophenyl)methanesulfonyl]-1-(4-fluorophenyl)-4,4-dimethylcyclohexane-1-carboxamide (68) $^1$H NMR (400 MHz, DMSO-d$_6$): δ 11.2 (bs, 1H), 7.66 (d, J=8.19 Hz, 2H), 7.36-7.27 (m, 4H), 7.23-7.16 (m, 2H), 4.81 (s, 2H), 2.32 (d, J=13.26 Hz, 2H), 1.67-1.81 (m, 2H), 1.20-1.27 (m, 4H), 0.87 (s, 3H), 0.82 (s, 3H). HRMS (ESI) m/z [M+H]$^+$ for C$_{23}$H$_{25}$FN$_2$O$_3$S, found 429.16.

N-[(4-Cyanophenyl)methanesulfonyl]-1-phenylcyclohexane-1-carboxamide (69) $^1$H NMR (400 MHz, DMSO-d$_6$): δ 11.1 (bs, 1H), 7.64 (d, J=8.19 Hz, 2H), 7.28-7.37 (m, 5H), 7.20-7.26 (m, 2H), 4.80 (s, 2H), 2.41 (d, J=13.26 Hz, 2H), 1.44-1.11 (m, 10H). HRMS (ESI) m/z [M+H]$^+$ for C$_{21}$H$_{22}$N$_2$O$_3$S, found 383.14.

N-[(4-Cyanophenyl)methanesulfonyl]-2,2-diphenylacetamide (71) $^1$H NMR (400 MHz, DMSO-d$_6$): δ 12.1 (bs, 1H), 7.64-7.72 (m, 2H), 7.32-7.39 (m, 4H), 7.24-7.31 (m, 8H) 4.98 (s, 1H), 4.82 (s, 1H). HRMS (ESI) m/z [M+H]$^+$ for C$_{22}$H$_{18}$N$_2$O$_3$S, found 391.11.

N-[(4-Cyanophenyl)methanesulfonyl]-2,2-bis(4-fluorophenyl)acetamide (72) $^1$H NMR (400 MHz, DMSO-d$_6$): δ 12.15 (bs, 1H), 7.71-7.76 (m, 2H), 7.34-7.07 (m, 10H), 5.00 (s, 1H), 4.82 (s, 1H). HRMS (ESI) m/z [M+H]$^+$ for C$_{22}$H$_{16}$F$_2$N$_2$O$_3$S, found 427.09.

N-[(4-Cyanophenyl)methanesulfonyl]-2,2-cyclohexylacetamide (73) $^1$H NMR (400 MHz, DMSO-d$_6$): δ 11.64 (bs, 1H), 7.98-7.74 (m, 2H), 7.67-7.63 (m, 2H), 4.95 (s, 2H), 2.09 (m, 1H), 1.66-1.42 (m, 22H). HRMS (ESI) m/z [M+H]$^+$ for C$_{22}$H$_{30}$N$_2$O$_3$S, found 403.20.

N-[(4-Cyanophenyl)methanesulfonyl]-1-(thiophen-2-yl)cyclohexane-1-carboxamide (75) $^1$H NMR (400 MHz, DMSO-d$_6$): δ 11.20 (bs, 1H), 7.65-7.69 (m, 2H), 7.52-7.50 (m, 1H), 7.17-7.22 (m, 2H), 7.04-7.02 (m, 1H), 6.97-7.00 (m, 1H), 4.79 (s, 2H), 2.42 (d, J=13.26 Hz, 2H), 1.75-1.70 (m, 2H), 1.55-1.45 (m, 3H), 1.34-1.22 (m, 3H). HRMS m/z [M+H]$^+$ for C$_{19}$H$_{20}$N$_2$O$_3$S$_2$, found 389.09.

N-[(4-Cyanophenyl)methanesulfonyl]-1-(thiophen-3-yl)cyclohexane-1-carboxamide (78) $^1$H NMR (400 MHz, DMSO-d$_6$): δ 11.06 (bs, 1H), 7.65-7.70 (m, 2H), 7.54-7.58 (m, 1H), 7.27-7.32 (m, 2H), 7.19-7.24 (m, 2H), 7.10-7.08 (m, 1H), 4.79 (s, 2H), 2.40 (d, J=13.65 Hz, 2H), 1.68-1.63 (m, 2H), 1.55-1.45 (m, 3H), 1.34-1.22 (m, 3H). HRMS m/z [M+H]$^+$ for C$_{19}$H$_{20}$N$_2$O$_3$S$_2$, found 389.09.

N-[(4-Cyano-3-bromophenyl)methanesulfonyl]-1-(thiophen-3-yl)cyclohexane-1-carboxamide (106) $^1$H NMR (400 MHz, DMSO-d$_6$): δ 11.06 (bs, 1H), 7.79 (d, J=7.80 Hz, 1H 2H), 7.75-7.59 (m, 1H), 7.58-7.34 (m, 1H), 7.32-7.13 (m, 2H), 7.03 (dd, J=5.07 Hz, 1.17 Hz, 1H), 4.79 (bs, 2H), 2.36 (d, J=11.70 Hz, 2H), 1.70-1.53 (m, 2H), 1.34-1.19 (m, 3H), 1.19-1.08 (m, 3H). HRMS m/z [M+H]$^+$ for C$_{19}$H$_{19}$N$_2$O$_3$S$_2$Br, found 467.01.

General Procedure for Synthesis of N-Sulfonylcarbamate Derivatives.

To an ice cold solution p-cyanobenzyl sulfonamide (1 equiv) was added NaH (1.5 equiv) portionwise and stirred at the same temperature for 1 hr. A solution of chloroformate 11a or 12a (1.2 equiv) was then added dropwise, and the reaction stirred at room temperature for 12 hr. The reaction was quenched by adding brine and extracted with EtOAc (30 mL/mmol of p-cyanobenzylsulfonamide). The organic extracts were washed with brine, dried (Na$_2$SO$_4$), filtered, and concentrated under reduced pressure. The crude was purified by flash chromatography (100:0→50:50, hexanes:EtOAc) to a give compound 65 as a white solid in 60% yield.

2-Methylpropyl N-[(4-cyanophenyl)methanesulfonyl]carbamate (65) $^1$H NMR (400 MHz, CDCl$_3$): δ 7.70-7.66 (m, 2H), 7.52-7.48 (m, 2H), 7.08 (s, 1H), 4.01 (d, J=6.63, 2H), 1.93-2.03 (m, 1H), 0.93-0.97 (m, 6H). HRMS (ESI) m/z [M+H]$^+$ for C$_{13}$H$_{16}$N$_2$O$_4$S, found 297.09.

TABLE X

Exemplary Structures

| Compound No. | Structure |
|---|---|
| 63 | 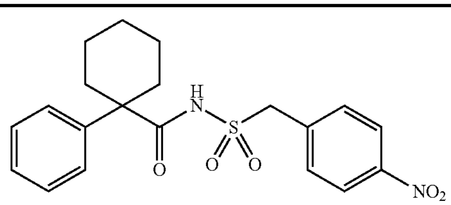 |
| 64 | 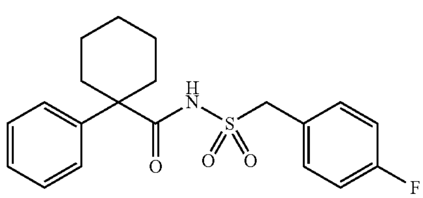 [SMILES: O=C(NS(=O)(=O)Cc1ccc(F)cc1)C1(c2ccccc2)CCCCC1] |
| 65 | 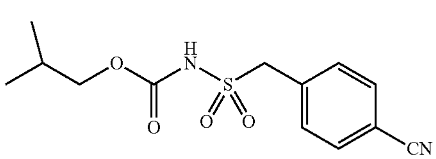 [SMILES: CC(C)COC(=O)NS(=O)(=O)Cc1ccc(C#N)cc1] |

TABLE X-continued

Exemplary Structures

| Compound No. | Structure |
|---|---|
| 67 | 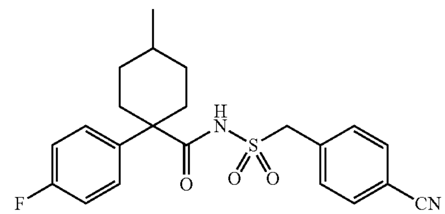 [SMILES: CC1CCC(C(=O)NS(=O)(=O)Cc2ccc(C#N)cc2)(c2ccc(F)cc2)CC1] |
| 68 | 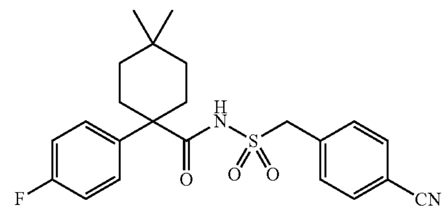 [SMILES: CC1(C)CCC(C(=O)NS(=O)(=O)Cc2ccc(C#N)cc2)(c2ccc(F)cc2)CC1] |
| 69 | 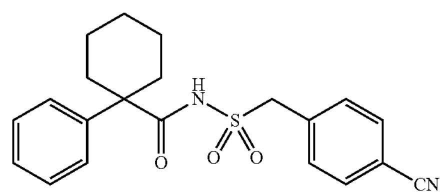 [SMILES: N#Cc1ccc(CS(=O)(=O)NC(=O)C2(c3ccccc3)CCCCC2)cc1] |
| 71 | 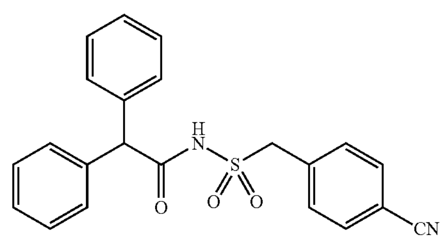 [SMILES: N#Cc1ccc(CS(=O)(=O)NC(=O)C(c2ccccc2)c2ccccc2)cc1] |
| 72 | 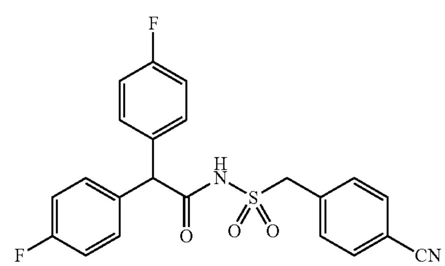 [SMILES: N#Cc1ccc(CS(=O)(=O)NC(=O)C(c2ccc(F)cc2)c2ccc(F)cc2)cc1] |
| 73 | 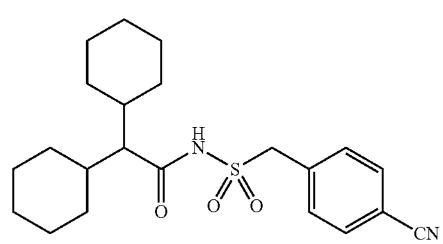 [SMILES: N#Cc1ccc(CS(=O)(=O)NC(=O)C(C2CCCCC2)C2CCCCC2)cc1] |

TABLE X-continued

Exemplary Structures

| Compound No. | Structure |
|---|---|
| 75 | *(structure: 1-(thiophen-2-yl)cyclohexane-1-carboxamide N-sulfonyl-CH2-C6H4-CN)* |
| 78 | *(structure: 1-(thiophen-3-yl)cyclohexane-1-carboxamide N-sulfonyl-CH2-C6H4-CN)* |
| 106 | *(structure: 1-(thiophen-3-yl)cyclohexane-1-carboxamide N-sulfonyl-CH2-C6H3(Br)-CN)* |

General Procedure for Synthesis of Additional Derivatives

The following compounds are made by similar procedures to those above.

TABLE XI

Exemplary Structures

*(structure: 1-(pyridin-2-yl)cyclohexane-1-carboxamide N-sulfonyl-CH2-C6H4-CN)*

*(structure: 1-(pyridin-3-yl)cyclohexane-1-carboxamide N-sulfonyl-CH2-C6H4-CN)*

*(structure: 1-(pyridin-2-yl)cyclohexane-1-carboxamide N-sulfonyl-C(CH3)2-C6H4-CN)*

TABLE XI-continued

Exemplary Structures

*(structure: 1-(pyridin-3-yl)cyclohexane-1-carboxamide N-sulfonyl-C(CH3)2-C6H4-CN)*

*(structure: 1-(thiophen-2-yl)cyclohexane-1-carboxamide N-sulfonyl-C(CH3)2-C6H4-CN)*

*(structure: 1-(thiophen-3-yl)cyclohexane-1-carboxamide N-sulfonyl-C(CH3)2-C6H4-CN)*

*(structure: 1-(furan-3-yl)cyclohexane-1-carboxamide N-sulfonyl-CH2-C6H4-CN)*

*(structure: 1-(furan-2-yl)cyclohexane-1-carboxamide N-sulfonyl-CH2-C6H4-CN)*

*(structure: 1-(furan-3-yl)cyclohexane-1-carboxamide N-sulfonyl-C(CH3)2-C6H4-CN)*

*(structure: 1-(furan-2-yl)cyclohexane-1-carboxamide N-sulfonyl-C(CH3)2-C6H4-CN)*

TABLE XI-continued

Exemplary Structures

Example 3

Biological Activity of Additional N-Acylsulfonamide and N-Sulfonylcarbamate Derivatives Additional compounds were tested for biological activity following the procedures of Example 1 with minor modifications. The results are indicated in Tables XII to XV.

For these in vitro receptor assays, the compounds listed were tested in in vitro PP2C inhibition assays with 50 uM of the test compound except for ABA (10 uM). $IC_{50}$s were calculated from dose curves, but only for selected compounds.

TABLE XIII

Germination Inhibition II

| Compound No. | Germination Inhibition | Hypocotyl Growth Inhibition |
|---|---|---|
| Mock | – | – |
| ABA | 1 | |
| 1 | – | 50 |
| 24 | 10 | |
| 25 | 50 | 10 |
| 26 | 50 | 10 |
| 27 | – | 50 |
| 56 | – | – |
| 28 | – | 10 |
| 29 | 50 | 10 |
| 30 | – | 50 |
| 31 | – | – |
| 32 | 50 | 10 |
| 33 | – | 10 |
| 34 | 50 | |
| 35 | – | 10 |
| 2 | 50 | 10 |
| 36 | – | – |
| 37 | – | 50 |
| 3 | 50 | 10 |
| 4 | – | 50 |
| 5 | – | 50 |

TABLE XII

PP2C Activity (50 μm)

| Cmpd. No. | PYR1 | PYL1 | PYL2 | PYL3 | PYL4 | PYL5 | PYL6 | PYL8 | PYL9 | PYL10 | PYL11 |
|---|---|---|---|---|---|---|---|---|---|---|---|
| 63 | 101.4 | 101.1 | 115.2 | 126.6 | 103.4 | 107.3 | 108.5 | 96.6 | 75.5 | 88.9 | 92.6 |
| 64 | 98.4 | 101.7 | 106.8 | 97.4 | 105.1 | 103.2 | 108.8 | 101.1 | 91.1 | 89.8 | 97.5 |
| 65 | 96.2 | 91.7 | 95.2 | 92.9 | 95.5 | 23.6 | 58.9 | 35.8 | 18.6 | 39.2 | 42.1 |
| 67 | 99.6 | 98.3 | 93.0 | 101.0 | 91.9 | 43.0 | 46.6 | 25.8 | 8.0 | 48.2 | 14.7 |
| 68 | 94.4 | 96.0 | 94.8 | 98.3 | 94.0 | 102.7 | 46.6 | 57.5 | 22.6 | 83.3 | 16.2 |
| 69 | 96.0 | 98.4 | 96.2 | 102.8 | 95.0 | 118.9 | 72.6 | 14.7 | 5.8 | 27.3 | 13.5 |
| 71 | 97.9 | 93.8 | 102.5 | 101.6 | 93.2 | 102.0 | 96.9 | 96.8 | 81.8 | 86.5 | 43.2 |
| 72 | 93.9 | 94.2 | 100.5 | 100.0 | 90.1 | 101.6 | 95.1 | 98.5 | 85.8 | 98.0 | 37.4 |
| 73 | 91.6 | 95.5 | 93.8 | 92.7 | 98.2 | 109.7 | 91.0 | 66.1 | 56.3 | 85.7 | 26.9 |
| 75 | 96.1 | 95.5 | 89.5 | 95.4 | 98.0 | 81.8 | 57.2 | 14.9 | 6.9 | 27.0 | 9.8 |
| 78 | 90.9 | 95.6 | 81.2 | 102.8 | 101.6 | 68.5 | 44.9 | 14.3 | 6.1 | 25.6 | 9.9 |
| 106 | 98.9 | 94.3 | 29.6 | 96.9 | 89.2 | 11.9 | 17.6 | 13.6 | 5.4 | 22.5 | 7.8 |
| ABA (10 μM) | 6.0 | 5.9 | 6.1 | 5.4 | 10.2 | 4.9 | 10.9 | 7.0 | 6.3 | 13.8 | 5.7 |

TABLE XII-B

PP2C Activity ($IC_{50}$ in uM)

| Cmpd. No. | PYR1 | PYL1 | PYL2 | PYL3 | PYL4 | PYL5 | PYL6 | PYL8 | PYL9 | PYL10 | PYL11 |
|---|---|---|---|---|---|---|---|---|---|---|---|
| 63 | >50 | >50 | >50 | >50 | >50 | >50 | >50 | >50 | >50 | >50 | >50 |
| 64 | >50 | >50 | >50 | >50 | >50 | >50 | >50 | >50 | >50 | >50 | >50 |
| 65 | >50 | >50 | >50 | >50 | >50 | 14.2 | >50 | 20.4 | 6.5 | 19.2 | 50 |
| 67 | >50 | >50 | >50 | >50 | >50 | 25.3 | 50 | 9.6 | 2.131 | 50.0 | 3.130 |
| 68 | >50 | >50 | >50 | >50 | >50 | >50 | 50 | >50 | 17.70 | >50 | 2.220 |
| 69 | >50 | >50 | >50 | >50 | >50 | >50 | >50 | 0.750 | 0.135 | 1.690 | 2.530 |
| 71 | >50 | >50 | >50 | >50 | >50 | >50 | >50 | >50 | >50 | >50 | 25 |
| 72 | >50 | >50 | >50 | >50 | >50 | >50 | >50 | >50 | >50 | >50 | 25 |
| 73 | >50 | >50 | >50 | >50 | >50 | >50 | >50 | >50 | >50 | >50 | 22.40 |
| 75 | >50 | >50 | >50 | >50 | >50 | >50 | >50 | 0.134 | 0.083 | 0.380 | 0.390 |
| 78 | >50 | >50 | >50 | >50 | >50 | >50 | 25 | 0.073 | 0.038 | 0.250 | 0.190 |
| 106 | >50 | >50 | 32.96 | >50 | >50 | 7.261 | 7.841 | 0.037 | 0.014 | 0.022 | 0.065 |

TABLE XIII-continued

Germination Inhibition II

| Compound No. | Germination Inhibition | Hypocotyl Growth Inhibition |
|---|---|---|
| 6 | 50 | 10 |
| 57 | – | – |
| 38 | – | 50 |
| 58 | – | – |
| 59 | – | – |
| 39 | 50 | 10 |
| 53 | – | 50 |
| 7 | 50 | 10 |
| 40 | | – |
| 41 | – | 10 |
| 42 | 50 | 10 |
| 8 | 50 | 10 |
| 61 | – | 50 |
| 9 | – | 10 |
| 43 | 50 | 10 |
| 10 | – | 50 |
| 44 | – | 50 |
| 11 | – | – |
| 45 | – | – |
| 12 | – | 50 |
| 13 | 10 | |
| 14 | – | – |
| 46 | – | – |
| 47 | – | – |
| 15 | – | 10 |
| 16 | 50 | 10 |
| 17 | – | 50 |
| 18 | – | – |
| 54 | – | 50 |
| 48 | | 50 |
| 19 | 10 | |
| 20 | – | – |
| 49 | – | – |
| 21 | – | – |
| 22 | – | 10 |
| 50 | | – |
| 51 | 10 | |
| 52 | – | – |
| 62 | – | – |
| 55 | – | – |
| 60 | – | – |
| 23 | 50 | 10 |

For the germination inhibition experiment, the compounds were tested at 10 and 50 uM. The amounts shown are the lowest of the two concentrations that either inhibited germination or hypocotyl growth in wells where seeds germinated.

TABLE XIV

Thermal Response II

| Compound No. | Response |
|---|---|
| 63 | nd |
| 64 | nd |
| 65 | nd |
| 67 | — |
| 68 | + |
| 69 | +++ |
| 71 | nd |
| 72 | nd |
| 73 | nd |
| 75 | +++ |
| 78 | +++ |
| 106 | +++ |
| 13 | ++ |
| ABA | +++ |

For the thermal response experiment, the compounds were tested by spraying *Arabidopsis* plants with 50 uM solution of test compound. Thermal imaging was then conducted after 24 hours.

TABLE XIII

Germination Effects III

| Compound No. | Germination Inhibition(uM) | Growth Inhibition(uM) |
|---|---|---|
| 63 | — | — |
| 64 | — | — |
| 65 | — | 50 |
| 67 | 25 | 10 |
| 68 | 25 | 10 |
| 69 | 5 | 1 |
| 71 | — | — |
| 72 | — | — |
| 73 | — | — |
| 75 | 5 | 5 |
| 78 | 2.5 | 2.5 |
| 106 | 1 | 1 |
| 13 | 10 | 5 |

For the germination test, the compounds were tested at 1, 5, 10, 25 and 50 uM. The amounts shown are the lowest of the concentrations that either inhibited germination or hypocotyl growth in the wells where seeds germinated.

For the thermal response test, the compounds were tested by spraying *Arabidopsis* plants with 50 uM solution of test compound. Thermal imaging was conducted after 24 hours.

What is claimed is:

1. A method of increasing abiotic stress tolerance in a plant, the method comprising contacting a plant with an effective amount of a sulfonamide agonist compound to activate abscisic acid receptors in the plant, thereby increasing abiotic stress tolerance; wherein the sulfonamide agonist compound is of Formula I:

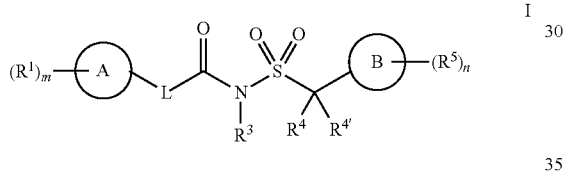

wherein:

A is selected from the group consisting of alkyl, aryl, arylalkyl, heteroaryl, heteroarylalkyl, heterocyclyl, and cycloalkyl;

each $R^1$ is a substituent independently selected from the group consisting of alkyl, alkenyl, alkynyl, cycloalkyl, heterocyclyl, aryl, heteroaryl, halo, fluoroalkyl, hydroxyl, hydroxyalkyl, alkoxy, fluoroalkoxy, alkoxyalkyl, amino, aminoalkyl, alkylthio, alkylthioalkyl, cyano, carboxyl, carboxyalkyl, alkoxycarbonyl, alkoxycarbonylalkyl, amido, and amidoalkyl; wherein the $R^1$ cycloalkyl, heterocyclyl, aryl, or heteroaryl is additionally substituted with from 0 to 3 $R^6$; or alternatively, two $R^1$ substituents join to form an additional $R^1$ ring, wherein the additional $R^1$ ring is selected from the group consisting of aryl, heteroaryl, cycloalkyl, and heterocyclyl; and wherein the additional $R^1$ ring is additionally substituted with from 0 to 3 $R^6$; or m is an integer selected from 0 to 5; wherein if A is not aryl or if at least two $R^1$ are not halo, m is an integer selected from 0 to 3;

L is $-C(R^2)(R^{2'})$;

$R^2$ and $R^{2'}$ join to form a geminal cyclopropyl, cyclobutyl, cyclopenyl, cyclohexyl, 4-methylcyclohexyl, 4,4-dimethylcyclohexyl, piperidinyl, N-acylpiperidinyl, N-alkylpiperidinyl, tetrahydro-2H-pyranyl, or cycloheptyl ring; and wherein the geminal $R^2$ ring is additionally substituted with from 0 to 4 $R^6$;

$R^3$ is a substituent selected from the group consisting of hydrogen, alkyl, and fluoroalkyl; and $R^4$ and $R^{4'}$ are each a substituent independently selected from the group consisting of hydrogen, alkyl, chloro, fluoro, and fluoroalkyl; or alternatively, an $R^4$ and an $R^{4'}$ join to form a geminal $R^4$ ring, wherein the geminal $R^4$ ring is selected from the group consisting of cycloalkyl, cycloalkenyl, and heterocyclyl; and wherein the geminal $R^4$ ring is additionally substituted with from 0 to 4 $R^6$;

B is selected from the group consisting of aryl, heteroaryl, and heterocyclyl;

each $R^5$ is a substituent independently selected from the group consisting of alkyl, alkenyl, alkynyl, cycloalkyl, cycloalkenyl, heterocyclyl, aryl, heteroaryl, halo, fluoroalkyl, nitro, hydroxyl, hydroxyalkyl, alkoxy, alkoxyalkyl, amino, aminoalkyl, alkylthio, alkylthioalkyl, cyano, carboxyl, carboxyalkyl, alkoxycarbonyl, alkoxycarbonylalkyl, amido, and amidoalkyl; or alternatively, two $R^5$ join to form an additional $R^5$ ring, wherein the additional $R^5$ ring is selected from the group consisting of aryl, heteroaryl, cycloalkyl, and heterocyclyl; and wherein the additional $R^5$ ring is additionally substituted with from 0 to 5 $R^6$;

n is an integer selected from 0 to 5; wherein if B is not aryl or if at least two $R^5$ are not halo, m is an integer selected from 0 to 3; and each $R^6$ is a substituent independently selected from the group consisting of alkyl, aryl, halo, fluoroalkyl, hydroxyl, alkoxy, amino, cyano, carboxyl, alkoxycarbonyl, and amido.

2. The method of claim 1, wherein A is aryl.

3. The method of claim 2, wherein A is phenyl, 4-cyanophenyl, 4-nitrophenyl, or 4-fluorophenyl.

4. The method of claim 1, wherein the sulfonamide agonist compound is of Formula II:

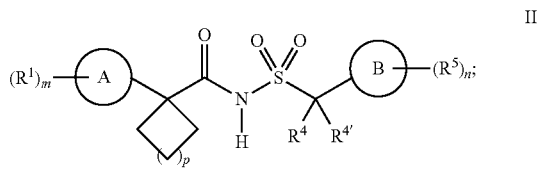

wherein:

A is heteroaryl;

p is an integer selected from 0 to 4;

$R^4$ and $R^{4'}$ are independently hydrogen or lower alkyl; and

B is heteroaryl.

5. The method of claim 1, wherein the sulfonamide agonist compound is of Formula IIIB:

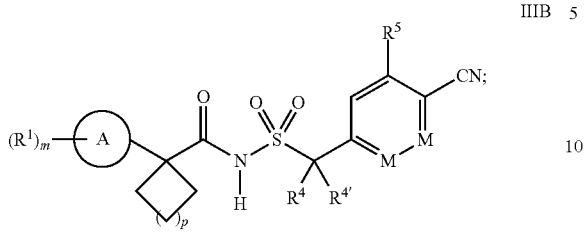

wherein:
p is an integer selected from 0 to 4;
$R^4$ and $R^{4'}$ are independently hydrogen or lower alkyl; and
each M is independently CH or N.

6. The method of claim 1, wherein the sulfonamide agonist compound is of Formula IV:

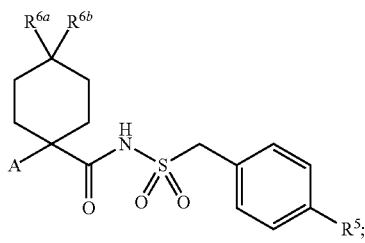

wherein:
A is selected from the group consisting of 2-thiophenyl, 3-thiophenyl, 2-furanyl, 3-furanyl, 2-pyrrolyl, and 3-pyrrolyl; and
$R^{6a}$ and $R^{6b}$ are each independently selected from the group consisting of hydrogen, hydroxyl, alkoxy, alkyl, fluoroalkyl, and halo.

7. The method of claim 1, wherein the sulfonamide agonist compound is selected from the group consisting of

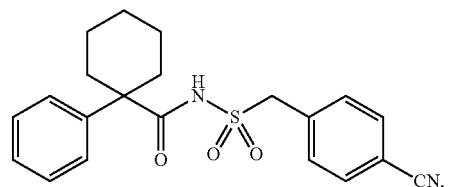

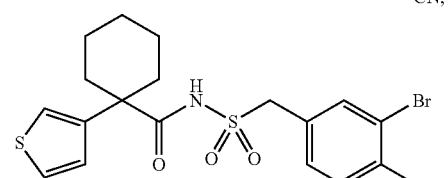

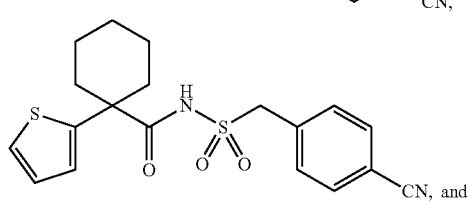

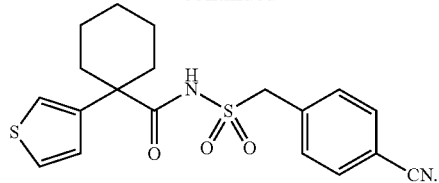

8. The method of claim 1, wherein the geminal $R^2$ ring is additionally substituted with 0 $R^6$.

9. The method of claim 1, wherein $R^1$ and $R^{2'}$ join to form a geminal cyclopropyl, cyclobutyl, cyclopentyl, cyclohexyl, or cycloheptyl ring.

10. The method of claim 1, wherein $R^4$ is hydrogen or alkyl.

11. The method of claim 1, wherein B is aryl.

12. The method of claim 1, wherein $R^5$ is a para-substituent.

13. The method of claim 1, wherein $R^5$ is a hydrogen bond acceptor.

14. The method of claim 13, wherein $R^5$ is independently selected from the group consisting of hydroxyl, lower alkoxy, cyclopropyloxy, amino, lower alkylamino, carboxy, lower alkoxycarbonyl, lower amido, thio, and lower alkylthio.

15. The method of claim 1, wherein $R^5$ is independently selected from the group consisting of cyano, fluoro, halo, and nitro.

16. The method of claim 1, wherein the abiotic stress tolerance comprises drought tolerance.

17. The sulfonamide agonist compound of the method of claim 1, with the proviso that the compound is not selected from the group consisting of:

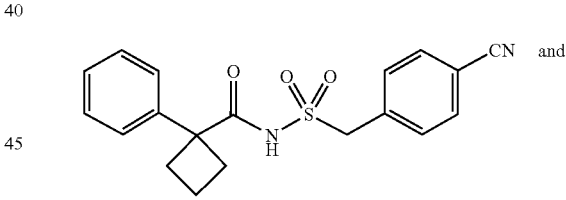

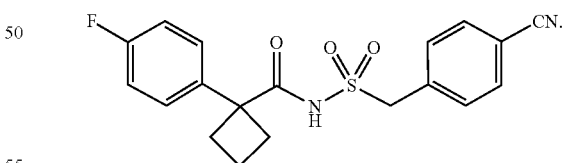

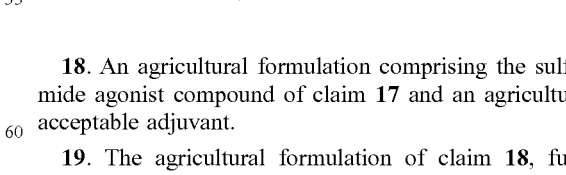

18. An agricultural formulation comprising the sulfonamide agonist compound of claim 17 and an agriculturally acceptable adjuvant.

19. The agricultural formulation of claim 18, further comprising at least one of a fungicide, an herbicide, a pesticide, a nematicide, an insecticide, a plant activator, a synergist, an herbicide safener, a plant growth regulator, an insect repellant, an acaricide, a molluscicide, or a fertilizer.

* * * * *

SEQUENCE LISTING

```
<160> NUMBER OF SEQ ID NOS: 119

<210> SEQ ID NO 1
<211> LENGTH: 191
<212> TYPE: PRT
<213> ORGANISM: Arabidopsis thaliana

<400> SEQUENCE: 1

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45
```

Val Arg Arg Phe Asp Lys Pro Gln Thr Tyr Lys His Phe Ile Lys Ser
 50                  55                  60

Cys Ser Val Glu Gln Asn Phe Glu Met Arg Val Gly Cys Thr Arg Asp
 65                  70                  75                  80

Val Ile Val Ile Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
             100                 105                 110

Gly Glu His Arg Leu Thr Asn Tyr Lys Ser Val Thr Val His Arg
         115                 120                 125

Phe Glu Lys Glu Asn Arg Ile Trp Thr Val Val Leu Glu Ser Tyr Val
     130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                 165                 170                 175

Ala Met Ala Arg Asn Ser Gly Asp Gly Ser Gly Ser Gln Val Thr
             180                 185                 190

<210> SEQ ID NO 2
<211> LENGTH: 221
<212> TYPE: PRT
<213> ORGANISM: Arabidopsis thaliana

<400> SEQUENCE: 2

Met Ala Asn Ser Glu Ser Ser Ser Pro Val Asn Glu Glu Glu Asn
 1               5                  10                  15

Ser Gln Arg Ile Ser Thr Leu His His Gln Thr Met Pro Ser Asp Leu
                 20                  25                  30

Thr Gln Asp Glu Phe Thr Gln Leu Ser Gln Ser Ile Ala Glu Phe His
             35                  40                  45

Thr Tyr Gln Leu Gly Asn Gly Arg Cys Ser Ser Leu Leu Ala Gln Arg
 50                  55                  60

Ile His Ala Pro Pro Glu Thr Val Trp Ser Val Arg Arg Phe Asp
 65                  70                  75                  80

Arg Pro Gln Ile Tyr Lys His Phe Ile Lys Ser Cys Asn Val Ser Glu
                 85                  90                  95

Asp Phe Glu Met Arg Val Gly Cys Thr Arg Asp Val Asn Val Ile Ser
             100                 105                 110

Gly Leu Pro Ala Asn Thr Ser Arg Glu Arg Leu Asp Leu Leu Asp Asp
         115                 120                 125

Asp Arg Arg Val Thr Gly Phe Ser Ile Thr Gly Gly Glu His Arg Leu
130                 135                 140

Arg Asn Tyr Lys Ser Val Thr Val His Arg Phe Glu Lys Glu Glu
145                 150                 155                 160

Glu Glu Glu Arg Ile Trp Thr Val Val Leu Glu Ser Tyr Val Val Asp
                 165                 170                 175

Val Pro Glu Gly Asn Ser Glu Glu Asp Thr Arg Leu Phe Ala Asp Thr
             180                 185                 190

Val Ile Arg Leu Asn Leu Gln Lys Leu Ala Ser Ile Thr Glu Ala Met
         195                 200                 205

Asn Arg Asn Asn Asn Asn Asn Ser Ser Gln Val Arg
210                 215                 220

```
<210> SEQ ID NO 3
<211> LENGTH: 190
<212> TYPE: PRT
<213> ORGANISM: Arabidopsis thaliana

<400> SEQUENCE: 3

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

His Phe Val Lys Arg Cys Arg Leu Ile Ser Gly Asp Gly Asp Val Gly
65                  70                  75                  80

Ser Val Arg Glu Val Thr Val Ile Ser Gly Leu Pro Ala Ser Thr Ser
                85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
    130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Asp Glu
            180                 185                 190

<210> SEQ ID NO 4
<211> LENGTH: 209
<212> TYPE: PRT
<213> ORGANISM: Arabidopsis thaliana

<400> SEQUENCE: 4

Met Asn Leu Ala Pro Ile His Asp Pro Ser Ser Ser Thr Thr Thr
1               5                   10                  15

Thr Ser Ser Ser Thr Pro Tyr Gly Leu Thr Lys Asp Glu Phe Ser Thr
            20                  25                  30

Leu Asp Ser Ile Ile Arg Thr His His Thr Phe Pro Arg Ser Pro Asn
        35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65                  70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Val Ser Gly Leu Pro
            100                 105                 110

Ala Ser Thr Ser Val Glu Ile Leu Glu Val Leu Asp Glu Glu Lys Arg
        115                 120                 125

Ile Leu Ser Phe Arg Val Leu Gly Gly Glu His Arg Leu Asn Asn Tyr
    130                 135                 140

Arg Ser Val Thr Ser Val Asn Glu Phe Val Val Leu Glu Lys Asp Lys
```

```
            145                 150                 155                 160
Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
                180                 185                 190

Val Lys Ser Asn Leu Gln Asn Leu Ala Val Ile Ser Thr Ala Ser Pro
            195                 200                 205

Thr

<210> SEQ ID NO 5
<211> LENGTH: 207
<212> TYPE: PRT
<213> ORGANISM: Arabidopsis thaliana

<400> SEQUENCE: 5

Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
                20                  25                  30

Leu Ser Arg Asp Ser Thr Ala Ala Arg Phe His Thr His Glu Val Gly
            35                  40                  45

Pro Asn Gln Cys Cys Ser Ala Val Ile Gln Glu Ile Ser Ala Pro Ile
50                  55                  60

Ser Thr Val Trp Ser Val Val Arg Arg Phe Asp Asn Pro Gln Ala Tyr
65                  70                  75                  80

Lys His Phe Leu Lys Ser Cys Ser Val Ile Gly Gly Asp Gly Asp Asn
                85                  90                  95

Val Gly Ser Leu Arg Gln Val His Val Val Ser Gly Leu Pro Ala Ala
            100                 105                 110

Ser Ser Thr Glu Arg Leu Asp Ile Leu Asp Asp Glu Arg His Val Ile
            115                 120                 125

Ser Phe Ser Val Val Gly Gly Asp His Arg Leu Ser Asn Tyr Arg Ser
        130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
                180                 185                 190

Ile Ala Glu Asn Thr Ala Ala Glu Ser Lys Lys Lys Met Ser Leu
            195                 200                 205

<210> SEQ ID NO 6
<211> LENGTH: 203
<212> TYPE: PRT
<213> ORGANISM: Arabidopsis thaliana

<400> SEQUENCE: 6

Met Arg Ser Pro Val Gln Leu Gln His Gly Ser Asp Ala Thr Asn Gly
1               5                   10                  15

Phe His Thr Leu Gln Pro His Asp Gln Thr Asp Gly Pro Ile Lys Arg
                20                  25                  30

Val Cys Leu Thr Arg Gly Met His Val Pro Glu His Val Ala Met His
            35                  40                  45

His Thr His Asp Val Gly Pro Asp Gln Cys Cys Ser Ser Val Val Gln
        50                  55                  60
```

```
Met Ile His Ala Pro Pro Glu Ser Val Trp Ala Leu Val Arg Arg Phe
 65                  70                  75                  80

Asp Asn Pro Lys Val Tyr Lys Asn Phe Ile Arg Gln Cys Arg Ile Val
                 85                  90                  95

Gln Gly Asp Gly Leu His Val Gly Asp Leu Arg Glu Val Met Val Val
            100                 105                 110

Ser Gly Leu Pro Ala Val Ser Ser Thr Glu Arg Leu Glu Ile Leu Asp
        115                 120                 125

Glu Glu Arg His Val Ile Ser Phe Ser Val Val Gly Gly Asp His Arg
    130                 135                 140

Leu Lys Asn Tyr Arg Ser Val Thr Thr Leu His Ala Ser Asp Asp Glu
145                 150                 155                 160

Gly Thr Val Val Glu Ser Tyr Ile Val Asp Val Pro Pro Gly Asn
                165                 170                 175

Thr Glu Glu Glu Thr Leu Ser Phe Val Asp Thr Ile Val Arg Cys Asn
                180                 185                 190

Leu Gln Ser Leu Ala Arg Ser Thr Asn Arg Gln
            195                 200
```

<210> SEQ ID NO 7
<211> LENGTH: 215
<212> TYPE: PRT
<213> ORGANISM: Arabidopsis thaliana

<400> SEQUENCE: 7

```
Met Pro Thr Ser Ile Gln Phe Gln Arg Ser Ser Thr Ala Ala Glu Ala
 1               5                  10                  15

Ala Asn Ala Thr Val Arg Asn Tyr Pro His His Gln Lys Gln Val
                 20                  25                  30

Gln Lys Val Ser Leu Thr Arg Gly Met Ala Asp Val Pro Glu His Val
             35                  40                  45

Glu Leu Ser His Thr His Val Val Gly Pro Ser Gln Cys Phe Ser Val
     50                  55                  60

Val Val Gln Asp Val Glu Ala Pro Val Ser Thr Val Trp Ser Ile Leu
 65                  70                  75                  80

Ser Arg Phe Glu His Pro Gln Ala Tyr Lys His Phe Val Lys Ser Cys
                 85                  90                  95

His Val Val Ile Gly Asp Gly Arg Glu Val Gly Ser Val Arg Glu Val
            100                 105                 110

Arg Val Val Ser Gly Leu Pro Ala Ala Phe Ser Leu Glu Arg Leu Glu
        115                 120                 125

Ile Met Asp Asp Arg His Val Ile Ser Phe Ser Val Val Gly Gly
    130                 135                 140

Asp His Arg Leu Met Asn Tyr Lys Ser Val Thr Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
            180                 185                 190

Ala Asp Thr Ile Val Arg Cys Asn Leu Gln Ser Leu Ala Lys Leu Ala
        195                 200                 205

Glu Asn Thr Ser Lys Phe Ser
    210                 215
```

```
<210> SEQ ID NO 8
<211> LENGTH: 211
<212> TYPE: PRT
<213> ORGANISM: Arabidopsis thaliana

<400> SEQUENCE: 8

Met Glu Met Ile Gly Gly Asp Asp Thr Asp Thr Glu Met Tyr Gly Ala
1               5                   10                  15

Leu Val Thr Ala Gln Ser Leu Arg Leu Arg His Leu His His Cys Arg
                20                  25                  30

Glu Asn Gln Cys Thr Ser Val Leu Val Lys Tyr Ile Gln Ala Pro Val
            35                  40                  45

His Leu Val Trp Ser Leu Val Arg Arg Phe Asp Gln Pro Gln Lys Tyr
        50                  55                  60

Lys Pro Phe Ile Ser Arg Cys Thr Val Asn Gly Asp Pro Glu Ile Gly
65                  70                  75                  80

Cys Leu Arg Glu Val Asn Val Lys Ser Gly Leu Pro Ala Thr Thr Ser
                85                  90                  95

Thr Glu Arg Leu Glu Gln Leu Asp Asp Glu His Ile Leu Gly Ile
                100                 105                 110

Asn Ile Ile Gly Gly Asp His Arg Leu Lys Asn Tyr Ser Ser Ile Leu
            115                 120                 125

Thr Val His Pro Glu Met Ile Asp Gly Arg Ser Gly Thr Met Val Met
        130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
            180                 185                 190

Thr Phe Cys Asn Ala Ser Asn Gly Tyr Arg Glu Lys Asn His Thr Glu
        195                 200                 205

Thr Asn Leu
    210

<210> SEQ ID NO 9
<211> LENGTH: 188
<212> TYPE: PRT
<213> ORGANISM: Arabidopsis thaliana

<400> SEQUENCE: 9

Met Glu Ala Asn Gly Ile Glu Asn Leu Thr Asn Pro Asn Gln Glu Arg
1               5                   10                  15

Glu Phe Ile Arg Arg His His Lys His Glu Leu Val Asp Asn Gln Cys
                20                  25                  30

Ser Ser Thr Leu Val Lys His Ile Asn Ala Pro Val His Ile Val Trp
            35                  40                  45

Ser Leu Val Arg Arg Phe Asp Gln Pro Gln Lys Tyr Lys Pro Phe Ile
        50                  55                  60

Ser Arg Cys Val Val Lys Gly Asn Met Glu Ile Gly Thr Val Arg Glu
65                  70                  75                  80

Val Asp Val Lys Ser Gly Leu Pro Ala Thr Arg Ser Thr Glu Arg Leu
                85                  90                  95

Glu Leu Leu Asp Asp Asn Glu His Ile Leu Ser Ile Arg Ile Val Gly
            100                 105                 110

Gly Asp His Arg Leu Lys Asn Tyr Ser Ser Ile Ile Ser Leu His Pro
```

```
            115                 120                 125
Glu Thr Ile Glu Gly Arg Ile Gly Thr Leu Val Ile Glu Ser Phe Val
        130                 135                 140
Val Asp Val Pro Glu Gly Asn Thr Lys Asp Glu Thr Cys Tyr Phe Val
145                 150                 155                 160
Glu Ala Leu Ile Lys Cys Asn Leu Lys Ser Leu Ala Asp Ile Ser Glu
                165                 170                 175
Arg Leu Ala Val Gln Asp Thr Thr Glu Ser Arg Val
            180                 185
```

<210> SEQ ID NO 10
<211> LENGTH: 187
<212> TYPE: PRT
<213> ORGANISM: Arabidopsis thaliana

<400> SEQUENCE: 10

```
Met Met Asp Gly Val Glu Gly Gly Thr Ala Met Tyr Gly Gly Leu Glu
1               5                   10                  15
Thr Val Gln Tyr Val Arg Thr His His Gln His Leu Cys Arg Glu Asn
                20                  25                  30
Gln Cys Thr Ser Ala Leu Val Lys His Ile Lys Ala Pro Leu His Leu
            35                  40                  45
Val Trp Ser Leu Val Arg Arg Phe Asp Gln Pro Gln Lys Tyr Lys Pro
        50                  55                  60
Phe Val Ser Arg Cys Thr Val Ile Gly Asp Pro Glu Ile Gly Ser Leu
65                  70                  75                  80
Arg Glu Val Asn Val Lys Ser Gly Leu Pro Ala Thr Thr Ser Thr Glu
                85                  90                  95
Arg Leu Glu Leu Leu Asp Asp Glu Glu His Ile Leu Gly Ile Lys Ile
            100                 105                 110
Ile Gly Gly Asp His Arg Leu Lys Asn Tyr Ser Ser Ile Leu Thr Val
        115                 120                 125
His Pro Glu Ile Ile Glu Gly Arg Ala Gly Thr Met Val Ile Glu Ser
    130                 135                 140
Phe Val Val Asp Val Pro Gln Gly Asn Thr Lys Asp Glu Thr Cys Tyr
145                 150                 155                 160
Phe Val Glu Ala Leu Ile Arg Cys Asn Leu Lys Ser Leu Ala Asp Val
                165                 170                 175
Ser Glu Arg Leu Ala Ser Gln Asp Ile Thr Gln
            180                 185
```

<210> SEQ ID NO 11
<211> LENGTH: 183
<212> TYPE: PRT
<213> ORGANISM: Arabidopsis thaliana

<400> SEQUENCE: 11

```
Met Asn Gly Asp Glu Thr Lys Lys Val Glu Ser Glu Tyr Ile Lys Lys
1               5                   10                  15
His His Arg His Glu Leu Val Glu Ser Gln Cys Ser Ser Thr Leu Val
                20                  25                  30
Lys His Ile Lys Ala Pro Leu His Leu Val Trp Ser Ile Val Arg Arg
            35                  40                  45
Phe Asp Glu Pro Gln Lys Tyr Lys Pro Phe Ile Ser Arg Cys Val Val
        50                  55                  60
Gln Gly Lys Lys Leu Glu Val Gly Ser Val Arg Glu Val Asp Leu Lys
```

```
                65                  70                  75                  80
Ser Gly Leu Pro Ala Thr Lys Ser Thr Glu Val Leu Glu Ile Leu Asp
                    85                  90                  95

Asp Asn Glu His Ile Leu Gly Ile Arg Ile Val Gly Gly Asp His Arg
                100                 105                 110

Leu Lys Asn Tyr Ser Ser Thr Ile Ser Leu His Ser Glu Thr Ile Asp
                115                 120                 125

Gly Lys Thr Gly Thr Leu Ala Ile Glu Ser Phe Val Val Asp Val Pro
            130                 135                 140

Glu Gly Asn Thr Lys Glu Thr Cys Phe Phe Val Glu Ala Leu Ile
145                 150                 155                 160

Gln Cys Asn Leu Asn Ser Leu Ala Asp Val Thr Glu Arg Leu Gln Ala
                165                 170                 175

Glu Ser Met Glu Lys Lys Ile
            180
```

<210> SEQ ID NO 12
<211> LENGTH: 161
<212> TYPE: PRT
<213> ORGANISM: Arabidopsis thaliana

<400> SEQUENCE: 12

```
Met Glu Thr Ser Gln Lys Tyr His Thr Cys Gly Ser Thr Leu Val Gln
1               5                   10                  15

Thr Ile Asp Ala Pro Leu Ser Leu Val Trp Ser Ile Leu Arg Arg Phe
                20                  25                  30

Asp Asn Pro Gln Ala Tyr Lys Gln Phe Val Lys Thr Cys Asn Leu Ser
            35                  40                  45

Ser Gly Asp Gly Gly Glu Gly Ser Val Arg Glu Val Thr Val Val Ser
        50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
                100                 105                 110

Glu Lys Thr Val Val Val Glu Ser Tyr Val Val Asp Val Pro Glu Gly
            115                 120                 125

Asn Ser Glu Glu Glu Thr Thr Ser Phe Ala Asp Thr Ile Val Gly Phe
        130                 135                 140

Asn Leu Lys Ser Leu Ala Lys Leu Ser Glu Arg Val Ala His Leu Lys
145                 150                 155                 160

Leu
```

<210> SEQ ID NO 13
<211> LENGTH: 159
<212> TYPE: PRT
<213> ORGANISM: Arabidopsis thaliana

<400> SEQUENCE: 13

```
Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
                20                  25                  30

Asp Asn Pro Lys Thr Phe Lys His Phe Val Lys Thr Cys Lys Leu Arg
            35                  40                  45
```

```
Ser Gly Asp Gly Gly Glu Gly Ser Val Arg Glu Val Thr Val Val Ser
    50                  55                  60

Asp Leu Pro Ala Ser Phe Ser Leu Glu Arg Leu Asp Glu Leu Asp Asp
 65                  70                  75                  80

Glu Ser His Val Met Val Ile Ser Ile Ile Gly Gly Asp His Arg Leu
                 85                  90                  95

Val Asn Tyr Gln Ser Lys Thr Thr Val Phe Val Ala Ala Glu Glu Glu
                100                 105                 110

Lys Thr Val Val Glu Ser Tyr Val Val Asp Val Pro Glu Gly Asn
            115                 120                 125

Thr Glu Glu Glu Thr Thr Leu Phe Ala Asp Thr Ile Val Gly Cys Asn
    130                 135                 140

Leu Arg Ser Leu Ala Lys Leu Ser Glu Lys Met Met Glu Leu Thr
145                 150                 155
```

<210> SEQ ID NO 14
<211> LENGTH: 164
<212> TYPE: PRT
<213> ORGANISM: Arabidopsis thaliana

<400> SEQUENCE: 14

```
Met Glu Ser Ser Lys Gln Lys Arg Cys Arg Ser Ser Val Val Glu Thr
 1               5                  10                  15

Ile Glu Ala Pro Leu Pro Leu Val Trp Ser Ile Leu Arg Ser Phe Asp
                20                  25                  30

Lys Pro Gln Ala Tyr Gln Arg Phe Val Lys Ser Cys Thr Met Arg Ser
            35                  40                  45

Gly Gly Gly Gly Gly Lys Gly Glu Gly Lys Gly Ser Val Arg Asp
    50                  55                  60

Val Thr Leu Val Ser Gly Phe Pro Ala Asp Phe Ser Thr Glu Arg Leu
 65                  70                  75                  80

Glu Glu Leu Asp Asp Gly Ser His Val Met Val Val Ser Ile Ile Gly
                 85                  90                  95

Gly Asn His Arg Leu Val Asn Tyr Lys Ser Lys Thr Lys Val Val Ala
                100                 105                 110

Ser Pro Glu Asp Met Ala Lys Lys Thr Val Val Glu Ser Tyr Val
            115                 120                 125

Val Asp Val Pro Glu Gly Thr Ser Glu Glu Asp Thr Ile Phe Phe Val
    130                 135                 140

Asp Asn Ile Ile Arg Tyr Asn Leu Thr Ser Leu Ala Lys Leu Thr Lys
145                 150                 155                 160

Lys Met Met Lys
```

<210> SEQ ID NO 15
<211> LENGTH: 191
<212> TYPE: PRT
<213> ORGANISM: Brassica oleracea

<400> SEQUENCE: 15

```
Met Pro Ser Gln Leu Thr Pro Glu Glu Arg Ser Glu Leu Ala Gln Ser
 1               5                  10                  15

Ile Ala Glu Phe His Thr Tyr His Leu Gly Pro Gly Ser Cys Ser Ser
                20                  25                  30

Leu His Ala Gln Arg Ile His Ala Pro Pro Glu Ile Val Trp Ser Val
            35                  40                  45
```

```
Val Arg Arg Phe Asp Lys Pro Gln Thr Tyr Lys His Phe Ile Lys Ser
    50                  55                  60

Cys Ser Val Glu Asp Gly Phe Glu Met Arg Val Gly Cys Thr Arg Ala
65                  70                  75                  80

Val Asn Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Val His Arg
                115                 120                 125

Phe Glu Lys Glu Arg Arg Ile Trp Thr Val Val Leu Glu Ser Tyr Val
    130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Ser Gly Ala Gln Val Thr
                180                 185                 190

<210> SEQ ID NO 16
<211> LENGTH: 281
<212> TYPE: PRT
<213> ORGANISM: Brassica oleracea

<400> SEQUENCE: 16

Met Pro Ser Glu Leu Thr Gln Glu Glu Arg Ser Lys Leu Thr Gln Ser
1               5                   10                  15

Ile Ser Glu Phe His Thr Tyr His Leu Gly Pro Gly Ser Cys Ser Ser
                20                  25                  30

Leu His Ala Gln Arg Ile His Ala Pro Pro Glu Ile Val Trp Ser Val
                35                  40                  45

Val Arg Gln Phe Asp Lys Pro Gln Thr Tyr Lys His Phe Ile Lys Ser
    50                  55                  60

Cys Ser Val Glu Glu Gly Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Met Leu Asp Asp Glu Arg Arg Val Thr Gly Phe Ser Ile Ile Gly
                100                 105                 110

Gly Glu His Arg Leu Lys Asn Tyr Lys Ser Val Thr Thr Val His Arg
                115                 120                 125

Phe Glu Arg Glu Arg Arg Ile Trp Thr Val Val Leu Glu Ser Tyr Val
    130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Arg Gly Ser Arg Glu Thr Thr
                180                 185                 190

Cys Arg Glu Ser Phe His Leu Ile Thr Ala Phe Glu Lys Gln Arg Gln
                195                 200                 205

Ile Thr Glu Pro Thr Val Tyr Gln Asn Pro Tyr His Thr Gly Met
    210                 215                 220

Thr Pro Glu Pro Arg Thr Ser Thr Val Phe Ile Glu Leu Glu Asp His
225                 230                 235                 240
```

Arg Thr Leu Pro Gly Asn Leu Thr Pro Thr Thr Glu Glu His Leu Gln
                245                 250                 255

Arg Met Tyr Gln Arg Phe Trp Gly Ile Arg Gln Leu Gln Arg Pro Arg
            260                 265                 270

Gln Ser Phe Gly Glu Arg Gln Ser Ile
        275                 280

<210> SEQ ID NO 17
<211> LENGTH: 453
<212> TYPE: PRT
<213> ORGANISM: Vitis vinifera

<400> SEQUENCE: 17

Met Gln Met Lys Tyr Leu Glu Gly Lys Gln Asn Leu Met Glu Glu Lys
1               5                   10                  15

Gly Glu Lys Gln Cys Ile Pro Met Asp Leu Ala Val Arg Glu Ala Gln
            20                  25                  30

Phe Lys Gly Ser Leu Leu Asp Arg Ile Thr Trp Leu Glu Gln Arg Leu
        35                  40                  45

His Lys Leu Ser Leu Gln Leu Glu Thr Arg Ser Lys Gln Gln Pro His
    50                  55                  60

Pro Ser Arg Met Gln Thr Ala Gly Glu Thr Ser Ser Arg His Gly Pro
65                  70                  75                  80

Lys Lys Glu Leu Ser Cys Ser Phe Pro Val Phe Ser Thr Arg Asn His
                85                  90                  95

Asn His Gly His Lys Gln Thr Ser Gln Phe His Val Pro Arg Phe Glu
            100                 105                 110

Tyr Gln Glu Gly Gly Arg Glu Asn Pro Ala Val Val Ile Thr Lys Leu
        115                 120                 125

Thr Pro Phe His His Pro Lys Ile Ile Thr Ile Leu Phe Pro Ile Ser
    130                 135                 140

Asn Tyr Phe Ile Ile Phe Phe Leu Thr Phe Asp Thr Lys Lys Gln
145                 150                 155                 160

Tyr Pro Leu Leu Phe Pro Ile Leu Pro Ser Arg Phe Leu Pro Ile Ser
                165                 170                 175

His Leu Ile Thr Gln Glu Ile Glu Lys Tyr Lys Thr Ser Ser His Phe
            180                 185                 190

Ser Ser Pro Ala Ser Leu Phe Ala Ala Met Asn Lys Ala Glu Thr Ser
        195                 200                 205

Ser Met Ala Glu Ala Glu Ser Glu Asp Ser Glu Thr Thr Thr Pro Thr
    210                 215                 220

Thr His His Leu Thr Ile Pro Pro Gly Leu Thr Gln Pro Glu Phe Gln
225                 230                 235                 240

Glu Leu Ala His Ser Ile Ser Glu Phe His Thr Tyr Gln Val Gly Pro
                245                 250                 255

Gly Gln Cys Ser Ser Leu Leu Ala Gln Arg Val His Ala Pro Leu Pro
            260                 265                 270

Thr Val Trp Ser Val Val Arg Arg Phe Asp Lys Pro Gln Thr Tyr Lys
        275                 280                 285

His Phe Ile Lys Ser Cys His Val Glu Asp Gly Phe Glu Met Arg Val
    290                 295                 300

Gly Cys Leu Arg Asp Val Asn Val Ile Ser Gly Leu Pro Ala Glu Thr
305                 310                 315                 320

Ser Thr Glu Arg Leu Asp Ile Leu Asp Asp Glu Arg His Val Thr Gly

```
            325                 330                 335
Phe Ser Ile Ile Gly Gly Glu His Arg Leu Arg Asn Tyr Arg Ser Val
        340                 345                 350

Thr Thr Asn His Gly Gly Glu Ile Trp Thr Val Val Leu Glu Ser Tyr
        355                 360                 365

Val Val Asp Met Pro Glu Gly Asn Thr Glu Glu Asp Thr Arg Leu Phe
370                 375                 380

Ala Asp Thr Val Val Lys Leu Asn Leu Gln Lys Leu Ala Ser Val Thr
385                 390                 395                 400

Glu Val Ser Gln Ser Cys Asn Tyr Pro Cys Gln Phe His Ile Ile Glu
            405                 410                 415

Asn Glu Asp Ile Gln Pro Glu Met Asn Leu Gly Val Leu Thr Thr
            420                 425                 430

Ser Ile Glu Glu Gln Arg Lys Lys Lys Arg Val Val Ala Met Lys Asp
            435                 440                 445

Gly Ser Thr Ser Ser
        450

<210> SEQ ID NO 18
<211> LENGTH: 195
<212> TYPE: PRT
<213> ORGANISM: Vitis vinifera
<220> FEATURE:
<221> NAME/KEY: VARIANT
<222> LOCATION: (193)..(193)
<223> OTHER INFORMATION: Xaa = any amino acid

<400> SEQUENCE: 18

Met Ala Glu Ala Glu Ser Glu Asp Ser Glu Thr Thr Thr Pro Thr Thr
1               5                   10                  15

His His Leu Thr Ile Pro Pro Gly Leu Thr Gln Pro Glu Phe Gln Glu
            20                  25                  30

Leu Ala His Ser Ile Ser Glu Phe His Thr Tyr Gln Val Gly Pro Gly
        35                  40                  45

Gln Cys Ser Ser Leu Leu Ala Gln Arg Val His Ala Pro Leu Pro Thr
    50                  55                  60

Val Trp Ser Val Val Arg Arg Phe Asp Lys Pro Gln Thr Tyr Lys His
65                  70                  75                  80

Phe Ile Lys Ser Cys His Val Glu Asp Gly Phe Glu Met Arg Val Gly
                85                  90                  95

Cys Leu Arg Asp Val Asn Val Ile Ser Gly Leu Pro Ala Glu Thr Ser
            100                 105                 110

Thr Glu Arg Leu Asp Ile Leu Asp Asp Glu Arg His Val Thr Gly Phe
        115                 120                 125

Ser Ile Ile Gly Gly Glu His Arg Leu Arg Asn Tyr Arg Ser Val Thr
    130                 135                 140

Thr Val His Glu Tyr Gln Asn His Gly Gly Glu Ile Trp Thr Val Val
145                 150                 155                 160

Leu Glu Ser Tyr Val Val Asp Met Pro Glu Gly Asn Thr Glu Glu Asp
                165                 170                 175

Thr Arg Leu Phe Ala Asp Thr Val Val Lys Leu Asn Leu Ser Glu Ala
            180                 185                 190

Xaa Arg Arg
    195

<210> SEQ ID NO 19
```

<211> LENGTH: 217
<212> TYPE: PRT
<213> ORGANISM: Medicago truncatula

<400> SEQUENCE: 19

```
Met Glu Lys Ala Glu Ser Ser Thr Ala Ser Thr Ser Asp Gln Asp Ser
1               5                   10                  15

Asp Glu Asn His Arg Thr Gln His His Leu Thr Leu Pro Ser Gly Leu
            20                  25                  30

Arg Gln His Glu Phe Asp Ser Leu Ile Pro Phe Ile Asn Ser His His
        35                  40                  45

Thr Tyr Leu Ile Gly Pro Asn Gln Cys Ser Thr Leu Leu Ala Gln Arg
50                  55                  60

Ile His Ala Pro Pro Gln Thr Val Trp Ser Val Val Arg Ser Phe Asp
65                  70                  75                  80

Lys Pro Gln Ile Tyr Lys His Ile Ile Lys Ser Cys Ser Leu Lys Glu
                85                  90                  95

Gly Phe Gln Met Lys Val Gly Cys Thr Arg Asp Val Asn Val Ile Ser
            100                 105                 110

Gly Leu Pro Ala Ala Thr Ser Thr Glu Arg Leu Asp Val Leu Asp Asp
        115                 120                 125

Glu Arg Arg Val Thr Gly Phe Ser Ile Ile Gly Gly Glu His Arg Leu
130                 135                 140

Lys Asn Tyr Arg Ser Val Thr Ser Val His Gly Phe Gly Asp Gly Asp
145                 150                 155                 160

Asn Gly Gly Glu Ile Trp Thr Val Val Leu Glu Ser Tyr Val Val Asp
                165                 170                 175

Val Pro Glu Gly Asn Thr Glu Glu Asp Thr Arg Leu Phe Ala Asp Thr
            180                 185                 190

Val Val Lys Leu Asn Leu Gln Lys Leu Ala Ser Val Thr Glu Gly Lys
        195                 200                 205

Asn Arg Asp Gly Asp Gly Lys Ser His
210                 215
```

<210> SEQ ID NO 20
<211> LENGTH: 212
<212> TYPE: PRT
<213> ORGANISM: Oryza sativa

<400> SEQUENCE: 20

```
Met Glu Gln Gln Glu Glu Val Pro Pro Pro Ala Gly Leu Gly Leu
1               5                   10                  15

Thr Ala Glu Glu Tyr Ala Gln Val Arg Ala Thr Val Glu Ala His His
            20                  25                  30

Arg Tyr Ala Val Gly Pro Gly Gln Cys Ser Ser Leu Leu Ala Gln Arg
        35                  40                  45

Ile His Ala Pro Pro Ala Ala Val Trp Ala Val Val Arg Arg Phe Asp
50                  55                  60

Cys Pro Gln Val Tyr Lys His Phe Ile Arg Ser Cys Val Leu Arg Pro
65                  70                  75                  80

Asp Pro His His Asp Asp Asn Gly Asn Asp Leu Arg Pro Gly Arg Leu
                85                  90                  95

Arg Glu Val Ser Val Ile Ser Gly Leu Pro Ala Ser Thr Ser Thr Glu
            100                 105                 110

Arg Leu Asp Leu Leu Asp Asp Ala His Arg Val Phe Gly Phe Thr Ile
        115                 120                 125
```

```
Thr Gly Gly Glu His Arg Leu Arg Asn Tyr Arg Ser Val Thr Thr Val
        130                 135                 140

Ser Gln Leu Asp Glu Ile Cys Thr Leu Val Leu Glu Ser Tyr Ile Val
145                 150                 155                 160

Asp Val Pro Asp Gly Asn Thr Glu Asp Thr Arg Leu Phe Ala Asp
                165                 170                 175

Thr Val Ile Arg Leu Asn Leu Gln Lys Leu Lys Ser Val Ser Glu Ala
            180                 185                 190

Asn Ala Asn Ala Ala Ala Ala Ala Ala Pro Pro Pro Pro Pro
        195                 200                 205

Ala Ala Ala Glu
        210

<210> SEQ ID NO 21
<211> LENGTH: 212
<212> TYPE: PRT
<213> ORGANISM: Zea mays

<400> SEQUENCE: 21

Met Asp Gln Gln Gly Ala Gly Gly Asp Ala Glu Val Pro Ala Gly Leu
1               5                   10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
    50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
            100                 105                 110

Leu Asp Leu Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
    130                 135                 140

Glu Leu Ala Val Pro Ala Ile Cys Thr Val Val Leu Glu Ser Tyr Val
145                 150                 155                 160

Val Asp Val Pro Asp Gly Asn Thr Glu Asp Thr Arg Leu Phe Ala
                165                 170                 175

Asp Thr Val Ile Arg Leu Asn Leu Gln Lys Leu Lys Ser Val Ala Glu
            180                 185                 190

Ala Asn Ala Ala Glu Ala Ala Thr Thr Asn Ser Val Leu Leu Pro
        195                 200                 205

Arg Pro Ala Glu
        210

<210> SEQ ID NO 22
<211> LENGTH: 212
<212> TYPE: PRT
<213> ORGANISM: Zea mays
<220> FEATURE:
<221> NAME/KEY: VARIANT
<222> LOCATION: (11)..(11)
<223> OTHER INFORMATION: Xaa = any amino acid
```

<400> SEQUENCE: 22

```
Met Asp Gln Gln Gly Ala Gly Asp Ala Xaa Val Pro Ala Gly Leu
1               5                   10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
    50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Thr Glu Arg
            100                 105                 110

Leu Asp Leu Leu Asp Asp Ala Ala Arg Val Phe Gly Phe Ser Ile Thr
            115                 120                 125

Gly Gly Glu His Arg Leu Arg Asn Tyr Arg Ser Val Thr Thr Val Ser
130                 135                 140

Glu Leu Ala Asp Pro Ala Ile Cys Thr Val Val Leu Glu Ser Tyr Val
145                 150                 155                 160

Val Asp Val Pro Asp Gly Asn Thr Glu Asp Thr Arg Leu Phe Ala
                165                 170                 175

Asp Thr Val Ile Arg Leu Asn Leu Gln Lys Leu Lys Ser Val Thr Glu
            180                 185                 190

Ala Asn Ala Ala Glu Ala Ala Thr Thr Asn Ser Val Leu Leu Pro
        195                 200                 205

Arg Pro Ala Glu
    210
```

<210> SEQ ID NO 23
<211> LENGTH: 233
<212> TYPE: PRT
<213> ORGANISM: Vitis vinifera

<400> SEQUENCE: 23

```
Met Asp Pro His His His His Gly Leu Thr Glu Glu Glu Phe Arg Ala
1               5                   10                  15

Leu Glu Pro Ile Ile Gln Asn Tyr His Thr Phe Glu Pro Ser Pro Asn
            20                  25                  30

Thr Cys Thr Ser Leu Ile Thr Gln Lys Ile Asp Ala Pro Ala Gln Val
        35                  40                  45

Val Trp Pro Phe Val Arg Ser Phe Glu Asn Pro Gln Lys Tyr Lys His
    50                  55                  60

Phe Ile Lys Asp Cys Thr Met Arg Gly Asp Gly Val Gly Ser Ile
65                  70                  75                  80

Arg Glu Val Thr Val Val Ser Gly Leu Pro Ala Ser Thr Ser Thr Glu
                85                  90                  95

Arg Leu Glu Ile Leu Asp Asp Glu Lys His Ile Leu Ser Phe Arg Val
            100                 105                 110

Val Gly Gly Glu His Arg Leu Asn Asn Tyr Arg Ser Val Thr Ser Val
        115                 120                 125

Asn Asp Phe Ser Lys Glu Gly Lys Asp Tyr Thr Ile Val Leu Glu Ser
    130                 135                 140
```

```
Tyr Ile Val Asp Ile Pro Glu Gly Asn Thr Gly Glu Asp Thr Lys Met
145                 150                 155                 160

Phe Val Asp Thr Val Val Lys Leu Asn Leu Gln Lys Leu Ala Val Val
                165                 170                 175

Ala Ile Thr Ser Leu His Glu Asn Glu Glu Ile Ala Asp Asn Glu Gly
            180                 185                 190

Pro Ser Arg Glu Ile Ser Leu Gln Ser Glu Thr Glu Ser Ala Glu Arg
        195                 200                 205

Gly Asp Glu Arg Arg Asp Gly Asp Gly Pro Ser Lys Ala Cys Asn Arg
    210                 215                 220

Asn Glu Trp His Cys Thr Thr Lys Glu
225                 230

<210> SEQ ID NO 24
<211> LENGTH: 207
<212> TYPE: PRT
<213> ORGANISM: Oryza sativa

<400> SEQUENCE: 24

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
65                  70                  75                  80

Ser Cys Glu Leu Ala Ala Gly Asp Gly Ala Thr Val Gly Ser Val Arg
                85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
        115                 120                 125

Gly Gly Asp His Arg Leu Arg Asn Tyr Arg Ser Val Thr Ser Val Thr
    130                 135                 140

Glu Phe Ser Ser Pro Ser Ser Pro Arg Pro Tyr Cys Val Val Val
145                 150                 155                 160

Glu Ser Tyr Val Val Asp Val Pro Glu Gly Asn Thr Glu Glu Asp Thr
                165                 170                 175

Arg Met Phe Thr Asp Thr Val Val Lys Leu Asn Leu Gln Lys Leu Ala
            180                 185                 190

Ala Val Ala Thr Ser Ser Ser Pro Pro Ala Ala Gly Asn His His
        195                 200                 205

<210> SEQ ID NO 25
<211> LENGTH: 210
<212> TYPE: PRT
<213> ORGANISM: Oryza sativa

<400> SEQUENCE: 25

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30
```

```
Pro Ala Ala Glu Arg Ala Ala Gly Pro Gly Arg Pro Thr Cys Thr
            35                  40                  45

Ser Leu Val Ala Gln Arg Val Asp Ala Pro Leu Ala Val Trp Pro
 50                  55                  60

Ile Val Arg Gly Phe Ala Asn Pro Gln Arg Tyr Lys His Phe Ile Lys
 65                  70                  75                  80

Ser Cys Glu Leu Ala Ala Gly Asp Gly Ala Thr Val Gly Ser Val Arg
                 85                  90                  95

Glu Val Ala Val Val Ser Gly Leu Pro Ala Ser Thr Ser Thr Glu Arg
                100                 105                 110

Leu Glu Ile Leu Asp Asp Asp Arg His Val Leu Ser Phe Arg Val Val
                115                 120                 125

Gly Gly Asp His Arg Leu Arg Asn Tyr Arg Ser Val Thr Ser Val Thr
    130                 135                 140

Glu Phe Ser Ser Pro Ser Ser Pro Ser Pro Arg Pro Tyr Cys
145                 150                 155                 160

Val Val Val Glu Ser Tyr Val Val Asp Val Pro Glu Gly Asn Thr Glu
                165                 170                 175

Glu Asp Thr Arg Met Phe Thr Asp Thr Val Val Lys Leu Asn Leu Gln
            180                 185                 190

Lys Leu Ala Ala Val Ala Thr Ser Ser Ser Pro Pro Ala Ala Gly Asn
            195                 200                 205

His His
    210

<210> SEQ ID NO 26
<211> LENGTH: 200
<212> TYPE: PRT
<213> ORGANISM: Zea mays

<400> SEQUENCE: 26

Met Pro Tyr Thr Ala Pro Arg Pro Ser Pro Gln Gln His Ser Arg Val
  1               5                  10                  15

Leu Ser Gly Gly Gly Ala Lys Ala Ala Ser His Gly Ala Ser Cys Ala
                 20                  25                  30

Ala Val Pro Ala Glu Val Ala Arg His His Glu His Ala Ala Arg Ala
             35                  40                  45

Gly Gln Cys Cys Ser Ala Val Val Gln Ala Ile Ala Ala Pro Val Gly
 50                  55                  60

Ala Val Trp Ser Val Val Arg Arg Phe Asp Arg Pro Gln Ala Tyr Lys
 65                  70                  75                  80

His Phe Ile Arg Ser Cys Arg Leu Val Gly Gly Asp Val Ala Val
                 85                  90                  95

Gly Ser Val Arg Glu Val Arg Val Val Ser Gly Leu Pro Ala Thr Ser
                100                 105                 110

Ser Arg Glu Arg Leu Glu Ile Leu Asp Asp Glu Arg Arg Val Leu Ser
            115                 120                 125

Phe Arg Val Val Gly Gly Glu His Arg Leu Ala Asn Tyr Arg Ser Val
    130                 135                 140

Thr Thr Val His Glu Ala Gly Ala Gly Thr Gly Thr Val Val
145                 150                 155                 160

Val Glu Ser Tyr Val Val Asp Val Pro His Gly Asn Thr Ala Asp Glu
                165                 170                 175

Thr Arg Val Phe Val Asp Thr Ile Val Arg Cys Asn Leu Gln Ser Leu
            180                 185                 190
```

```
Ala Arg Thr Ala Glu Arg Leu Ala
        195                 200

<210> SEQ ID NO 27
<211> LENGTH: 215
<212> TYPE: PRT
<213> ORGANISM: Vitis vinifera

<400> SEQUENCE: 27

Met Pro Ser Asn Pro Lys Ser Ser Leu Val Val His Arg Ile Asn
1               5                   10                  15

Ser Pro Asn Ser Ile Thr Thr Ala Thr Thr Ala Ser Ala Ala Asn
            20                  25                  30

Asn His Asn Thr Ser Thr Met Pro Pro His Lys Gln Val Pro Asp Ala
        35                  40                  45

Val Ser Arg His His Thr His Val Gly Pro Asn Gln Cys Cys Ser
    50                  55                  60

Ala Val Val Gln Gln Ile Ala Pro Val Ser Thr Val Trp Ser Val
65                  70                  75                  80

Val Arg Arg Phe Asp Asn Pro Gln Ala Tyr Lys His Phe Val Lys Ser
                85                  90                  95

Cys His Val Val Val Gly Asp Gly Asp Val Gly Thr Leu Arg Glu Val
                100                 105                 110

His Val Ile Ser Gly Leu Pro Ala Ala Asn Ser Thr Glu Arg Leu Glu
                115                 120                 125

Ile Leu Asp Asp Glu Arg His Val Leu Ser Phe Ser Val Ile Gly Gly
130                 135                 140

Asp His Arg Leu Ser Asn Tyr Arg Ser Val Thr Thr Leu His Pro Ser
145                 150                 155                 160

Pro Ser Ser Thr Gly Thr Val Val Leu Glu Ser Tyr Val Val Asp Ile
                165                 170                 175

Pro Pro Gly Asn Thr Lys Glu Asp Thr Cys Val Phe Val Asp Thr Ile
                180                 185                 190

Val Arg Cys Asn Leu Gln Ser Leu Ala Gln Ile Ala Glu Asn Ala Ala
                195                 200                 205

Gly Cys Lys Arg Ser Ser
        210             215

<210> SEQ ID NO 28
<211> LENGTH: 213
<212> TYPE: PRT
<213> ORGANISM: Nicotiana tabacum

<400> SEQUENCE: 28

Met Pro Pro Ser Ser Pro Asp Ser Ser Val Leu Leu Gln Arg Ile Ser
1               5                   10                  15

Ser Asn Thr Thr Pro Asp Phe Ala Cys Lys Gln Ser Gln Gln Leu Gln
            20                  25                  30

Arg Arg Thr Met Pro Ile Pro Cys Thr Thr Gln Val Pro Asp Ser Val
        35                  40                  45

Val Arg Phe His Thr His Pro Val Gly Pro Asn Gln Cys Cys Ser Ala
    50                  55                  60

Val Ile Gln Arg Ile Ser Ala Pro Val Ser Thr Val Trp Ser Val Val
65                  70                  75                  80

Arg Arg Phe Asp Asn Pro Gln Ala Tyr Lys His Phe Val Lys Ser Cys
                85                  90                  95
```

```
His Val Ile Val Gly Asp Gly Asp Val Gly Thr Leu Arg Glu Val Arg
                100                 105                 110

Val Ile Ser Gly Leu Pro Ala Ala Ser Ser Thr Glu Arg Leu Glu Ile
            115                 120                 125

Leu Asp Asp Glu Arg His Val Ile Ser Phe Ser Val Val Gly Gly Asp
        130                 135                 140

His Arg Leu Ala Asn Tyr Arg Ser Val Thr Thr Leu His Pro Glu Pro
145                 150                 155                 160

Ser Gly Asp Gly Thr Thr Ile Val Val Glu Ser Tyr Val Val Asp Val
                165                 170                 175

Pro Pro Gly Asn Thr Arg Asp Glu Thr Cys Val Phe Val Asp Thr Ile
            180                 185                 190

Val Lys Cys Asn Leu Thr Ser Leu Ser Gln Ile Ala Val Asn Val Asn
        195                 200                 205

Arg Arg Lys Asp Ser
    210

<210> SEQ ID NO 29
<211> LENGTH: 208
<212> TYPE: PRT
<213> ORGANISM: Oryza sativa

<400> SEQUENCE: 29

Met Pro Tyr Ala Ala Val Arg Pro Ser Pro Pro Gln Leu Ser Arg
1               5                   10                  15

Pro Ile Gly Ser Gly Ala Gly Gly Gly Lys Ala Cys Pro Ala Val Pro
            20                  25                  30

Cys Glu Val Ala Arg Tyr His Glu His Ala Val Gly Ala Gly Gln Cys
        35                  40                  45

Cys Ser Thr Val Val Gln Ala Ile Ala Ala Pro Ala Asp Ala Val Trp
    50                  55                  60

Ser Val Val Arg Arg Phe Asp Arg Pro Gln Ala Tyr Lys Lys Phe Ile
65                  70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
                100                 105                 110

Arg Leu Glu Val Leu Asp Asp Arg Arg Val Leu Ser Phe Arg Ile
            115                 120                 125

Val Gly Gly Glu His Arg Leu Ala Asn Tyr Arg Ser Val Thr Thr Val
        130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
            180                 185                 190

Arg Leu Ala Pro Glu Ala Pro Arg Ala Asn Gly Ser Ile Asp His Ala
        195                 200                 205

<210> SEQ ID NO 30
<211> LENGTH: 208
<212> TYPE: PRT
<213> ORGANISM: Oryza sativa

<400> SEQUENCE: 30
```

```
Met Pro Tyr Ala Ala Val Arg Pro Ser Pro Pro Gln Leu Ser Arg
1               5                   10                  15

Pro Ile Gly Ser Gly Ala Gly Gly Lys Ala Cys Pro Ala Val Pro
                20                  25                  30

Cys Glu Val Ala Arg Tyr His Glu His Ala Val Gly Ala Gly Gln Cys
            35                  40                  45

Phe Ser Thr Val Val Gln Ala Ile Ala Ala Pro Ala Asp Ala Val Trp
    50                  55                  60

Ser Val Val Arg Arg Phe Asp Arg Pro Gln Ala Tyr Lys Lys Phe Ile
65                  70                  75                  80

Lys Ser Cys Arg Leu Val Asp Gly Asp Gly Glu Val Gly Ser Val
                85                  90                  95

Arg Glu Val Arg Val Val Ser Gly Leu Pro Ala Thr Ser Ser Arg Glu
                100                 105                 110

Arg Leu Glu Val Leu Asp Asp Arg Arg Val Leu Ser Phe Arg Ile
            115                 120                 125

Val Gly Gly Glu His Arg Leu Ala Asn Tyr Arg Ser Val Thr Thr Val
    130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
            180                 185                 190

Arg Leu Ala Pro Glu Ala Pro Arg Ala Asn Gly Ser Ile Asp His Ala
            195                 200                 205
```

<210> SEQ ID NO 31
<211> LENGTH: 213
<212> TYPE: PRT
<213> ORGANISM: Picea sitchensis

<400> SEQUENCE: 31

```
Met Asp Ile Ile Ala Gly Phe Asp Gln Leu Ser Phe Arg Leu Ser Gly
1               5                   10                  15

Ala Ser Lys Gln Ile Thr Lys Thr Gly Ala Val Gln Tyr Leu Lys Gly
                20                  25                  30

Glu Glu Gly Tyr Gly Glu Trp Leu Lys Glu Val Met Gly Arg Tyr His
            35                  40                  45

Tyr His Ser His Asp Gly Ala Arg Glu Cys Arg Cys Ser Ser Val Val
    50                  55                  60

Val Gln Gln Val Glu Ala Pro Val Ser Val Val Trp Ser Leu Val Arg
65                  70                  75                  80

Arg Phe Asp Gln Pro Gln Val Tyr Lys His Phe Val Ser Asn Cys Phe
                85                  90                  95

Met Arg Gly Asp Leu Lys Val Gly Cys Leu Arg Glu Val Arg Val Val
                100                 105                 110

Ser Gly Leu Pro Ala Ala Thr Ser Thr Glu Arg Leu Asp Ile Leu Asp
            115                 120                 125

Glu Glu Arg His Ile Leu Ser Phe Ser Ile Val Gly Gly Asp His Arg
    130                 135                 140

Leu Asn Asn Tyr Arg Ser Ile Thr Thr Leu His Glu Thr Leu Ile Asn
145                 150                 155                 160

Gly Lys Pro Gly Thr Ile Val Ile Glu Ser Tyr Val Leu Asp Val Pro
```

165                 170                 175
His Gly Asn Thr Lys Glu Glu Thr Cys Leu Phe Val Asp Thr Ile Val
            180                 185                 190

Lys Cys Asn Leu Gln Ser Leu Ala His Val Ser Asn His Leu Asn Ser
        195                 200                 205

Thr His Arg Cys Leu
    210

<210> SEQ ID NO 32
<211> LENGTH: 207
<212> TYPE: PRT
<213> ORGANISM: Oryza sativa

<400> SEQUENCE: 32

Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asp Gly Ala Ser Val Gly Ser Val Arg Glu Val
                85                  90                  95

Thr Val Val Ser Gly Leu Pro Ala Ser Thr Ser Thr Glu Arg Leu Glu
            100                 105                 110

Met Leu Asp Asp Asp Arg His Ile Ile Ser Phe Arg Val Val Gly Gly
        115                 120                 125

Gln His Arg Leu Arg Asn Tyr Arg Ser Val Thr Ser Val Thr Glu Phe
    130                 135                 140

Gln Pro Pro Ala Ala Gly Pro Gly Pro Ala Pro Pro Tyr Cys Val Val
145                 150                 155                 160

Val Glu Ser Tyr Val Val Asp Val Pro Asp Gly Asn Thr Ala Glu Asp
                165                 170                 175

Thr Arg Met Phe Thr Asp Thr Val Lys Leu Asn Leu Gln Met Leu
            180                 185                 190

Ala Ala Val Ala Glu Asp Ser Ser Ser Ala Ser Arg Arg Arg Asp
        195                 200                 205

<210> SEQ ID NO 33
<211> LENGTH: 216
<212> TYPE: PRT
<213> ORGANISM: Oryza sativa

<400> SEQUENCE: 33

Met Pro Tyr Thr Ala Pro Arg Pro Ser Pro Gln His Ser Arg Ile
1               5                   10                  15

Gly Gly Cys Gly Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Ser Val Val Arg Arg Phe Asp

```
                65                  70                  75                  80
Arg Pro Gln Ala Tyr Lys His Phe Ile Arg Ser Cys Arg Leu Leu Asp
                    85                  90                  95

Gly Asp Gly Asp Gly Ala Val Ala Val Gly Ser Val Arg Glu Val
                100                 105                 110

Arg Val Val Ser Gly Leu Pro Ala Thr Ser Ser Arg Glu Arg Leu Glu
                115                 120                 125

Ile Leu Asp Asp Glu Arg Arg Val Leu Ser Phe Arg Val Val Gly Gly
        130                 135                 140

Glu His Arg Leu Ser Asn Tyr Arg Ser Val Thr Thr Val His Glu Thr
145                 150                 155                 160

Ala Ala Gly Ala Ala Ala Val Val Val Glu Ser Tyr Val Val Asp
                165                 170                 175

Val Pro His Gly Asn Thr Ala Asp Glu Thr Arg Met Phe Val Asp Thr
                180                 185                 190

Ile Val Arg Cys Asn Leu Gln Ser Leu Ala Arg Thr Ala Glu Gln Leu
                195                 200                 205

Ala Leu Ala Ala Pro Arg Ala Ala
        210                 215

<210> SEQ ID NO 34
<211> LENGTH: 212
<212> TYPE: PRT
<213> ORGANISM: Vitis vinifera

<400> SEQUENCE: 34

Met Pro Ser Ser Leu Gln Leu His Arg Ile Asn Asn Ile Asp Pro Thr
1               5                   10                  15

Thr Val Ala Val Ala Ala Thr Ala Ala Val Asn Cys His Lys Gln Ser
                20                  25                  30

Arg Thr Pro Leu Arg Cys Ala Thr Pro Val Pro Asp Ala Val Ala Ser
                35                  40                  45

Tyr His Ala His Ala Val Gly Pro His Gln Cys Cys Ser Met Val Val
        50                  55                  60

Gln Thr Thr Ala Ala Ala Leu Pro Thr Val Trp Ser Val Arg Arg
65                  70                  75                  80

Phe Asp Asn Pro Gln Ala Tyr Lys His Phe Leu Lys Ser Cys His Val
                85                  90                  95

Ile Phe Gly Asp Gly Asp Ile Gly Thr Leu Arg Glu Val His Val Val
                100                 105                 110

Ser Gly Leu Pro Ala Glu Ser Ser Thr Glu Arg Leu Glu Ile Leu Asp
                115                 120                 125

Asp Glu Arg His Val Leu Ser Phe Ser Val Val Gly Gly Asp His Arg
        130                 135                 140

Leu Cys Asn Tyr Arg Ser Val Thr Thr Leu His Pro Ser Pro Thr Gly
145                 150                 155                 160

Thr Gly Thr Val Val Val Glu Ser Tyr Val Val Asp Ile Pro Pro Gly
                165                 170                 175

Asn Thr Lys Glu Asp Thr Cys Val Phe Val Asp Thr Ile Val Lys Cys
                180                 185                 190

Asn Leu Gln Ser Leu Ala Gln Met Ser Glu Lys Leu Thr Asn Asn Asn
                195                 200                 205

Arg Asn Ser Ser
        210
```

<210> SEQ ID NO 35
<211> LENGTH: 218
<212> TYPE: PRT
<213> ORGANISM: Zea mays

<400> SEQUENCE: 35

Met Pro Cys Leu Gln Ala Ser Ser Pro Gly Ser Met Pro Tyr Gln His
1               5                   10                  15

His Gly Arg Gly Val Gly Cys Ala Ala Glu Ala Gly Ala Ala Val Gly
            20                  25                  30

Ala Ser Ala Gly Thr Gly Thr Arg Cys Gly Ala His Asp Gly Glu Val
        35                  40                  45

Pro Ala Glu Ala Ala Arg His His Glu His Ala Ala Pro Gly Pro Gly
    50                  55                  60

Arg Cys Cys Ser Ala Val Val Gln Arg Val Ala Pro Ala Glu Ala
65                  70                  75                  80

Val Trp Ser Val Val Arg Arg Phe Asp Gln Pro Gln Ala Tyr Lys Arg
                85                  90                  95

Phe Val Arg Ser Cys Ala Leu Leu Ala Gly Asp Gly Val Gly Thr
            100                 105                 110

Leu Arg Glu Val Arg Val Val Ser Gly Leu Pro Ala Ala Ser Ser Arg
        115                 120                 125

Glu Arg Leu Glu Val Leu Asp Asp Glu Ser His Val Leu Ser Phe Arg
    130                 135                 140

Val Val Gly Gly Glu His Arg Leu Gln Asn Tyr Leu Ser Val Thr Thr
145                 150                 155                 160

Val His Pro Ser Pro Ala Ala Pro Asp Ala Ala Thr Val Val Glu
                165                 170                 175

Ser Tyr Val Val Asp Val Pro Pro Gly Asn Thr Pro Glu Asp Thr Arg
            180                 185                 190

Val Phe Val Asp Thr Ile Val Lys Cys Asn Leu Gln Ser Leu Ala Thr
        195                 200                 205

Thr Ala Glu Lys Leu Ala Leu Ala Ala Val
    210                 215

<210> SEQ ID NO 36
<211> LENGTH: 179
<212> TYPE: PRT
<213> ORGANISM: Physcomitrella patens

<400> SEQUENCE: 36

Met Gln Thr Lys Gly Arg Gln Ala Asp Phe Gln Thr Leu Leu Glu Gly
1               5                   10                  15

Gln Gln Asp Leu Ile Cys Arg Phe His Arg His Glu Leu Gln Pro His
            20                  25                  30

Gln Cys Gly Ser Ile Leu Leu Gln Leu Ile Lys Ala Pro Val Glu Thr
        35                  40                  45

Val Trp Ser Val Ala Arg Ser Phe Asp Lys Pro Gln Val Tyr Lys Arg
    50                  55                  60

Phe Ile Gln Thr Cys Glu Ile Ile Glu Gly Asp Gly Val Gly Ser
65                  70                  75                  80

Ile Arg Glu Val Arg Leu Val Ser Ser Ile Pro Ala Thr Ser Ser Ile
                85                  90                  95

Glu Arg Leu Glu Ile Leu Asp Asp Glu Glu His Ile Ile Ser Phe Arg
            100                 105                 110

Val Leu Gly Gly Gly His Arg Leu Gln Asn Tyr Trp Ser Val Thr Ser
            115                 120                 125

Leu His Ser His Glu Ile Asp Gly Gln Met Gly Thr Leu Val Leu Glu
        130                 135                 140

Ser Tyr Val Val Asp Ile Pro Glu Gly Asn Thr Arg Glu Thr His
145                 150                 155                 160

Met Phe Val Asp Thr Val Val Arg Cys Asn Leu Lys Ala Leu Ala Gln
                165                 170                 175

Val Ser Glu

<210> SEQ ID NO 37
<211> LENGTH: 229
<212> TYPE: PRT
<213> ORGANISM: Oryza sativa

<400> SEQUENCE: 37

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Gln His
65                  70                  75                  80

Val Ala Ala Pro Ala Pro Ala Val Trp Ser Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225

<210> SEQ ID NO 38
<211> LENGTH: 229
<212> TYPE: PRT
<213> ORGANISM: Oryza sativa

<400> SEQUENCE: 38

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys

```
                    20                  25                  30
Ala Ala Glu Ala Ala Val Ala Ala Gly Val Ala Gly Thr Arg Cys
                35                  40                  45
Gly Ala His Asp Gly Glu Val Pro Met Glu Val Ala Arg His His Glu
 50                  55                  60
His Ala Glu Pro Gly Ser Gly Arg Cys Cys Ser Ala Val Val Gln His
 65                  70                  75                  80
Val Ala Ala Pro Ala Ala Ala Val Trp Ser Val Val Arg Arg Phe Asp
                 85                  90                  95
Gln Pro Gln Ala Tyr Lys Arg Phe Val Arg Ser Cys Ala Leu Leu Ala
                100                 105                 110
Gly Asp Gly Val Gly Thr Leu Arg Glu Val Arg Val Val Ser Gly
                115                 120                 125
Leu Pro Ala Ala Ser Ser Arg Glu Arg Leu Glu Ile Leu Asp Asp Glu
                130                 135                 140
Ser His Val Leu Ser Phe Arg Val Val Gly Gly Glu His Arg Leu Lys
145                 150                 155                 160
Asn Tyr Leu Ser Val Thr Thr Val His Pro Ser Pro Ser Ala Pro Thr
                165                 170                 175
Ala Ala Thr Val Val Glu Ser Tyr Val Val Asp Val Pro Pro Gly
                180                 185                 190
Asn Thr Pro Glu Asp Thr Arg Val Phe Val Asp Thr Ile Val Lys Cys
                195                 200                 205
Asn Leu Gln Ser Leu Ala Lys Thr Ala Glu Lys Leu Ala Ala Gly Ala
                210                 215                 220
Arg Ala Ala Gly Ser
225

<210> SEQ ID NO 39
<211> LENGTH: 205
<212> TYPE: PRT
<213> ORGANISM: Medicago truncatula

<400> SEQUENCE: 39

Met Pro Ser Pro Val Gln Phe Gln Arg Phe Asp Ser Asn Thr Ala Ile
 1               5                  10                  15
Thr Asn Gly Val Asn Cys Pro Lys Gln Ile Gln Ala Cys Arg Tyr Ala
                20                  25                  30
Leu Ser Ser Leu Lys Pro Thr Val Ser Val Pro Glu Thr Val Val Asp
                35                  40                  45
His His Met His Val Val Gly Gln Asn Gln Cys Tyr Ser Val Val Ile
 50                  55                  60
Gln Thr Ile Asn Ala Ser Val Ser Thr Val Trp Ser Val Val Arg Arg
 65                  70                  75                  80
Phe Asp Tyr Pro Gln Gly Tyr Lys His Phe Val Lys Ser Cys Asn Val
                 85                  90                  95
Val Ala Ser Gly Asp Gly Ile Arg Val Gly Ala Leu Arg Glu Val Arg
                100                 105                 110
Leu Val Ser Gly Leu Pro Ala Val Ser Ser Thr Glu Arg Leu Asp Ile
                115                 120                 125
Leu Asp Glu Glu Arg His Val Ile Ser Phe Ser Val Val Gly Gly Val
                130                 135                 140
His Arg Cys Arg Asn Tyr Arg Ser Val Thr Thr Leu His Gly Asp Gly
145                 150                 155                 160
```

```
Asn Gly Gly Thr Val Val Ile Glu Ser Tyr Val Val Asp Val Pro Gln
                165                 170                 175

Gly Asn Thr Lys Glu Glu Thr Cys Ser Phe Ala Asp Thr Ile Val Arg
            180                 185                 190

Cys Asn Leu Gln Ser Leu Val Gln Ile Ala Glu Lys Leu
        195                 200                 205
```

<210> SEQ ID NO 40
<211> LENGTH: 212
<212> TYPE: PRT
<213> ORGANISM: Zea mays

<400> SEQUENCE: 40

```
Met Pro Phe Ala Ala Ser Arg Thr Ser Gln Gln Gln His Ser Arg Val
1               5                   10                  15

Ala Thr Asn Gly Arg Ala Val Ala Val Cys Ala Gly His Ala Gly Val
            20                  25                  30

Pro Asp Glu Val Ala Arg His His Glu His Ala Val Ala Ala Gly Gln
        35                  40                  45

Cys Cys Ala Ala Met Val Gln Ser Ile Ala Ala Pro Val Asp Ala Val
50                  55                  60

Trp Ser Leu Val Arg Arg Phe Asp Gln Pro Gln Arg Tyr Lys Arg Phe
65                  70                  75                  80

Ile Arg Ser Cys His Leu Val Asp Gly Asp Gly Ala Glu Val Gly Ser
                85                  90                  95

Val Arg Glu Leu Leu Leu Val Ser Gly Leu Pro Ala Glu Ser Ser Arg
            100                 105                 110

Glu Arg Leu Glu Ile Arg Asp Asp Glu Arg Arg Val Ile Ser Phe Arg
        115                 120                 125

Val Leu Gly Gly Asp His Arg Leu Ala Asn Tyr Arg Ser Val Thr Thr
130                 135                 140

Val His Glu Ala Ala Pro Ser Gln Asp Gly Arg Pro Leu Thr Met Val
145                 150                 155                 160

Val Glu Ser Tyr Val Val Asp Val Pro Pro Gly Asn Thr Val Glu Glu
                165                 170                 175

Thr Arg Ile Phe Val Asp Thr Ile Val Arg Cys Asn Leu Gln Ser Leu
            180                 185                 190

Glu Gly Thr Val Ile Arg Gln Leu Glu Ile Ala Ala Met Pro His Asp
        195                 200                 205

Asp Asn Gln Asn
    210
```

<210> SEQ ID NO 41
<211> LENGTH: 233
<212> TYPE: PRT
<213> ORGANISM: Zea mays

<400> SEQUENCE: 41

```
Met Arg Glu Arg Asn Ser Ser Ile Asp Gln Glu His Gln Arg Gly Ser
1               5                   10                  15

Ser Ser Arg Ser Thr Met Pro Phe Ala Ala Ser Arg Thr Ser Gln Gln
            20                  25                  30

Gln His Ser Arg Val Ala Thr Asn Gly Arg Ala Val Ala Val Cys Ala
        35                  40                  45

Gly His Ala Gly Val Pro Asp Glu Val Ala Arg His His Glu His Ala
50                  55                  60
```

```
Val Ala Ala Gly Gln Cys Cys Ala Ala Met Val Gln Ser Ile Ala Ala
 65                  70                  75                  80

Pro Val Asp Ala Val Trp Ser Leu Val Arg Arg Phe Asp Gln Pro Gln
                 85                  90                  95

Arg Tyr Lys Arg Phe Ile Arg Ser Cys His Leu Val Asp Gly Asp Gly
            100                 105                 110

Ala Glu Val Gly Ser Val Arg Glu Leu Leu Leu Val Ser Gly Leu Pro
        115                 120                 125

Ala Glu Ser Ser Arg Glu Arg Leu Glu Ile Arg Asp Asp Glu Arg Arg
    130                 135                 140

Val Ile Ser Phe Arg Val Leu Gly Gly Asp His Arg Leu Ala Asn Tyr
145                 150                 155                 160

Arg Ser Val Thr Thr Val His Glu Ala Ala Pro Ser Gln Asp Gly Arg
                165                 170                 175

Pro Leu Thr Met Val Val Glu Ser Tyr Val Val Asp Val Pro Pro Gly
            180                 185                 190

Asn Thr Val Glu Glu Thr Arg Ile Phe Val Asp Thr Ile Val Arg Cys
        195                 200                 205

Asn Leu Gln Ser Leu Glu Gly Thr Val Ile Arg Gln Leu Glu Ile Ala
    210                 215                 220

Ala Met Pro His Asp Asp Asn Gln Asn
225                 230

<210> SEQ ID NO 42
<211> LENGTH: 194
<212> TYPE: PRT
<213> ORGANISM: Physcomitrella patens

<400> SEQUENCE: 42

Met Met Gln Glu Lys Gln Gly Arg Pro Asp Phe Gln Phe Leu Leu Glu
  1               5                  10                  15

Gly Gln Gln Asp Leu Ile Cys Arg Phe His Lys His Glu Leu Leu Pro
             20                  25                  30

His Gln Cys Gly Ser Ile Leu Leu Gln Gln Ile Lys Ala Pro Val Gln
         35                  40                  45

Thr Val Trp Leu Ile Val Arg Arg Phe Asp Glu Pro Gln Val Tyr Lys
     50                  55                  60

Arg Phe Ile Gln Arg Cys Asp Ile Val Glu Gly Asp Gly Val Val Gly
 65                  70                  75                  80

Ser Ile Arg Glu Val Gln Leu Val Ser Ser Ile Pro Ala Thr Ser Ser
                 85                  90                  95

Ile Glu Arg Leu Glu Ile Leu Asp Asp Glu His Ile Ile Ser Phe
            100                 105                 110

Arg Val Leu Gly Gly His Arg Leu Gln Asn Tyr Trp Ser Val Thr
        115                 120                 125

Ser Leu His Arg His Glu Ile Gln Gly Gln Met Gly Thr Leu Val Leu
    130                 135                 140

Glu Ser Tyr Val Val Asp Ile Pro Asp Gly Asn Thr Arg Glu Glu Thr
145                 150                 155                 160

His Thr Phe Val Asp Thr Val Arg Cys Asn Leu Lys Ala Leu Ala
                165                 170                 175

Gln Val Ser Glu Gln Lys His Leu Leu Asn Ser Asn Glu Lys Pro Ala
            180                 185                 190

Ala Pro
```

```
<210> SEQ ID NO 43
<211> LENGTH: 191
<212> TYPE: PRT
<213> ORGANISM: Vitis vinifera

<400> SEQUENCE: 43

Met Lys Val Tyr Ser Pro Ser Gln Ile Leu Ala Glu Arg Gly Pro Arg
1               5                   10                  15

Ala Gln Ala Met Gly Asn Leu Tyr His Thr His His Leu Leu Pro Asn
            20                  25                  30

Gln Cys Ser Ser Leu Val Val Gln Thr Thr Asp Ala Pro Leu Pro Gln
        35                  40                  45

Val Trp Ser Met Val Arg Arg Phe Asp Arg Pro Gln Ser Tyr Lys Arg
    50                  55                  60

Phe Val Arg Gly Cys Thr Leu Arg Arg Gly Lys Gly Val Gly Ser
65                  70                  75                  80

Val Arg Glu Val Asn Ile Val Ser Gly Leu Pro Ala Glu Ile Ser Leu
                85                  90                  95

Glu Arg Leu Asp Lys Leu Asp Asp Leu His Val Met Arg Phe Thr
            100                 105                 110

Val Ile Gly Gly Asp His Arg Leu Ala Asn Tyr His Ser Thr Leu Thr
        115                 120                 125

Leu His Glu Asp Glu Asp Gly Val Arg Lys Thr Val Val Met Glu
    130                 135                 140

Ser Tyr Val Val Asp Val Pro Gly Gly Asn Ser Ala Gly Glu Thr Cys
145                 150                 155                 160

Tyr Phe Ala Asn Thr Ile Ile Gly Phe Asn Leu Lys Ala Leu Ala Ala
                165                 170                 175

Val Thr Glu Thr Met Ala Leu Lys Ala Asn Ile Pro Ser Gly Phe
            180                 185                 190

<210> SEQ ID NO 44
<211> LENGTH: 217
<212> TYPE: PRT
<213> ORGANISM: Physcomitrella patens

<400> SEQUENCE: 44

Met Gln Gln Val Lys Gly Arg Gln Asp Phe Gln Arg Leu Leu Glu Ala
1               5                   10                  15

Gln Gln Asp Leu Ile Cys Arg Tyr His Thr His Glu Leu Lys Ala His
            20                  25                  30

Gln Cys Gly Ser Ile Leu Leu Gln Gln Ile Lys Val Pro Leu Pro Ile
        35                  40                  45

Val Trp Ala Ile Val Arg Ser Phe Asp Lys Pro Gln Val Tyr Lys Arg
    50                  55                  60

Phe Ile Gln Thr Cys Lys Ile Thr Glu Gly Asp Gly Val Gly Ser
65                  70                  75                  80

Ile Arg Glu Val His Leu Val Ser Ser Val Pro Ala Thr Cys Ser Ile
                85                  90                  95

Glu Arg Leu Glu Ile Leu Asp Asp Glu Lys His Ile Ile Ser Phe Arg
            100                 105                 110

Val Leu Gly Gly Gly His Arg Leu Gln Asn Tyr Ser Ser Val Ser Ser
        115                 120                 125

Leu His Glu Leu Glu Val Glu Gly His Pro Cys Thr Leu Val Leu Glu
    130                 135                 140
```

-continued

```
Ser Tyr Met Val Asp Ile Pro Asp Gly Asn Thr Arg Glu Glu Thr His
145                 150                 155                 160

Met Phe Val Asp Thr Val Val Arg Cys Asn Leu Lys Ser Leu Ala Gln
            165                 170                 175

Ile Ser Glu Gln Gln Tyr Asn Lys Asp Cys Leu Gln Gln Lys Gln His
        180                 185                 190

Asp Gln Gln Gln Met Tyr Gln Gln Arg His Pro Pro Leu Pro Pro Ile
    195                 200                 205

Pro Ile Thr Asp Lys Asn Met Glu Arg
    210                 215
```

<210> SEQ ID NO 45
<211> LENGTH: 195
<212> TYPE: PRT
<213> ORGANISM: Physcomitrella patens

<400> SEQUENCE: 45

```
Met Arg Phe Asp Ile Gly His Asn Asp Val Arg Gly Phe Phe Thr Cys
1               5                   10                  15

Glu Glu Glu His Ala Tyr Ala Leu His Ser Gln Thr Val Glu Leu Asn
            20                  25                  30

Gln Cys Gly Ser Ile Leu Met Gln Gln Ile His Ala Pro Ile Glu Val
        35                  40                  45

Val Trp Ser Ile Val Arg Ser Phe Gly Ser Pro Gln Ile Tyr Lys Lys
    50                  55                  60

Phe Ile Gln Ala Cys Ile Leu Thr Val Gly Asp Gly Val Gly Ser
65                  70                  75                  80

Ile Arg Glu Val Phe Leu Val Ser Gly Val Pro Ala Thr Ser Ser Ile
                85                  90                  95

Glu Arg Leu Glu Ile Leu Asp Asp Glu Lys His Val Phe Ser Phe Arg
            100                 105                 110

Val Leu Lys Gly Gly His Arg Leu Gln Asn Tyr Arg Ser Val Thr Thr
        115                 120                 125

Leu His Glu Gln Glu Val Asn Gly Arg Gln Thr Thr Thr Val Leu Glu
    130                 135                 140

Ser Tyr Val Val Asp Val Pro Asp Gly Asn Thr Arg Glu Glu Thr His
145                 150                 155                 160

Met Phe Ala Asp Thr Val Val Met Cys Asn Leu Lys Ser Leu Ala Gln
                165                 170                 175

Val Ala Glu Trp Arg Ala Met Gln Gly Ile Thr Gln Gln Leu Ser Thr
            180                 185                 190

Ser Ser Leu
        195
```

<210> SEQ ID NO 46
<211> LENGTH: 172
<212> TYPE: PRT
<213> ORGANISM: Vitis vinifera

<400> SEQUENCE: 46

```
Met Gly Asn Leu Tyr His Thr His His Leu Leu Pro Asn Gln Cys Ser
1               5                   10                  15

Ser Leu Val Val Gln Thr Thr Asp Ala Pro Leu Pro Gln Val Trp Ser
            20                  25                  30

Met Val Arg Arg Phe Asp Arg Pro Gln Ser Tyr Lys Arg Phe Val Arg
        35                  40                  45
```

Gly Cys Thr Leu Arg Arg Gly Lys Gly Val Gly Ser Val Arg Glu
    50                  55                  60

Val Asn Ile Val Ser Gly Leu Pro Ala Glu Ile Ser Leu Glu Arg Leu
65                  70                  75                  80

Asp Lys Leu Asp Asp Asp Leu His Val Met Arg Phe Thr Val Ile Gly
                85                  90                  95

Gly Asp His Arg Leu Ala Asn Tyr His Ser Thr Leu Thr Leu His Glu
                100                 105                 110

Asp Glu Glu Asp Gly Val Arg Lys Thr Val Val Met Glu Ser Tyr Val
                115                 120                 125

Val Asp Val Pro Gly Gly Asn Ser Ala Gly Glu Thr Cys Tyr Phe Ala
130                 135                 140

Asn Thr Ile Ile Gly Phe Asn Leu Lys Ala Leu Ala Ala Val Thr Glu
145                 150                 155                 160

Thr Met Ala Leu Lys Ala Asn Ile Pro Ser Gly Phe
                165                 170

<210> SEQ ID NO 47
<211> LENGTH: 196
<212> TYPE: PRT
<213> ORGANISM: Picea sitchensis

<400> SEQUENCE: 47

Met Glu Asp Leu Ser Ser Trp Arg Glu Gly Arg Ala Met Trp Leu Gly
1               5                   10                  15

Asn Pro Pro Ser Glu Ser Glu Leu Val Cys Arg His His Arg His Glu
                20                  25                  30

Leu Gln Gly Asn Gln Cys Ser Ser Phe Leu Val Lys His Ile Arg Ala
            35                  40                  45

Pro Val His Leu Val Trp Ser Ile Val Arg Thr Phe Asp Gln Pro Gln
        50                  55                  60

Lys Tyr Lys Pro Phe Val His Ser Cys Ser Val Arg Gly Gly Ile Thr
65                  70                  75                  80

Val Gly Ser Ile Arg Asn Val Asn Val Lys Ser Gly Leu Pro Ala Thr
                85                  90                  95

Ala Ser Glu Glu Arg Leu Glu Ile Leu Asp Asp Asn Glu His Val Phe
                100                 105                 110

Ser Ile Lys Ile Leu Gly Gly Asp His Arg Leu Gln Asn Tyr Ser Ser
                115                 120                 125

Ile Ile Thr Val His Pro Glu Ile Ile Asp Gly Arg Pro Gly Thr Leu
130                 135                 140

Val Ile Glu Ser Tyr Val Val Asp Val Pro Glu Gly Asn Thr Arg Glu
145                 150                 155                 160

Glu Thr Arg Phe Phe Val Glu Ala Leu Val Lys Cys Asn Leu Lys Ser
                165                 170                 175

Leu Ala Asp Val Ser Glu Arg Leu Ala Ser Gln His His Thr Glu Leu
                180                 185                 190

Leu Glu Arg Thr
            195

<210> SEQ ID NO 48
<211> LENGTH: 185
<212> TYPE: PRT
<213> ORGANISM: Solanum tuberosum

<400> SEQUENCE: 48

```
Met Asn Ala Asn Gly Phe Cys Gly Val Glu Lys Glu Tyr Ile Arg Lys
1               5                   10                  15

His His Leu His Glu Pro Lys Glu Asn Gln Cys Ser Ser Phe Leu Val
            20                  25                  30

Lys His Ile Arg Ala Pro Val His Leu Val Trp Ser Leu Val Arg Arg
        35                  40                  45

Phe Asp Gln Pro Gln Lys Tyr Lys Pro Phe Ile Ser Arg Cys Ile Val
    50                  55                  60

Gln Gly Asp Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Glu Glu His Ile Leu Ser Val Arg Ile Val Gly Gly Asp His Arg Leu
                100                 105                 110

Arg Asn Tyr Ser Ser Val Ile Ser Val His Pro Glu Val Ile Asp Gly
            115                 120                 125

Arg Pro Gly Thr Val Val Leu Glu Ser Phe Val Val Asp Val Pro Glu
        130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Ile Ser Glu Arg Val Ala Val Gln
                165                 170                 175

Asp Arg Thr Glu Pro Ile Asp Gln Val
            180                 185

<210> SEQ ID NO 49
<211> LENGTH: 190
<212> TYPE: PRT
<213> ORGANISM: Medicago truncatula

<400> SEQUENCE: 49

Met Asn Asn Gly Cys Glu Gln Gln Tyr Ser Val Ile Glu Thr Gln
1               5                   10                  15

Tyr Ile Arg Arg His His Lys His Asp Leu Arg Asp Asn Gln Cys Ser
            20                  25                  30

Ser Ala Leu Val Lys His Ile Lys Ala Pro Val His Leu Val Trp Ser
        35                  40                  45

Leu Val Arg Arg Phe Asp Gln Pro Gln Lys Tyr Lys Pro Phe Ile Ser
    50                  55                  60

Arg Cys Ile Met Gln Gly Asp Leu Ser Ile Gly Ser Val Arg Glu Val
65                  70                  75                  80

Asn Val Lys Ser Gly Leu Pro Ala Thr Thr Ser Thr Glu Arg Leu Glu
                85                  90                  95

Gln Leu Asp Asp Glu Glu His Ile Leu Gly Ile Arg Ile Val Gly Gly
                100                 105                 110

Asp His Arg Leu Arg Asn Tyr Ser Ser Ile Ile Thr Val His Pro Gly
            115                 120                 125

Val Ile Asp Gly Arg Pro Gly Thr Met Val Ile Glu Ser Phe Val Val
        130                 135                 140

Asp Val Pro Glu Gly Asn Thr Lys Asp Glu Thr Cys Tyr Phe Val Glu
145                 150                 155                 160

Ala Leu Ile Arg Tyr Asn Leu Ser Ser Leu Ala Asp Val Ser Glu Arg
                165                 170                 175

Met Ala Val Gln Gly Arg Thr Asp Pro Ile Asn Ile Asn Pro
            180                 185                 190
```

<210> SEQ ID NO 50
<211> LENGTH: 185
<212> TYPE: PRT
<213> ORGANISM: Vitis vinifera

<400> SEQUENCE: 50

Met Ser Gly Tyr Gly Cys Ile Lys Met Glu Asp Glu Tyr Ile Arg Arg
1               5                   10                  15

His His Arg His Glu Ile Arg Asp Asn Gln Cys Ser Ser Ser Leu Val
            20                  25                  30

Lys His Ile Lys Ala Pro Val His Leu Val Trp Ser Leu Val Arg Ser
        35                  40                  45

Phe Asp Gln Pro Gln Lys Tyr Lys Pro Phe Val Ser Arg Cys Ile Val
    50                  55                  60

Gln Gly Asp Leu Glu Ile Gly Ser Val Arg Glu Val Asn Val Lys Ser
65                  70                  75                  80

Gly Leu Pro Ala Thr Thr Ser Thr Glu Arg Leu Glu Leu Leu Asp Asp
                85                  90                  95

Glu Glu His Ile Phe Gly Met Arg Ile Val Gly Gly Asp His Arg Leu
            100                 105                 110

Lys Asn Tyr Ser Ser Ile Val Thr Val His Pro Glu Ile Ile Asp Gly
        115                 120                 125

Arg Pro Gly Thr Leu Val Ile Glu Ser Phe Val Val Asp Val Pro Asp
    130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Ile Gln
                165                 170                 175

Asp Arg Thr Glu Pro Ile Asp Arg Met
            180                 185

<210> SEQ ID NO 51
<211> LENGTH: 185
<212> TYPE: PRT
<213> ORGANISM: Vitis vinifera

<400> SEQUENCE: 51

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
    50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

```
Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Arg Met
            180                 185
```

<210> SEQ ID NO 52
<211> LENGTH: 208
<212> TYPE: PRT
<213> ORGANISM: Oryza sativa

<400> SEQUENCE: 52

```
Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
            20                  25                  30

Pro Ser Thr Thr Thr Ala Thr Thr Ala Ala Thr Cys Thr Ser Leu
        35                  40                  45

Val Thr Gln Arg Val Ala Ala Pro Val Arg Ala Val Trp Pro Ile Val
50                  55                  60

Arg Ser Phe Gly Asn Pro Gln Arg Tyr Lys His Phe Val Arg Thr Cys
65                  70                  75                  80

Ala Leu Ala Ala Gly Asn Gly Pro Ser Phe Gly Ser Val Arg Glu Val
                85                  90                  95

Thr Val Val Ser Gly Pro Ser Arg Leu Pro Pro Gly Thr Glu Arg Leu
            100                 105                 110

Glu Met Leu Asp Asp Asp Arg His Ile Ile Ser Phe Arg Val Val Gly
            115                 120                 125

Gly Gln His Arg Leu Arg Asn Tyr Arg Ser Val Thr Ser Val Thr Glu
130                 135                 140

Phe Gln Pro Pro Ala Ala Gly Pro Gly Pro Ala Pro Pro Tyr Cys Val
145                 150                 155                 160

Val Val Glu Ser Tyr Val Val Asp Val Pro Asp Gly Asn Thr Ala Glu
                165                 170                 175

Asp Thr Arg Met Phe Thr Asp Thr Val Lys Leu Asn Leu Gln Met
            180                 185                 190

Leu Ala Ala Val Ala Glu Asp Ser Ser Ser Ala Ser Arg Arg Arg Asp
            195                 200                 205
```

<210> SEQ ID NO 53
<211> LENGTH: 186
<212> TYPE: PRT
<213> ORGANISM: Capsicum annuum

<400> SEQUENCE: 53

```
Met Met Asn Ala Asn Gly Phe Ser Gly Val Glu Lys Glu Tyr Ile Arg
1               5                   10                  15

Lys His His Leu His Gln Pro Lys Glu Asn Gln Cys Ser Ser Phe Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
50                  55                  60

Ala Gln Gly Asp Leu Glu Ile Gly Ser Leu Arg Glu Val Asp Val Lys
65                  70                  75                  80
```

```
Ser Gly Leu Pro Ala Thr Thr Ser Thr Glu Arg Leu Glu Leu Leu Asp
                85                  90                  95

Asp Glu Glu His Ile Leu Ser Phe Arg Ile Ile Gly Gly Asp His Arg
            100                 105                 110

Leu Arg Asn Tyr Ser Ser Ile Ile Ser Leu His Pro Glu Val Ile Asp
        115                 120                 125

Gly Arg Pro Gly Thr Leu Val Ile Glu Ser Phe Val Val Asp Val Pro
    130                 135                 140

Gln Gly Asn Thr Lys Asp Glu Thr Cys Tyr Phe Val Glu Ala Leu Ile
145                 150                 155                 160

Asn Cys Asn Leu Lys Ser Leu Ala Asp Val Ser Glu Arg Leu Ala Val
                165                 170                 175

Gln Asp Arg Thr Glu Pro Ile Asp Gln Val
            180                 185

<210> SEQ ID NO 54
<211> LENGTH: 186
<212> TYPE: PRT
<213> ORGANISM: Populus trichocarpa

<400> SEQUENCE: 54

Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
            20                  25                  30

Val Lys His Ile Lys Ala Pro Ala His Leu Val Trp Ser Leu Val Arg
        35                  40                  45

Arg Phe Asp Gln Pro Gln Arg Tyr Lys Pro Phe Val Ser Arg Cys Val
    50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Glu Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

<210> SEQ ID NO 55
<211> LENGTH: 185
<212> TYPE: PRT
<213> ORGANISM: Capsicum annuum

<400> SEQUENCE: 55

Met Asn Ala Asn Gly Phe Ser Gly Val Glu Lys Glu Tyr Ile Arg Lys
1               5                   10                  15

His His Leu His Gln Pro Lys Glu Asn Gln Cys Ser Ser Phe Leu Val
            20                  25                  30
```

```
Lys His Ile Arg Ala Pro Val His Leu Val Trp Ser Leu Val Arg Arg
            35                  40                  45

Phe Asp Gln Pro Gln Lys Tyr Lys Pro Phe Val Ser Arg Cys Ile Ala
 50                  55                  60

Gln Gly Asp Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                85                  90                  95

Glu Glu His Ile Leu Ser Phe Arg Ile Ile Gly Gly Asp His Arg Leu
                100                 105                 110

Arg Asn Tyr Ser Ser Ile Ile Ser Leu His Pro Glu Val Ile Asp Gly
            115                 120                 125

Arg Pro Gly Thr Leu Val Ile Glu Ser Phe Val Asp Val Pro Gln
130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Gln Val
                180                 185

<210> SEQ ID NO 56
<211> LENGTH: 186
<212> TYPE: PRT
<213> ORGANISM: Populus trichocarpa x Populus deltoides

<400> SEQUENCE: 56

Met Asn Gly Ser Asp Ala Tyr Ser Ala Thr Glu Ala Gln Tyr Val Arg
 1               5                  10                  15

Arg His His Lys His Glu Pro Arg Glu Asn Gln Cys Thr Ser Ala Leu
                20                  25                  30

Val Lys His Ile Lys Ala Pro Ala His Leu Val Trp Ser Leu Val Arg
            35                  40                  45

Arg Phe Asp Gln Pro Gln Arg Tyr Lys Pro Phe Val Ser Arg Cys Val
 50                  55                  60

Met Asn Gly Glu Leu Gly Ile Gly Ser Val Arg Glu Val Asn Val Lys
 65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
                100                 105                 110

Leu Lys Asn Tyr Ser Ser Ile Met Thr Val His Pro Glu Phe Ile Asp
            115                 120                 125

Gly Arg Pro Gly Thr Leu Val Ile Glu Ser Phe Ile Val Asp Val Pro
130                 135                 140

Asp Gly Asn Thr Lys Asp Glu Thr Cys Tyr Phe Val Lys Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
                180                 185

<210> SEQ ID NO 57
<211> LENGTH: 188
<212> TYPE: PRT
```

<213> ORGANISM: Pisum sativum

<400> SEQUENCE: 57

Met Asn Asn Gly Gly Glu Gln Tyr Ser Ala Ile Glu Thr Gln Tyr Ile
1               5                   10                  15

Arg Arg Arg His Lys His Asp Leu Arg Asp Asn Gln Cys Ser Ser Ala
            20                  25                  30

Leu Val Lys His Ile Lys Ala Pro Val His Leu Val Trp Ser Leu Val
        35                  40                  45

Arg Arg Phe Asp Gln Pro Gln Lys Tyr Lys Pro Phe Val Ser Arg Cys
    50                  55                  60

Ile Met Gln Gly Asp Leu Gly Ile Gly Ser Val Arg Glu Val Asn Val
65                  70                  75                  80

Lys Ser Gly Leu Pro Ala Thr Thr Ser Thr Glu Arg Leu Glu Gln Leu
                85                  90                  95

Asp Asp Glu Glu His Ile Leu Gly Ile Arg Ile Val Gly Gly Asp His
            100                 105                 110

Arg Leu Arg Asn Tyr Ser Ser Val Ile Thr Val His Pro Glu Val Ile
        115                 120                 125

Asp Gly Arg Pro Gly Thr Met Val Ile Glu Ser Phe Val Val Asp Val
    130                 135                 140

Pro Glu Gly Asn Thr Arg Asp Glu Thr Cys Tyr Phe Val Glu Ala Leu
145                 150                 155                 160

Ile Arg Gly Asn Leu Ser Ser Leu Ala Asp Val Ser Glu Arg Met Ala
                165                 170                 175

Val Gln Gly Arg Thr Asp Pro Ile Asn Val Asn Pro
            180                 185

<210> SEQ ID NO 58
<211> LENGTH: 177
<212> TYPE: PRT
<213> ORGANISM: Vitis vinifera

<400> SEQUENCE: 58

Met Glu Ala Gln Val Ile Cys Arg His His Ala His Glu Pro Arg Glu
1               5                   10                  15

Asn Gln Cys Ser Ser Val Leu Val Arg His Val Lys Ala Pro Ala Asn
            20                  25                  30

Leu Val Trp Ser Leu Val Arg Arg Phe Asp Gln Pro Gln Lys Tyr Lys
        35                  40                  45

Pro Phe Val Ser Arg Cys Val Val Gln Gly Asp Leu Arg Ile Gly Ser
    50                  55                  60

Val Arg Glu Val Asn Val Lys Thr Gly Leu Pro Ala Thr Thr Ser Thr
65                  70                  75                  80

Glu Arg Leu Glu Leu Phe Asp Asp Asp Glu His Val Leu Gly Ile Lys
                85                  90                  95

Ile Leu Asp Gly Asp His Arg Leu Arg Asn Tyr Ser Ser Val Ile Thr
            100                 105                 110

Val His Pro Glu Ile Ile Asp Gly Arg Pro Gly Thr Leu Val Ile Glu
        115                 120                 125

Ser Phe Val Val Asp Val Pro Glu Gly Asn Thr Lys Asp Asp Thr Cys
    130                 135                 140

Tyr Phe Val Arg Ala Leu Ile Asn Cys Asn Leu Lys Cys Leu Ala Glu
145                 150                 155                 160

Val Ser Glu Arg Met Ala Met Leu Gly Arg Val Glu Pro Ala Asn Ala

```
                    165                 170                 175

Val

<210> SEQ ID NO 59
<211> LENGTH: 178
<212> TYPE: PRT
<213> ORGANISM: Vitis vinifera

<400> SEQUENCE: 59

Met Met Glu Ala Gln Val Ile Cys Arg His His Ala His Glu Pro Arg
1               5                   10                  15

Glu Asn Gln Cys Ser Ser Val Leu Val Arg His Val Lys Ala Pro Ala
            20                  25                  30

Asn Leu Val Trp Ser Leu Val Arg Arg Phe Asp Gln Pro Gln Lys Tyr
        35                  40                  45

Lys Pro Phe Val Ser Arg Cys Val Val Gln Gly Asp Leu Arg Ile Gly
    50                  55                  60

Ser Val Arg Glu Val Asn Val Lys Thr Gly Leu Pro Ala Thr Thr Ser
65                  70                  75                  80

Thr Glu Arg Leu Glu Leu Phe Asp Asp Glu His Val Leu Gly Ile
                85                  90                  95

Lys Ile Leu Asp Gly Asp His Arg Leu Arg Asn Tyr Ser Ser Val Ile
            100                 105                 110

Thr Val His Pro Glu Ile Ile Asp Gly Arg Pro Gly Thr Leu Val Ile
        115                 120                 125

Glu Ser Phe Val Val Asp Val Pro Glu Gly Asn Thr Lys Asp Asp Thr
    130                 135                 140

Cys Tyr Phe Val Arg Ala Leu Ile Asn Cys Asn Leu Lys Cys Leu Ala
145                 150                 155                 160

Glu Val Ser Glu Arg Met Ala Met Leu Gly Arg Val Glu Pro Ala Asn
                165                 170                 175

Ala Val

<210> SEQ ID NO 60
<211> LENGTH: 193
<212> TYPE: PRT
<213> ORGANISM: Arachis hypogaea
<220> FEATURE:
<221> NAME/KEY: VARIANT
<222> LOCATION: (162)..(162)
<223> OTHER INFORMATION: Xaa = any amino acid

<400> SEQUENCE: 60

Met Met Asn Gly Ser Cys Gly Gly Gly Gly Gly Glu Ala Tyr Gly
1               5                   10                  15

Ala Ile Glu Ala Gln Tyr Ile Arg Arg His His Arg His Glu Pro Arg
            20                  25                  30

Asp Asn Gln Cys Thr Ser Ala Leu Val Lys His Ile Arg Ala Pro Val
        35                  40                  45

His Leu Val Trp Ser Leu Val Arg Arg Phe Asp Gln Pro Gln Lys Tyr
    50                  55                  60

Lys Pro Phe Val Ser Arg Cys Ile Met Gln Gly Asp Leu Gly Ile Gly
65                  70                  75                  80

Ser Val Arg Glu Val Asn Val Lys Ser Gly Leu Pro Ala Thr Thr Ser
                85                  90                  95

Thr Glu Arg Leu Glu Gln Leu Asp Asp Glu Glu His Ile Leu Gly Ile
            100                 105                 110
```

```
Arg Ile Val Gly Gly Asp His Arg Leu Arg Asn Tyr Ser Ser Ile Ile
        115                 120                 125

Thr Val His Pro Glu Val Ile Glu Gly Arg Pro Gly Thr Met Val Ile
    130                 135                 140

Glu Ser Phe Val Val Asp Val Pro Asp Gly Asn Thr Lys Asp Glu Thr
145                 150                 155                 160

Cys Xaa Phe Val Glu Ala Leu Ile Arg Cys Asn Leu Ser Ser Leu Ala
                165                 170                 175

Asp Val Ser Glu Arg Met Ala Val Gln Gly Arg Thr Asp Pro Ile Asn
            180                 185                 190

Gln

<210> SEQ ID NO 61
<211> LENGTH: 217
<212> TYPE: PRT
<213> ORGANISM: Zea mays

<400> SEQUENCE: 61

Met Val Val Glu Met Asp Gly Gly Val Gly Val Ala Ala Gly Gly Gly
1               5                   10                  15

Gly Gly Ala Gln Thr Pro Ala Pro Ala Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
        195                 200                 205

Met Asp Gln Thr Glu Pro Leu Asp Arg
    210                 215

<210> SEQ ID NO 62
<211> LENGTH: 217
<212> TYPE: PRT
<213> ORGANISM: Zea mays

<400> SEQUENCE: 62

Met Val Val Glu Met Asp Gly Gly Val Gly Val Ala Ala Gly Gly
1               5                   10                  15
```

```
Gly Gly Ala Gln Thr Pro Ala Pro Pro Pro Arg Arg Trp Arg Leu
             20                  25                  30

Ala Asp Glu Arg Cys Asp Leu Arg Ala Met Glu Thr Asp Tyr Val Arg
             35                  40                  45

Arg Phe His Arg His Glu Pro Arg Asp His Gln Cys Ser Ser Ala Val
 50                  55                  60

Ala Lys His Ile Lys Ala Pro Val His Leu Val Trp Ser Leu Val Arg
 65              70                  75                  80

Arg Phe Asp Gln Pro Gln Leu Phe Lys Pro Phe Val Ser Arg Cys Glu
             85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
            115                 120                 125

Asp Asp Glu Arg Ile Leu Ser Val Arg Phe Val Gly Asp His Arg
            130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
                180                 185                 190

Lys Cys Asn Leu Arg Ser Leu Ala Glu Val Ser Glu Gly Gln Val Ile
                195                 200                 205

Met Asp Gln Thr Glu Pro Leu Asp Arg
            210                 215

<210> SEQ ID NO 63
<211> LENGTH: 206
<212> TYPE: PRT
<213> ORGANISM: Oryza sativa

<400> SEQUENCE: 63

Met Asn Gly Val Gly Gly Ala Gly Ala Ala Gly Lys Leu Pro
1               5                   10                  15

Met Val Ser His Arg Arg Val Gln Trp Arg Leu Ala Asp Glu Arg Cys
             20                  25                  30

Glu Leu Arg Glu Glu Met Glu Tyr Ile Arg Arg Phe His Arg His
             35                  40                  45

Glu Pro Ser Ser Asn Gln Cys Thr Ser Phe Ala Ala Lys His Ile Lys
 50                  55                  60

Ala Pro Leu His Thr Val Trp Ser Leu Val Arg Arg Phe Asp Gln Pro
 65              70                  75                  80

Gln Leu Phe Lys Pro Phe Val Arg Asn Cys Val Met Arg Glu Asn Ile
             85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
            115                 120                 125

Ile Leu Lys Val Asn Phe Ile Gly Gly Asp His Met Leu Lys Asn Tyr
            130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Pro Glu Gly Asn Thr
                165                 170                 175
```

```
Lys Asp Asp Ile Ser Tyr Phe Ile Glu Asn Val Leu Arg Cys Asn Leu
            180                 185                 190
Arg Thr Leu Ala Asp Val Ser Glu Glu Arg Leu Ala Asn Pro
        195                 200                 205

<210> SEQ ID NO 64
<211> LENGTH: 206
<212> TYPE: PRT
<213> ORGANISM: Oryza sativa

<400> SEQUENCE: 64

Met Asn Gly Ala Gly Gly Ala Gly Ala Ala Gly Lys Leu Pro
1               5                   10                  15
Met Val Ser His Arg Gln Val Gln Trp Arg Leu Ala Asp Glu Arg Cys
            20                  25                  30
Glu Leu Arg Glu Glu Met Glu Tyr Ile Arg Gln Phe His Arg His
        35                  40                  45
Glu Pro Ser Ser Asn Gln Cys Thr Ser Phe Val Ala Lys His Ile Lys
    50                  55                  60
Ala Pro Leu Gln Thr Val Trp Ser Leu Val Arg Arg Phe Asp Gln Pro
65                  70                  75                  80
Gln Leu Phe Lys Pro Phe Val Arg Lys Cys Val Met Arg Glu Asn Ile
                85                  90                  95
Ile Ala Thr Gly Cys Val Arg Glu Val Asn Val Gln Ser Gly Leu Pro
            100                 105                 110
Ala Thr Arg Ser Thr Glu Arg Leu Glu Leu Leu Asp Asp Asn Glu His
        115                 120                 125
Ile Leu Lys Val Lys Phe Ile Gly Gly Asp His Met Leu Lys Asn Tyr
    130                 135                 140
Ser Ser Ile Leu Thr Ile His Ser Glu Val Ile Asp Gly Gln Leu Gly
145                 150                 155                 160
Thr Leu Val Val Glu Ser Phe Val Val Asp Ile Pro Glu Gly Asn Thr
                165                 170                 175
Lys Asp Asp Ile Cys Tyr Phe Ile Glu Asn Ile Leu Arg Cys Asn Leu
            180                 185                 190
Met Thr Leu Ala Asp Val Ser Glu Glu Arg Leu Ala Asn Pro
        195                 200                 205

<210> SEQ ID NO 65
<211> LENGTH: 205
<212> TYPE: PRT
<213> ORGANISM: Oryza sativa

<400> SEQUENCE: 65

Met Val Glu Val Gly Gly Gly Ala Ala Glu Ala Ala Gly Arg Arg
1               5                   10                  15
Trp Arg Leu Ala Asp Glu Arg Cys Asp Leu Arg Ala Ala Glu Thr Glu
            20                  25                  30
Tyr Val Arg Arg Phe His Arg His Glu Pro Arg Asp His Gln Cys Ser
        35                  40                  45
Ser Ala Val Ala Lys His Ile Lys Ala Pro Val His Leu Val Trp Ser
    50                  55                  60
Leu Val Arg Arg Phe Asp Gln Pro Gln Leu Phe Lys Pro Phe Val Ser
65                  70                  75                  80
Arg Cys Glu Met Lys Gly Asn Ile Glu Ile Gly Ser Val Arg Glu Val
                85                  90                  95
```

```
Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
        115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Cys Gln Gly Pro Asn Arg Ala Pro Ser Thr Arg
        195                 200                 205

<210> SEQ ID NO 66
<211> LENGTH: 204
<212> TYPE: PRT
<213> ORGANISM: Oryza sativa

<400> SEQUENCE: 66

Met Val Glu Val Gly Gly Gly Ala Ala Glu Ala Ala Gly Arg Arg
1               5                   10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
        115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Val Lys Asp Gln Thr Glu Pro Leu Asp Arg
        195                 200

<210> SEQ ID NO 67
<211> LENGTH: 199
<212> TYPE: PRT
<213> ORGANISM: Medicago truncatula

<400> SEQUENCE: 67

Met Glu Lys Met Asn Gly Thr Glu Asn Asn Gly Val Phe Asn Ser Thr
1               5                   10                  15
```

Glu Met Glu Tyr Ile Arg Arg His His Asn Gln Gln Pro Gly Glu Asn
            20                  25                  30

Gln Cys Ser Ser Ala Leu Val Lys His Ile Arg Ala Pro Val Pro Leu
        35                  40                  45

Val Trp Ser Leu Val Arg Arg Phe Asp Gln Pro Gln Lys Tyr Lys Pro
 50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
        115                 120                 125

His Pro Glu Ile Ile Asp Gly Arg Pro Gly Thr Leu Val Ile Glu Ser
130                 135                 140

Phe Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Val Gln Asp Leu Thr Glu Pro Leu Asp Arg Val
            180                 185                 190

His Glu Leu Leu Ile Ser Gly
        195

<210> SEQ ID NO 68
<211> LENGTH: 199
<212> TYPE: PRT
<213> ORGANISM: Medicago truncatula

<400> SEQUENCE: 68

Met Glu Lys Met Asn Gly Thr Glu Asn Asn Gly Val Phe Asn Ser Thr
1               5                   10                  15

Glu Met Glu Tyr Ile Arg Arg His His Asn Gln Gln Pro Gly Glu Asn
            20                  25                  30

Gln Cys Ser Ser Ala Leu Val Lys His Ile Arg Ala Pro Val Pro Leu
        35                  40                  45

Val Trp Ser Leu Val Arg Arg Phe Asp Gln Pro Gln Lys Tyr Lys Pro
 50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
        115                 120                 125

His Pro Glu Ile Ile Asp Gly Arg Pro Gly Thr Leu Val Ile Glu Ser
130                 135                 140

Phe Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Ala Gln Asp Leu Thr Glu Pro Leu Asp Arg Met

His Glu Leu Leu Ile Ser Gly
        195

<210> SEQ ID NO 69
<211> LENGTH: 197
<212> TYPE: PRT
<213> ORGANISM: Zea mays

<400> SEQUENCE: 69

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Gln Leu Val Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 70
<211> LENGTH: 197
<212> TYPE: PRT
<213> ORGANISM: Zea mays

<400> SEQUENCE: 70

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Glu Leu Val Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His

```
            100                 105                 110
Ile Leu Gly Val Lys Phe Val Gly Gly Asp His Arg Leu Gln Asn Tyr
            115                 120                 125

Ser Ser Ile Ile Thr Val His Pro Glu Ser Ile Asp Gly Arg Pro Gly
            130                 135             140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
                180                 185                 190

Ser Leu Ile Asp Gln
        195

<210> SEQ ID NO 71
<211> LENGTH: 212
<212> TYPE: PRT
<213> ORGANISM: Zea mays

<400> SEQUENCE: 71

Met Val Met Val Glu Met Asp Gly Gly Val Gly Gly Gly Gly Gly Gly
1               5                   10                  15

Gly Gln Thr Pro Ala Pro Arg Arg Trp Arg Leu Ala Asp Glu Arg Cys
            20                  25                  30

Asp Leu Arg Ala Met Glu Thr Asp Tyr Val Arg Arg Phe His Arg His
            35                  40                  45

Glu Pro Arg Glu His Gln Cys Ser Ser Ala Val Ala Lys His Ile Lys
    50                  55                  60

Ala Pro Val His Leu Val Trp Ser Leu Val Arg Arg Phe Asp Gln Pro
65                  70                  75                  80

Gln Leu Phe Lys Pro Phe Val Ser Arg Cys Glu Met Lys Gly Asn Ile
                85                  90                  95

Glu Ile Gly Ser Val Arg Glu Val Asn Val Lys Ser Gly Leu Pro Ala
            100                 105                 110

Thr Arg Ser Thr Glu Arg Leu Glu Leu Leu Asp Asp Asn Glu His Ile
            115                 120                 125

Leu Ser Val Arg Phe Val Gly Gly Asp His Arg Leu Gln Asn Tyr Ser
        130                 135                 140

Ser Ile Leu Thr Val His Pro Glu Val Ile Asp Gly Arg Pro Gly Thr
145                 150                 155                 160

Leu Val Ile Glu Ser Phe Val Val Asp Val Pro Asp Gly Asn Thr Lys
                165                 170                 175

Asp Glu Thr Cys Tyr Phe Val Glu Ala Leu Leu Lys Cys Asn Leu Lys
            180                 185                 190

Ser Leu Ala Glu Val Ser Glu Arg Gln Val Val Lys Asp Gln Thr Glu
        195                 200                 205

Pro Leu Asp Arg
    210

<210> SEQ ID NO 72
<211> LENGTH: 205
<212> TYPE: PRT
<213> ORGANISM: Oryza sativa

<400> SEQUENCE: 72

Met Asn Gly Ala Gly Gly Ala Gly Gly Ala Ala Ala Gly Lys Leu Pro
```

```
1               5                   10                  15
Met Val Ser His Arg Val Gln Cys Arg Leu Ala Asp Lys Arg Cys
            20                  25                  30

Glu Leu Arg Glu Glu Met Glu Tyr Ile Arg Gln Phe His Arg His
            35                  40                  45

Glu Pro Ser Ser Asn Gln Cys Thr Ser Phe Val Ala Lys His Ile Lys
 50                      55                  60

Ala Pro Leu Gln Thr Val Trp Ser Leu Val Arg Arg Phe Asp Gln Pro
 65                  70                  75                  80

Gln Leu Phe Lys Pro Phe Val Arg Lys Cys Val Met Arg Glu Asn Ile
                85                  90                  95

Ile Val Thr Gly Cys Val Arg Glu Val Asn Val Gln Ser Gly Leu Pro
                100                 105                 110

Ala Thr Arg Ser Thr Glu Arg Leu Glu Leu Leu Asp Asp Asn Glu His
            115                 120                 125

Ile Leu Lys Val Lys Phe Ile Gly Gly Asp His Met Leu Lys Asn Tyr
 130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Asp Gly Asn Thr
                165                 170                 175

Lys Asp Asp Ile Cys Tyr Phe Ile Glu Asn Val Leu Arg Cys Asn Leu
            180                 185                 190

Met Thr Leu Ala Asp Val Ser Glu Glu Arg Leu Ala Asn
            195                 200                 205

<210> SEQ ID NO 73
<211> LENGTH: 197
<212> TYPE: PRT
<213> ORGANISM: Zea mays

<400> SEQUENCE: 73

Met Val Gly Leu Val Gly Gly Ser Thr Ala Arg Ala Glu His Val Val
 1               5                   10                  15

Ala Asn Ala Gly Gly Glu Thr Glu Tyr Val Arg Arg Leu His Arg His
            20                  25                  30

Ala Pro Ala Glu His Gln Cys Thr Ser Thr Leu Val Lys His Ile Lys
            35                  40                  45

Ala Pro Val His Leu Val Trp Glu Leu Val Arg Ser Phe Asp Gln Pro
 50                  55                  60

Gln Arg Tyr Lys Pro Phe Val Arg Asn Cys Val Val Arg Gly Asp Gln
 65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
                100                 105                 110

Ile Leu Gly Val Lys Phe Val Gly Gly Asp His Arg Leu Gln Asn Tyr
            115                 120                 125

Ser Ser Ile Ile Thr Val His Pro Glu Ser Ile Asp Gly Arg Pro Gly
 130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
            165                 170                 175
```

```
Lys Ser Leu Ala Glu Val Ser Glu Gln Leu Ala Val Glu Ser Pro Thr
            180                 185                 190

Ser Pro Ile Asp Gln
        195
```

<210> SEQ ID NO 74
<211> LENGTH: 206
<212> TYPE: PRT
<213> ORGANISM: Oryza sativa

<400> SEQUENCE: 74

```
Met Asn Gly Val Gly Gly Ala Gly Gly Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Met Glu Tyr Ile Arg Arg Phe His Arg His
        35                  40                  45

Glu Pro Ser Ser Asn Gln Cys Thr Ser Phe Ala Ala Lys His Ile Lys
50                  55                  60

Ala Pro Leu His Thr Val Trp Ser Leu Val Arg Arg Phe Asp Gln Pro
65                  70                  75                  80

Gln Leu Phe Lys Pro Phe Val Arg Asn Cys Val Met Arg Glu Asn Ile
                85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Leu Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205
```

<210> SEQ ID NO 75
<211> LENGTH: 209
<212> TYPE: PRT
<213> ORGANISM: Oryza sativa

<400> SEQUENCE: 75

```
Met Val Gly Leu Val Gly Gly Gly Trp Arg Val Gly Asp Asp Ala
1               5                   10                  15

Ala Gly Gly Gly Gly Gly Ala Val Ala Ala Gly Ala Ala Ala Ala
            20                  25                  30

Ala Glu Ala Glu His Met Arg Arg Leu His Ser His Ala Pro Gly Glu
        35                  40                  45

His Gln Cys Ser Ser Ala Leu Val Lys His Ile Lys Ala Pro Val His
50                  55                  60

Leu Val Trp Ser Leu Val Arg Ser Phe Asp Gln Pro Gln Arg Tyr Lys
65                  70                  75                  80

Pro Phe Val Ser Arg Cys Val Val Arg Gly Gly Asp Leu Glu Ile Gly
                85                  90                  95
```

Ser Val Arg Glu Val Asn Val Lys Thr Gly Leu Pro Ala Thr Thr Ser
            100                 105                 110

Thr Glu Arg Leu Glu Leu Leu Asp Asp Glu His Ile Leu Ser Val
        115                 120                 125

Lys Phe Val Gly Gly Asp His Arg Leu Arg Asn Tyr Ser Ser Ile Val
130                 135                 140

Thr Val His Pro Glu Ser Ile Asp Gly Arg Pro Gly Thr Leu Val Ile
145                 150                 155                 160

Glu Ser Phe Val Val Asp Val Pro Asp Gly Asn Thr Lys Asp Glu Thr
                165                 170                 175

Cys Tyr Phe Val Glu Ala Val Ile Lys Cys Asn Leu Thr Ser Leu Ala
            180                 185                 190

Glu Val Ser Glu Arg Leu Ala Val Gln Ser Pro Thr Ser Pro Leu Glu
        195                 200                 205

Gln

<210> SEQ ID NO 76
<211> LENGTH: 180
<212> TYPE: PRT
<213> ORGANISM: Oryza sativa

<400> SEQUENCE: 76

Met Val Glu Met Asp Ala Gly Gly Arg Pro Glu Pro Ser Pro Pro Ser
1               5                   10                  15

Gly Gln Cys Ser Ser Ala Val Thr Met Arg Ile Asn Ala Pro Val His
            20                  25                  30

Leu Val Trp Ser Ile Val Arg Arg Phe Glu Glu Pro Ile Phe Gln
        35                  40                  45

Pro Phe Val Arg Gly Cys Thr Met Arg Gly Ser Thr Ser Leu Ala Val
    50                  55                  60

Gly Cys Val Arg Glu Val Asp Phe Lys Ser Gly Phe Pro Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
        115                 120                 125

Ser Glu Ser Phe Val Val Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Ala Gln Gly Asp Leu Ala Glu
                165                 170                 175

Pro Pro Ala Gln
        180

<210> SEQ ID NO 77
<211> LENGTH: 176
<212> TYPE: PRT
<213> ORGANISM: Vitis vinifera

<400> SEQUENCE: 77

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val

```
                 20                  25                  30
Lys His Ile Lys Ala Pro Val Pro Leu Val Trp Ser Leu Val Arg Arg
             35                  40                  45

Phe Asp Gln Pro Gln Lys Tyr Lys Pro Phe Ile Ser Arg Cys Val Val
         50                  55                  60

Gln Gly Asn Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
            115                 120                 125

Arg Pro Gly Thr Met Val Ile Glu Ser Tyr Val Val Asp Val Pro Glu
        130                 135                 140

Gly Asn Thr Lys Asp Glu Thr Cys Tyr Phe Ser Leu Ala Asp Val Ser
145                 150                 155                 160

Glu Arg Leu Ala Val Ala Gly Thr Val Thr Glu Pro Ile Asp Arg Met
                165                 170                 175

<210> SEQ ID NO 78
<211> LENGTH: 180
<212> TYPE: PRT
<213> ORGANISM: Oryza sativa

<400> SEQUENCE: 78

Met Val Glu Met Asp Ala Gly Gly Arg Pro Glu Pro Ser Pro Pro Ser
 1               5                  10                  15

Gly Gln Cys Ser Ser Ala Val Thr Met Arg Ile Asn Ala Pro Val His
             20                  25                  30

Leu Val Trp Ser Ile Val Arg Arg Phe Glu Glu Pro His Ile Phe Gln
             35                  40                  45

Pro Phe Val Arg Gly Cys Thr Met Arg Gly Ser Thr Ser Leu Ala Val
         50                  55                  60

Gly Cys Val Arg Glu Val Asp Phe Lys Ser Gly Phe Ser Ala Lys Ser
 65                  70                  75                  80

Ser Val Glu Arg Leu Glu Ile Leu Asp Asp Lys Glu His Val Phe Gly
                 85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
            115                 120                 125

Ser Glu Ser Phe Val Ile Asp Val Pro Glu Gly Asn Thr Ala Asp Glu
        130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 79
<211> LENGTH: 215
<212> TYPE: PRT
<213> ORGANISM: Oryza sativa
```

```
<400> SEQUENCE: 79

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Leu Gly Lys Val Arg Glu Arg Leu Glu Ile Leu Asp
        115                 120                 125

Asp Glu Ser His Val Leu Ser Phe Arg Val Val Gly Gly Glu His Arg
    130                 135                 140

Leu Lys Asn Tyr Leu Ser Val Thr Thr Val His Pro Ser Pro Ser Ala
145                 150                 155                 160

Pro Thr Ala Ala Thr Val Val Val Glu Ser Tyr Val Val Asp Val Pro
                165                 170                 175

Pro Gly Asn Thr Pro Glu Asp Thr Arg Val Phe Val Asp Thr Ile Val
            180                 185                 190

Lys Cys Asn Leu Gln Ser Leu Ala Lys Thr Ala Glu Lys Leu Ala Ala
        195                 200                 205

Gly Ala Arg Ala Ala Gly Ser
    210                 215

<210> SEQ ID NO 80
<211> LENGTH: 186
<212> TYPE: PRT
<213> ORGANISM: Rheum australe

<400> SEQUENCE: 80

Met Asn Gly Asp Gly Tyr Gly Gly Ser Glu Glu Glu Phe Val Lys Arg
1               5                   10                  15

Tyr His Glu His Val Leu Ala Asp His Gln Cys Ser Ser Val Leu Val
            20                  25                  30

Glu His Ile Asn Ala Pro Leu His Leu Val Trp Ser Leu Val Arg Ser
        35                  40                  45

Phe Asp Gln Pro Gln Lys Tyr Lys Pro Phe Val Ser Arg Cys Val Val
    50                  55                  60

Gln Gly Gly Asp Leu Glu Ile Gly Ser Val Arg Glu Val Asp Val Lys
65                  70                  75                  80

Ser Gly Leu Pro Ala Thr Thr Ser Met Glu Glu Leu Glu Leu Leu Asp
                85                  90                  95

Asp Lys Glu His Val Leu Arg Val Lys Phe Val Gly Gly Asp His Arg
            100                 105                 110

Leu Lys Asn Tyr Ser Ser Ile Val Ser Leu His Pro Glu Ile Ile Gly
        115                 120                 125

Gly Arg Ser Gly Thr Met Val Ile Glu Ser Phe Ile Val Asp Ile Ala
    130                 135                 140
```

```
Asp Gly Asn Thr Lys Glu Glu Thr Cys Tyr Phe Ile Glu Ser Leu Ile
145                 150                 155                 160

Asn Cys Asn Leu Lys Ser Leu Ser Cys Val Ser Glu Arg Leu Ala Val
                165                 170                 175

Glu Asp Ile Ala Glu Arg Ile Ala Gln Met
            180                 185

<210> SEQ ID NO 81
<211> LENGTH: 254
<212> TYPE: PRT
<213> ORGANISM: Oryza sativa

<400> SEQUENCE: 81

Met Val Gly Leu Val Gly Gly Gly Trp Arg Val Gly Asp Asp Ala
1               5                   10                  15

Ala Gly Gly Gly Gly Gly Ala Val Ala Ala Gly Ala Ala Ala Ala
                20                  25                  30

Ala Glu Ala Glu His Met Arg Arg Leu His Ser Gln Gly Pro Arg Arg
            35                  40                  45

Ala Pro Val Gln Leu Arg Ala Arg Gln Ala His Gln Gly Ser Cys Ser
        50                  55                  60

Pro Pro Arg Ile Glu Cys Ala Asn Phe Ala Val Phe Leu Ala Ala Arg
65                  70                  75                  80

Asp Pro Lys Ile Val Trp Ser Leu Val Arg Ser Phe Asp Gln Pro Gln
                85                  90                  95

Arg Tyr Lys Pro Phe Val Ser Arg Cys Val Val Arg Gly Gly Asp Leu
                100                 105                 110

Glu Ile Gly Ser Val Arg Glu Val Asn Val Lys Thr Gly Leu Pro Ala
            115                 120                 125

Thr Thr Ser Thr Glu Arg Leu Glu Leu Leu Asp Asp Asp Glu His Ile
130                 135                 140

Leu Ser Val Lys Phe Val Gly Gly Asp His Arg Leu Arg Asn Tyr Ser
145                 150                 155                 160

Ser Ile Val Thr Val His Pro Glu Ser Ile Asp Gly Arg Pro Gly Thr
                165                 170                 175

Leu Val Ile Glu Ser Phe Val Val Asp Val Pro Asp Gly Asn Thr Lys
                180                 185                 190

Asp Glu Thr Cys Tyr Phe Val Glu Ala Val Ile Lys Cys Asn Leu Thr
            195                 200                 205

Ser Leu Ala Glu Met Val Arg Met Ile Ser Leu Val Leu Pro Phe Met
210                 215                 220

Leu Val Asp Arg Met Ser Gly Ile Thr Cys Glu Ser His Leu Glu Thr
225                 230                 235                 240

Thr Leu Val Arg Cys Gly Glu Tyr Ala Val Leu Ala His Val
                245                 250

<210> SEQ ID NO 82
<211> LENGTH: 186
<212> TYPE: PRT
<213> ORGANISM: Oryza sativa

<400> SEQUENCE: 82

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Gly
            20                  25                  30
```

Trp Asn Ala Pro Leu Ala Ala Val Trp Pro His Arg Ala Arg Val Arg
             35                  40                  45

Pro Thr Arg Ser Gly Thr Ser Thr Ser Ser Arg Ala Ser Ser Pro
 50                  55                  60

Pro Gly Asp Gly Ala Thr Val Gly Ser Val Arg Glu Val Ala Val Val
 65                  70                  75                  80

Ser Gly Leu Pro Ala Ser Thr Ser Thr Glu Arg Leu Glu Ile Leu Asp
                 85                  90                  95

Asp Asp Arg His Val Leu Ser Phe Arg Val Val Gly Gly Asp His Arg
            100                 105                 110

Leu Arg Asn Tyr Arg Ser Val Thr Ser Val Thr Glu Phe Ser Ser Pro
        115                 120                 125

Ser Ser Pro Pro Arg Pro Tyr Cys Val Val Val Glu Ser Tyr Val Val
130                 135                 140

Asp Val Pro Glu Gly Asn Thr Glu Asp Thr Arg Met Phe Thr Asp
145                 150                 155                 160

Thr Val Val Lys Leu Asn Leu Gln Lys Leu Ala Ala Val Ala Thr Ser
                165                 170                 175

Ser Ser Pro Pro Ala Ala Gly Asn His His
            180                 185

<210> SEQ ID NO 83
<211> LENGTH: 150
<212> TYPE: PRT
<213> ORGANISM: Oryza sativa

<400> SEQUENCE: 83

Met Glu Val Val Trp Ser Ile Val Arg Arg Phe Glu Pro His Ile
 1               5                   10                  15

Phe Gln Pro Phe Val Arg Gly Cys Thr Met Arg Gly Ser Thr Ser Leu
                20                  25                  30

Ala Val Gly Cys Val Arg Glu Val Asp Phe Lys Ser Gly Phe Pro Ala
            35                  40                  45

Lys Ser Ser Val Glu Arg Leu Glu Ile Leu Asp Asp Lys Glu His Val
 50                  55                  60

Phe Gly Val Arg Ile Ile Gly Gly Asp His Arg Leu Lys Asn Tyr Ser
 65                  70                  75                  80

Ser Val Leu Thr Ala Lys Pro Glu Val Ile Asp Gly Glu Pro Ala Thr
                 85                  90                  95

Leu Val Ser Glu Ser Phe Val Val Asp Val Pro Glu Gly Asn Thr Ala
            100                 105                 110

Asp Glu Thr Arg His Phe Val Glu Phe Leu Ile Arg Cys Asn Leu Arg
        115                 120                 125

Ser Leu Ala Met Val Ser Gln Arg Leu Leu Leu Ala Gln Gly Asp Leu
130                 135                 140

Ala Glu Pro Pro Gly Gln
145                 150

<210> SEQ ID NO 84
<211> LENGTH: 206
<212> TYPE: PRT
<213> ORGANISM: Oryza sativa

<400> SEQUENCE: 84

Met Pro Tyr Thr Ala Pro Arg Pro Ser Pro Gln His Ser Arg Ile
 1               5                   10                  15

```
Gly Gly Cys Gly Gly Gly Val Leu Lys Ala Ala Gly Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Arg Thr Ser Thr Ser Ser Gly
65                  70                  75                  80

Ala Ala Ala Ser Trp Thr Ala Thr Ala Thr Ala Gly Pro Leu Pro Val
                85                  90                  95

Gly Ser Val Arg Glu Phe Arg Val Leu Ser Gly Leu Pro Gly Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ser Asn Tyr Arg Ser Val
    130                 135                 140

Thr Thr Val His Glu Thr Ala Ala Gly Ala Ala Ala Val Val Val
145                 150                 155                 160

Glu Ser Tyr Val Val Asp Val Pro His Gly Asn Thr Ala Asp Glu Thr
                165                 170                 175

Arg Met Phe Val Asp Thr Ile Val Arg Cys Asn Leu Gln Ser Leu Ala
            180                 185                 190

Arg Thr Ala Glu Gln Leu Ala Leu Ala Ala Pro Arg Ala Ala
        195                 200                 205

<210> SEQ ID NO 85
<211> LENGTH: 396
<212> TYPE: PRT
<213> ORGANISM: Vitis vinifera
<220> FEATURE:
<221> NAME/KEY: VARIANT
<222> LOCATION: (1)..(396)
<223> OTHER INFORMATION: Xaa = any amino acid

<400> SEQUENCE: 85

Met Pro Ile Ser Ser Leu Pro Phe Ser Leu Tyr Thr Val Thr Pro Asn
1               5                   10                  15

Pro Leu Lys Leu Ile Thr Thr His Ala His Ala Phe Thr Pro His Thr
                20                  25                  30

His Ile Phe Thr Leu Lys Phe Met Ser His Thr Tyr Cys Pro His Ile
            35                  40                  45

His His Ile Thr Ser Ile His Tyr Thr His Leu Leu Xaa Pro Ile Pro
        50                  55                  60

His Met Pro Leu Gln Pro Pro Leu Pro Pro His Pro Ile Leu Pro Ser
65                  70                  75                  80

Met Pro Ala Phe Gln His Leu Tyr Ser Thr Asn Gln His Leu Gln Val
                85                  90                  95

Ala Leu Phe Ser Ala Arg Gly Pro Asn Ile Arg Asp Phe Asn Phe Gln
            100                 105                 110

Asp Ala Asp Leu Leu Lys Leu Asp Ile Leu Ala Pro Gly Ser Leu Ile
        115                 120                 125

Trp Ala Ala Trp Ser Pro Asn Gly Thr Asp Glu Ala Asn Tyr Val Gly
    130                 135                 140

Glu Gly Ser Pro Thr Val Ala Met Ile Ala Lys Arg Gly Pro Arg His
145                 150                 155                 160

Gly Lys Tyr Met Ala Phe Cys Xaa Met Tyr Arg Asp Asn Val Ala Pro
```

```
            165                 170                 175
Lys Gly Val Asn Xaa Ala Val Ala Thr Val Lys Thr Lys Arg Thr Ile
            180                 185                 190

Gln Leu Lys Thr Ser Leu Glu Ile Ala Cys His Tyr Ala Gly Ile Asn
            195                 200                 205

Ile Ser Gly Ile Asn Gly Glu Val Met Pro Gly Gln Trp Glu Tyr Gln
            210                 215                 220

Val Gly Pro Gly Gln Cys Ser Ser Leu Leu Ala Gln Arg Val His Val
225                 230                 235                 240

Pro Leu Ser Ala Val Gly Ser Val Val His Arg Phe Asp Lys Pro Gln
            245                 250                 255

Arg Tyr Gln His Val Ile Lys Ser Cys Arg Ile Glu Asp Gly Phe Glu
            260                 265                 270

Met Arg Met Gly Xaa Leu Arg Asp Val Asn Ile Ile Ser Gly Leu Pro
            275                 280                 285

Thr Ala Thr Asn Thr Gly Arg Leu Asp Met Gln Asp Asp Glu Arg His
            290                 295                 300

Val Thr Arg Cys Pro His Gln Arg Gln Ser Glu Ser Lys Tyr Thr Glu
305                 310                 315                 320

Asn Asn Asn Ser Asp Ala Ser Ser Ile Lys Ser Pro Ile Asn Gly Pro
            325                 330                 335

Ser Glu His Leu Lys Thr Ala Ala Ser Pro Lys Thr Glu Ser Ile Ile
            340                 345                 350

Val Ile Asp Thr Ser Lys Phe Leu Asn Glu Glu Asp Phe Glu Gly Lys
            355                 360                 365

Asp Glu Thr Ser Ser Ser Asn Gln Val Gln Ile Glu Asp Glu Asn Trp
            370                 375                 380

Glu Thr Arg Phe Pro Asn Thr Asp Ala Gly Ile Trp
385                 390                 395

<210> SEQ ID NO 86
<211> LENGTH: 443
<212> TYPE: PRT
<213> ORGANISM: Vitis vinifera
<220> FEATURE:
<221> NAME/KEY: VARIANT
<222> LOCATION: (1)..(443)
<223> OTHER INFORMATION: Xaa = any amino acid

<400> SEQUENCE: 86

Met Pro Ser Ala Xaa Lys Ser Ser Thr Val Pro Leu Ser Leu Xaa Gln
1               5                   10                  15

Phe Lys Leu Gly Leu Arg His Gly His Arg Val Ile Pro Trp Gly Asp
            20                  25                  30

Leu Asp Ser Leu Ala Met Leu Gln Arg Gln Leu Asp Val Asp Ile Leu
            35                  40                  45

Val Thr Gly His Thr His Arg Phe Thr Ala Tyr Lys His Glu Gly Gly
            50                  55                  60

Val Val Ile Asn Pro Gly Ser Ala Thr Gly Ala Phe Gly Ser Ile Thr
65                  70                  75                  80

Tyr Asp Val Asn Pro Ser Phe Val Leu Met Asp Ile Asp Gly Leu Arg
            85                  90                  95

Val Val Val Cys Val Tyr Glu Leu Ile Asp Glu Thr Ala Asn Ile Ile
            100                 105                 110

Lys Glu Leu His Ala Arg Lys Ile Ser Phe Gly Thr Lys Ser Met Ile
            115                 120                 125
```

```
Xaa Cys Leu Leu Leu Lys Arg Arg Ser Thr Pro Lys Phe Arg Lys
    130                 135                 140

Lys Leu Phe Leu Phe Gln Cys Arg Val Gln Met Thr Leu Thr Leu Thr
145                 150                 155                 160

Asn Leu Ala Val Ser Gly Ile Ala Gln Thr Leu Gln Val Asp Gln Trp
                165                 170                 175

Thr Val Cys Ala Leu Ile Phe Met Thr Arg Arg Asp Ile His Leu Asp
                180                 185                 190

Lys Ala Arg Phe Leu Asp Phe Lys Asp Met Gly Lys Leu Leu Ala Asp
            195                 200                 205

Ala Ser Gly Leu Arg Lys Ala Leu Ser Gly Gly Xaa Val Thr Ala Gly
210                 215                 220

Met Ala Ile Phe Asp Thr Met Arg His Ile Arg Pro Asp Val Pro Thr
225                 230                 235                 240

Val Cys Val Gly Leu Ala Ala Val Ala Met Ile Ala Lys Arg Gly Pro
                245                 250                 255

Arg His Gly Lys Tyr Met Ala Phe Cys Pro Met Tyr Arg Asp Asn Val
                260                 265                 270

Ala Pro Lys Gly Val Asn Val Ala Val Val Thr Val Lys Thr Lys Arg
            275                 280                 285

Thr Ile Gln Leu Lys Thr Ser Leu Glu Ile Ala Cys His Tyr Ala Gly
290                 295                 300

Ile Asn Ile Ser Gly Ile Asn Gly Glu Val Met Pro Gly Gln Trp Glu
305                 310                 315                 320

Tyr Gln Val Gly Pro Gly Gln Cys Ser Ser Leu Leu Ala Gln Arg Val
                325                 330                 335

His Val Pro Leu Ser Ala Val Gly Ser Val Val His Arg Phe Asp Lys
                340                 345                 350

Pro Gln Arg Tyr Gln His Val Ile Lys Ser Cys Arg Ile Glu Asp Gly
            355                 360                 365

Phe Glu Met Arg Met Gly Arg Leu Arg Asp Val Asn Ile Ile Ser Gly
370                 375                 380

Leu Pro Thr Ala Thr Asn Thr Gly Arg Leu Asp Met Gln Asp Asp Glu
385                 390                 395                 400

Xaa His Val Thr Arg Cys Pro His Gln Arg Gln Ser Glu Ser Lys Tyr
                405                 410                 415

Thr Glu Asn Asn Asn Ser Asp Ala Ser Ser Val Lys Ser Pro Ile Asn
                420                 425                 430

Gly Pro Ser Glu His Leu Lys Thr Ala Ala Xaa
            435                 440

<210> SEQ ID NO 87
<211> LENGTH: 95
<212> TYPE: PRT
<213> ORGANISM: Oryza sativa

<400> SEQUENCE: 87

Glu Ile Gly Ser Val Arg Glu Val Asn Val Lys Thr Gly Leu Pro Ala
1               5                   10                  15

Thr Thr Ser Thr Glu Arg Leu Glu Leu Leu Asp Asp Asp Glu His Ile
                20                  25                  30

Leu Ser Val Lys Phe Val Gly Gly Asp His Arg Leu Arg Asn Tyr Ser
            35                  40                  45

Ser Ile Val Thr Val His Pro Glu Ser Ile Asp Gly Arg Pro Gly Thr
```

Leu Val Ile Glu Ser Phe Val Asp Val Pro Asp Gly Asn Thr Lys
65                  70                  75                  80

Asp Glu Thr Cys Tyr Phe Val Glu Ala Val Ile Lys Cys Asn Leu
                85                  90                  95

<210> SEQ ID NO 88
<211> LENGTH: 191
<212> TYPE: PRT
<213> ORGANISM: Zea mays

<400> SEQUENCE: 88

Met Val Val Glu Met Asp Gly Gly Val Gly Val Ala Ala Gly Gly
1               5                   10                  15

Gly Gly Ala Gln Thr Pro Ala Pro Pro Pro Arg Arg Trp Arg Leu
                20                  25                  30

Ala Asp Glu Arg Cys Asp Leu Arg Ala Met Glu Thr Asp Tyr Val Arg
            35                  40                  45

Arg Phe His Arg His Glu Pro Arg Asp His Gln Cys Ser Ser Ala Val
        50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
130                 135                 140

Leu Gln Val Cys Ser Val Leu His Leu Ser Ile Phe Cys Ala Ala His
145                 150                 155                 160

Ala Arg Tyr Phe Ala His His Leu Lys Cys Val Leu Glu Phe Leu Cys
                165                 170                 175

Gln Met His Leu Asp Val Leu Pro Cys Asp Asp Ala Ile Leu Glu
            180                 185                 190

<210> SEQ ID NO 89
<211> LENGTH: 239
<212> TYPE: PRT
<213> ORGANISM: Oryza sativa

<400> SEQUENCE: 89

Met Asn Gly Cys Thr Gly Gly Ala Gly Gly Val Ala Ala Gly Arg Leu
1               5                   10                  15

Pro Ala Val Ser Leu Gln Gln Ala Gln Trp Lys Leu Val Asp Glu Arg
                20                  25                  30

Cys Glu Leu Arg Glu Glu Met Glu Tyr Val Arg Arg Phe His Arg
            35                  40                  45

His Glu Ile Gly Ser Asn Gln Cys Asn Ser Phe Ile Ala Lys His Val
        50                  55                  60

Arg Ala Pro Leu Gln Asn Val Trp Ser Leu Val Arg Arg Phe Asp Gln
65                  70                  75                  80

Pro Gln Ile Tyr Lys Pro Phe Val Arg Lys Cys Val Met Arg Gly Asn
                85                  90                  95

Val Glu Thr Gly Ser Val Arg Glu Ile Ile Val Gln Ser Gly Leu Pro

```
              100                 105                 110
Ala Thr Arg Ser Ile Glu Arg Leu Glu Phe Leu Asp Asp Asn Glu Tyr
            115                 120                 125

Ile Leu Arg Val Lys Phe Ile Gly Gly Asp His Met Leu Lys Lys Arg
            130                 135                 140

Ile Pro Lys Lys Thr Tyr Ala Ile Ser Ser Arg Thr Cys Ser Asp Ser
145                 150                 155                 160

Ala Ile Ile Ala Val Gly Gln Ser Asn Cys Ala Pro Glu Ile Thr Ala
            165                 170                 175

Met Asn Gly Gly Val Ser Ile Gln Pro Trp Leu Ile Leu Leu Ala Phe
            180                 185                 190

Phe Ser Ser Pro Ser Asn Gln Thr Asn Pro Asp Ser Leu Arg Asp Met
            195                 200                 205

His Pro Gly Ser Trp Phe Gln Ile Leu Leu Val Leu Ala Met Phe Thr
            210                 215                 220

Cys Ser Lys Gly Ser Val Leu Pro Pro Ser Glu Lys Val Asn Val
225                 230                 235
```

<210> SEQ ID NO 90
<211> LENGTH: 188
<212> TYPE: PRT
<213> ORGANISM: Zea mays

<400> SEQUENCE: 90

```
Met Glu Pro His Met Glu Ser Ala Leu Arg Gln Gly Leu Ser Glu Ala
1               5                   10                  15

Glu Gln Arg Glu Leu Glu Gly Val Val Arg Ala His His Thr Phe Pro
            20                  25                  30

Gly Arg Ala Pro Gly Thr Cys Thr Ser Leu Val Thr Gln Arg Val Asp
        35                  40                  45

Ala Pro Leu Ala Ala Val Trp Pro Ile Val Arg Gly Phe Gly Ser Pro
    50                  55                  60

Gln Arg Tyr Lys His Phe Ile Lys Ser Cys Asp Leu Lys Ala Gly Asp
65                  70                  75                  80

Gly Ala Thr Val Gly Ser Val Arg Glu Val Thr Val Val Ser Gly Leu
                85                  90                  95

Pro Ala Ser Thr Ser Thr Glu Arg Leu Glu Ile Leu Asp Asp His Arg
            100                 105                 110

His Ile Leu Ser Phe Arg Val Val Gly Gly Asp His Arg Leu Arg Asn
            115                 120                 125

Tyr Arg Ser Val Thr Ser Val Thr Glu Phe Gln Pro Gly Pro Tyr Cys
        130                 135                 140

Val Val Leu Glu Ser Tyr Val Val Asp Val Pro Asp Gly Asn Thr Glu
145                 150                 155                 160

Glu Asp Thr Arg Met Phe Thr Asp Thr Val Lys Leu Asn Leu Gln
                165                 170                 175

Lys Leu Ala Ala Ile Ala Thr Ser Ser Ala Asn
            180                 185
```

<210> SEQ ID NO 91
<211> LENGTH: 205
<212> TYPE: PRT
<213> ORGANISM: Zea mays

<400> SEQUENCE: 91

Met Asp Gln Gln Gly Ala Gly Gly Asp Val Glu Val Pro Ala Gly Leu

```
            1               5                  10                 15
Gly Leu Thr Ala Ala Glu Tyr Glu Gln Leu Arg Pro Thr Val Asp Ala
                20                 25                 30

His His Arg Tyr Ala Val Gly Glu Gly Gln Cys Ser Ser Leu Leu Ala
                35                 40                 45

Gln Arg Ile His Ala Pro Pro Ala Ala Val Trp Ala Ile Val Arg Arg
    50                 55                 60

Phe Asp Cys Pro Gln Val Tyr Lys His Phe Ile Arg Ser Cys Ala Val
65                  70                 75                  80

Arg Pro Asp Pro Asp Ala Gly Asp Ala Leu Arg Pro Gly Arg Leu Arg
                85                 90                 95

Glu Val Cys Val Ile Ser Gly Leu Pro Ala Ser Thr Ser Thr Glu Arg
               100                105                110

Leu Asp His Leu Asp Asp Ala Ala Arg Val Phe Gly Phe Ser Ile Thr
               115                120                125

Gly Gly Glu His Arg Leu Arg Asn Tyr Arg Ser Val Thr Thr Val Ser
130                135                140

Glu Leu Ala Gly Pro Gly Ile Cys Thr Val Val Leu Glu Ser Tyr Ala
145                150                155                160

Val Asp Val Pro Asp Gly Asn Thr Glu Asp Thr Arg Leu Phe Ala
               165                170                175

Asp Thr Val Ile Arg Leu Asn Leu Gln Lys Leu Lys Ser Val Ala Glu
               180                185                190

Ala Ser Thr Ser Ser Ser Ala Pro Pro Pro Ser Glu
               195                200                205

<210> SEQ ID NO 92
<211> LENGTH: 220
<212> TYPE: PRT
<213> ORGANISM: Zea mays

<400> SEQUENCE: 92

Met Pro Cys Ile Gln Ala Ser Ser Pro Gly Gly Met Pro His Gln His
1               5                  10                 15

Gly Arg Gly Arg Val Leu Gly Gly Val Gly Cys Ala Ala Glu Val
                20                 25                 30

Ala Ala Ala Val Ala Ala Ser Ala Gly Gly Met Arg Cys Gly Ala His
                35                 40                 45

Asp Gly Glu Val Pro Ala Glu Ala Ala Arg His His Glu His Ala Ala
    50                 55                 60

Ala Gly Pro Gly Arg Cys Cys Ser Ala Val Val Gln His Val Ala Ala
65                  70                 75                  80

Pro Ala Ala Ala Val Trp Ser Val Val Arg Arg Phe Asp Gln Pro Gln
                85                 90                 95

Val Tyr Lys Arg Phe Val Arg Ser Cys Ala Leu Leu Ala Gly Asp Gly
               100                105                110

Gly Val Gly Thr Leu Arg Glu Val Arg Val Val Ser Gly Leu Pro Ala
               115                120                125

Ala Ser Ser Arg Glu Arg Leu Glu Val Leu Asp Asp Glu Ser His Val
130                135                140

Leu Ser Phe Arg Val Val Gly Gly Glu His Arg Leu Arg Asn Tyr Leu
145                150                155                160

Ser Val Thr Thr Val His Pro Ser Pro Ala Ala Pro Asp Ala Ala Thr
               165                170                175
```

```
Val Val Val Glu Ser Tyr Val Val Asp Val Pro Pro Gly Asn Thr Pro
            180                 185                 190

Glu Asp Thr Arg Val Phe Val Asp Thr Ile Val Lys Cys Asn Leu Gln
        195                 200                 205

Ser Leu Ala Thr Thr Ala Glu Lys Leu Ala Ala Val
    210                 215                 220

<210> SEQ ID NO 93
<211> LENGTH: 221
<212> TYPE: PRT
<213> ORGANISM: Glycine max

<400> SEQUENCE: 93

Met Glu Lys Ala Glu Ser Ser Ala Ser Thr Ser Glu Pro Asp Ser Asp
1               5                   10                  15

Glu Asn His His Arg His Pro Thr Asn His Ile Asn Pro Pro Ser
            20                  25                  30

Gly Leu Thr Pro Leu Glu Phe Ala Ser Leu Ile Pro Ser Val Ala Glu
        35                  40                  45

His His Ser Tyr Leu Val Gly Ser Gly Gln Cys Ser Ser Leu Leu Ala
    50                  55                  60

Gln Arg Val Gln Ala Pro Pro Asp Ala Val Trp Ser Val Val Arg Arg
65              70                  75                  80

Phe Asp Lys Pro Gln Thr Tyr Lys His Phe Ile Lys Ser Cys Ala Val
                85                  90                  95

Lys Glu Pro Phe His Met Ala Val Gly Val Thr Arg Asp Val Asn Val
            100                 105                 110

Ile Ser Gly Leu Pro Ala Ala Thr Ser Thr Glu Arg Leu Asp Leu Leu
        115                 120                 125

Asp Asp Ile Arg Cys Val Thr Gly Phe Ser Ile Ile Gly Gly Glu His
    130                 135                 140

Arg Leu Arg Asn Tyr Arg Ser Val Thr Thr Val His Ser Phe Glu Asp
145                 150                 155                 160

Asp Ala Asp Asp Gly Lys Ile Tyr Thr Val Val Leu Glu Ser Tyr Val
                165                 170                 175

Val Asp Val Pro Asp Gly Asn Thr Glu Glu Asp Thr Arg Leu Phe Ala
            180                 185                 190

Asp Thr Val Val Lys Leu Asn Leu Gln Lys Leu Ala Ser Val Thr Glu
        195                 200                 205

Gly Thr Asn Arg Asp Gly Asp Gly Lys Ser His Ser Arg
    210                 215                 220

<210> SEQ ID NO 94
<211> LENGTH: 214
<212> TYPE: PRT
<213> ORGANISM: Glycine max

<400> SEQUENCE: 94

Met Glu Lys Thr His Ser Ser Ala Glu Gln Asp Pro Thr Arg
1               5                   10                  15

Arg His Leu Asp Pro Pro Gly Leu Thr Ala Glu Glu Phe Glu Asp
            20                  25                  30

Leu Lys Pro Ser Val Leu Glu His His Thr Tyr Ser Val Thr Pro Thr
        35                  40                  45

Arg Gln Ser Ser Ser Leu Leu Ala Gln Arg Ile His Ala Pro Pro His
    50                  55                  60
```

```
Ala Val Trp Ser Val Val Arg Cys Phe Asp Asn Pro Gln Ala Tyr Lys
 65                  70                  75                  80

His Phe Ile Lys Ser Cys His Val Lys Glu Gly Phe Gln Leu Ala Val
             85                  90                  95

Gly Ser Thr Arg Asp Val His Val Ile Ser Gly Leu Pro Ala Ala Thr
            100                 105                 110

Ser Thr Glu Arg Leu Asp Leu Leu Asp Asp Arg His Val Ile Gly
        115                 120                 125

Phe Thr Ile Val Gly Gly Asp His Arg Leu Arg Asn Tyr Arg Ser Val
130                 135                 140

Thr Ser Val His Gly Phe Glu Cys Asp Gly Lys Ile Trp Thr Val Val
145                 150                 155                 160

Leu Glu Ser Tyr Val Val Asp Val Pro Glu Gly Asn Thr Glu Glu Asp
                165                 170                 175

Thr Arg Leu Phe Ala Asp Thr Val Val Lys Leu Asn Leu Gln Lys Leu
            180                 185                 190

Ala Ser Val Ser Glu Gly Met Cys Gly Asp Gly Asp Gly Asp Gly Asp
            195                 200                 205

Gly Lys Gly Asn Lys Ser
        210
```

<210> SEQ ID NO 95
<211> LENGTH: 216
<212> TYPE: PRT
<213> ORGANISM: Glycine max

<400> SEQUENCE: 95

```
Met Leu Gln Asn Ser Ser Met Ser Ser Leu Leu Leu His Arg Ile Asn
  1               5                  10                  15

Gly Gly Gly Gly Ala Thr Thr Ala Thr Asn Cys His Asp Thr Val Phe
             20                  25                  30

Met Thr Val Pro Asp Gly Val Ala Arg Tyr His Thr His Ala Val Ala
         35                  40                  45

Pro Asn Gln Cys Cys Ser Ser Val Ala Gln Glu Ile Gly Ala Ser Val
 50                  55                  60

Ala Thr Val Trp Ser Val Leu Arg Arg Phe Asp Asn Pro Gln Ala Tyr
 65                  70                  75                  80

Lys His Phe Val Lys Ser Cys His Val Ile Gly Gly Asp Gly Asp Val
                 85                  90                  95

Gly Thr Leu Arg Glu Val His Val Ile Ser Gly Leu Pro Ala Ala Arg
            100                 105                 110

Ser Thr Glu Arg Leu Glu Ile Leu Asp Asp Glu Arg His Val Ile Ser
        115                 120                 125

Phe Ser Val Val Gly Gly Asp His Arg Leu Ala Asn Tyr Arg Ser Val
130                 135                 140

Thr Thr Leu His Pro Thr Ala Ser Ser Ala Ser Gly Gly Cys Ser Gly
145                 150                 155                 160

Thr Val Val Glu Ser Tyr Val Val Asp Val Pro Pro Gly Asn Thr
                165                 170                 175

Arg Glu Asp Thr Arg Val Phe Val Asp Thr Ile Val Lys Cys Asn Leu
            180                 185                 190

Gln Ser Leu Ala Gln Thr Ala Glu Asn Leu Thr Leu Arg Lys Asn Asn
        195                 200                 205

Asn Asn Asp Tyr Lys Cys Cys Ser
210                 215
```

<210> SEQ ID NO 96
<211> LENGTH: 208
<212> TYPE: PRT
<213> ORGANISM: Glycine max

<400> SEQUENCE: 96

```
Met Thr Ser Leu Gln Phe His Arg Phe Asn Pro Ala Thr Asp Thr Ser
1               5                   10                  15

Thr Ala Ile Ala Asn Gly Val Asn Cys Pro Lys Pro Ser Thr Leu
            20                  25                  30

Arg Leu Leu Ala Lys Val Ser Leu Ser Val Pro Glu Thr Val Ala Arg
        35                  40                  45

His His Ala His Pro Val Gly Pro Asn Gln Cys Cys Ser Val Val Ile
    50                  55                  60

Gln Ala Ile Asp Ala Pro Val Ser Ala Val Trp Pro Val Val Arg Arg
65                  70                  75                  80

Phe Asp Asn Pro Gln Ala Tyr Lys His Phe Val Lys Ser Cys His Val
                85                  90                  95

Val Ala Ala Ala Gly Gly Gly Glu Asp Gly Ile Arg Val Gly Ala Leu
            100                 105                 110

Arg Glu Val Arg Val Val Ser Gly Leu Pro Ala Val Ser Ser Thr Glu
        115                 120                 125

Arg Leu Glu Ile Leu Asp Asp Glu Arg His Val Met Ser Phe Ser Val
    130                 135                 140

Val Gly Gly Asp His Arg Leu Arg Asn Tyr Arg Ser Val Thr Thr Leu
145                 150                 155                 160

His Gly Asp Gly Asn Gly Gly Thr Val Val Ile Glu Ser Tyr Val Val
                165                 170                 175

Asp Val Pro Pro Gly Asn Thr Lys Glu Glu Thr Cys Val Phe Val Asp
            180                 185                 190

Thr Ile Val Arg Cys Asn Leu Gln Ser Leu Ala Gln Ile Ala Glu Thr
        195                 200                 205
```

<210> SEQ ID NO 97
<211> LENGTH: 176
<212> TYPE: PRT
<213> ORGANISM: Glycine max

<400> SEQUENCE: 97

```
Ala Tyr Pro Val Leu Gly Leu Thr Pro Glu Glu Phe Ser Glu Leu Glu
1               5                   10                  15

Ser Ile Ile Asn Thr His His Lys Phe Glu Pro Ser Pro Glu Ile Cys
            20                  25                  30

Ser Ser Ile Ile Ala Gln Arg Ile Asp Ala Pro Ala His Thr Val Trp
        35                  40                  45

Pro Leu Val Arg Ser Phe Glu Asn Pro Gln Lys Tyr Lys His Phe Val
    50                  55                  60

Lys Ser Cys Asn Met Arg Ser Gly Asp Gly Gly Val Gly Ser Ile Arg
65                  70                  75                  80

Glu Val Thr Val Val Ser Gly Leu Pro Ala Ser Thr Ser Thr Glu Arg
                85                  90                  95

Leu Glu Ile Leu Asp Asp Asp Lys His Leu Leu Ser Phe Arg Val Val
            100                 105                 110

Gly Gly Glu His Arg Leu His Asn Tyr Arg Ser Val Thr Ser Val Asn
        115                 120                 125
```

```
Glu Phe Lys Asn Pro Asp Asn Gly Lys Val Tyr Thr Ile Val Leu Glu
            130                 135                 140

Ser Tyr Val Val Asp Ile Pro Glu Gly Asn Thr Gly Val Asp Thr Lys
145                 150                 155                 160

Met Phe Val Asp Thr Val Val Lys Leu Asn Leu Gln Lys Leu Gly Glu
                165                 170                 175

<210> SEQ ID NO 98
<211> LENGTH: 172
<212> TYPE: PRT
<213> ORGANISM: Glycine max

<400> SEQUENCE: 98

Glu Phe Thr Glu Leu Glu Ser Thr Ile Asn Thr His His Lys Phe Glu
1               5                   10                  15

Ala Ser Pro Glu Ile Cys Ser Ser Ile Ile Ala Gln Arg Ile Asp Ala
                20                  25                  30

Pro Ala His Thr Val Trp Pro Leu Val Arg Ser Phe Glu Asn Pro Gln
            35                  40                  45

Lys Tyr Lys His Phe Val Lys Ser Cys Asn Met Arg Ser Gly Asp Gly
50                  55                  60

Gly Val Gly Ser Ile Arg Glu Val Thr Val Val Ser Gly Leu Pro Ala
65                  70                  75                  80

Ser Thr Ser Thr Glu Arg Leu Glu Ile Leu Asp Asp Asp Asn His Leu
                85                  90                  95

Leu Ser Phe Arg Val Val Gly Gly Glu His Arg Leu His Asn Tyr Arg
            100                 105                 110

Ser Val Thr Ser Val Asn Glu Phe Lys Arg Pro Asp Asn Gly Lys Val
        115                 120                 125

Tyr Thr Ile Val Leu Glu Ser Tyr Val Val Asp Ile Pro Glu Gly Asn
    130                 135                 140

Thr Gly Val Asp Thr Lys Met Phe Val Asp Thr Val Val Lys Leu Asn
145                 150                 155                 160

Leu Gln Lys Leu Gly Glu Val Ala Met Ala Thr Asn
                165                 170

<210> SEQ ID NO 99
<211> LENGTH: 191
<212> TYPE: PRT
<213> ORGANISM: Glycine max

<400> SEQUENCE: 99

Met Thr Glu Leu Ser Ser Arg Glu Val Glu Tyr Ile Arg Arg His His
1               5                   10                  15

Ser Lys Ala Ala Glu Asp Asn Gln Cys Ala Ser Ala Leu Val Lys His
                20                  25                  30

Ile Arg Ala Pro Leu Pro Leu Val Trp Ser Leu Val Arg Arg Phe Asp
            35                  40                  45

Glu Pro Gln Lys Tyr Lys Pro Phe Val Ser Arg Cys Val Val Arg Gly
50                  55                  60

Asn Leu Glu Ile Gly Ser Leu Arg Glu Val Asp Val Lys Ser Gly Leu
65                  70                  75                  80

Pro Ala Thr Thr Ser Thr Glu Arg Leu Glu Ile Leu Asp Asp Asn His
                85                  90                  95

His Ile Leu Ser Val Arg Ile Ile Gly Gly Asp His Arg Leu Arg Asn
            100                 105                 110
```

```
Tyr Ser Ser Ile Met Ser Leu His Pro Glu Ile Val Asp Gly Arg Pro
            115                 120                 125

Gly Thr Leu Val Ile Glu Ser Phe Val Val Asp Ile Pro Glu Gly Asn
        130                 135                 140

Thr Lys Asp Glu Thr Cys Tyr Phe Val Glu Ala Leu Ile Lys Cys Asn
145                 150                 155                 160

Leu Lys Ser Leu Ala Asp Val Ser Gly Leu Thr Leu Gln Asp His
                165                 170                 175

Thr Glu Pro Ile Asp Arg Lys Tyr Glu Leu Leu Ile Thr Arg Gly
            180                 185                 190

<210> SEQ ID NO 100
<211> LENGTH: 185
<212> TYPE: PRT
<213> ORGANISM: Glycine max

<400> SEQUENCE: 100

Met Asn Gly Gly Glu Ser Tyr Gly Ala Ile Glu Thr Gln Tyr Ile Arg
1               5                   10                  15

Arg His His Lys His Glu Pro Arg Glu Asn Gln Cys Thr Ser Ala Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Met Gln Gly Asp Leu Gly Ile Gly Ser Val Arg Glu Val Asn Val Lys
65                  70                  75                  80

Ser Gly Leu Pro Ala Thr Thr Ser Thr Glu Arg Leu Glu Gln Leu Asp
                85                  90                  95

Asp Glu Glu His Ile Leu Gly Ile Arg Ile Val Gly Gly Asp His Arg
            100                 105                 110

Leu Arg Asn Tyr Ser Ser Ile Ile Thr Val His Pro Glu Val Ile Asp
        115                 120                 125

Gly Arg Pro Gly Thr Met Val Ile Glu Ser Phe Val Val Asp Val Pro
    130                 135                 140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
                165                 170                 175

Gln Gly Arg Thr Asn Pro Ile Asn His
            180                 185

<210> SEQ ID NO 101
<211> LENGTH: 178
<212> TYPE: PRT
<213> ORGANISM: Glycine max

<400> SEQUENCE: 101

Met Ser Pro Asn Asn Pro Ser Thr Ile Val Ser Asp Ala Val Ala Arg
1               5                   10                  15

His His Thr His Val Val Ser Pro His Gln Cys Cys Ser Ala Val Val
            20                  25                  30

Gln Glu Ile Ala Ala Pro Val Ser Thr Val Trp Ser Val Val Arg Arg
        35                  40                  45

Phe Asp Asn Pro Gln Ala Tyr Lys His Phe Val Lys Ser Cys His Val
    50                  55                  60
```

```
Ile Leu Gly Asp Gly Asp Val Gly Thr Leu Arg Glu Val Arg Val Ile
 65                  70                  75                  80

Ser Gly Leu Pro Ala Ala Val Ser Thr Glu Arg Leu Asp Val Leu Asp
                 85                  90                  95

Asp Glu Arg His Val Ile Gly Phe Ser Met Val Gly Gly Asp His Arg
            100                 105                 110

Leu Ser Asn Tyr Arg Ser Val Thr Ile Leu His Pro Arg Ser Ala Thr
        115                 120                 125

Asp Thr Val Val Glu Ser Tyr Val Val Asp Val Pro Ala Gly Asn
    130                 135                 140

Thr Thr Glu Asp Thr Arg Val Phe Val Asp Thr Ile Leu Arg Cys Asn
145                 150                 155                 160

Leu Gln Ser Leu Ala Lys Phe Ala Glu Asn Leu Thr Asn Lys Leu His
                165                 170                 175

Gln Arg

<210> SEQ ID NO 102
<211> LENGTH: 246
<212> TYPE: PRT
<213> ORGANISM: Glycine max

<400> SEQUENCE: 102

Met Ser Arg Ser His Asn Lys Arg Lys Pro Phe Ser Phe Ile Phe Lys
  1               5                  10                  15

Ile Thr Leu Leu Glu Leu Leu Ser Ser Leu Leu Ser Ser Ser Leu Arg
                 20                  25                  30

Phe Ala Met Asp Lys Thr His Ser Gly Glu Glu Gln Asp Pro Asn Pro
             35                  40                  45

Thr His Pro Thr Arg Asn His Leu Asp Pro Pro Gly Leu Thr Pro
         50                  55                  60

Glu Glu Phe Glu Asp Leu Lys Pro Ser Val Leu Glu His His Thr Tyr
 65                  70                  75                  80

Ser Val Thr Pro Thr Arg Gln Cys Ser Ser Leu Leu Ala Gln Arg Ile
                 85                  90                  95

His Ala Pro Pro His Thr Val Trp Thr Val Arg Cys Phe Asp Asn
            100                 105                 110

Pro Gln Ala Tyr Lys His Phe Ile Lys Ser Cys His Val Lys Glu Gly
        115                 120                 125

Phe Gln Leu Ala Val Gly Ser Thr Arg Asp Val His Val Ile Ser Gly
    130                 135                 140

Leu Pro Ala Ala Thr Ser Thr Glu Arg Leu Asp Leu Leu Asp Asp Asp
145                 150                 155                 160

Arg His Val Ile Gly Phe Thr Ile Val Gly Gly Asp His Arg Leu Arg
                165                 170                 175

Asn Tyr Arg Ser Val Thr Ser Val His Gly Phe Glu Arg Asp Gly Lys
            180                 185                 190

Ile Trp Thr Val Val Leu Glu Ser Tyr Val Val Asp Val Pro Glu Gly
        195                 200                 205

Asn Thr Glu Glu Asp Thr Arg Leu Phe Ala Asp Thr Val Val Lys Leu
    210                 215                 220

Asn Leu Gln Lys Leu Ala Ser Val Thr Glu Gly Met Cys Gly Asp Ser
225                 230                 235                 240

Asp Gly Lys Gly Asn Asn
                245
```

<210> SEQ ID NO 103
<211> LENGTH: 223
<212> TYPE: PRT
<213> ORGANISM: Glycine max

<400> SEQUENCE: 103

```
Met Glu Lys Ala Glu Ser Ser Ala Ser Thr Ser Glu Pro Asp Ser Asp
1               5                   10                  15
Asp Asn His His Arg His Pro Thr Asn His Leu Asn Pro Pro Ser
            20                  25                  30
Gly Leu Thr Pro Leu Glu Phe Ala Ser Leu Val Pro Ser Val Ala Glu
        35                  40                  45
His His Ser Tyr Leu Val Gly Pro Gly Gln Cys Ser Ser Leu Leu Ala
    50                  55                  60
Gln Arg Val His Ala Pro Pro Asp Ala Val Trp Ser Phe Val Arg Arg
65                  70                  75                  80
Phe Asp Lys Pro Gln Thr Tyr Lys His Phe Ile Lys Ser Cys Ala Val
                85                  90                  95
Lys Glu Pro Phe His Met Ala Val Gly Val Thr Arg Asp Val Asn Val
            100                 105                 110
Ile Ser Gly Leu Pro Ala Ala Thr Ser Thr Glu Arg Leu Asp Phe Leu
        115                 120                 125
Asp Asp Val Arg Arg Val Thr Gly Phe Ser Ile Ile Gly Gly Glu His
    130                 135                 140
Arg Leu Arg Asn Tyr Arg Ser Val Thr Thr Val His Ser Phe Asp Asp
145                 150                 155                 160
Asp Asn Ala Ser Ala Asp Gly Lys Ile Tyr Thr Val Val Leu Glu Ser
                165                 170                 175
Tyr Val Val Asp Val Pro Asp Gly Asn Thr Glu Glu Asp Thr Arg Leu
            180                 185                 190
Phe Ala Asp Thr Val Val Lys Leu Asn Leu Gln Lys Leu Ala Ser Val
        195                 200                 205
Thr Glu Gly Thr Asn Gly Asp Gly Asp Gly Lys Pro His Ser Arg
    210                 215                 220
```

<210> SEQ ID NO 104
<211> LENGTH: 229
<212> TYPE: PRT
<213> ORGANISM: Glycine max

<400> SEQUENCE: 104

```
Met Pro Ser Ser Leu His Phe Asp Arg Phe Asn Pro Ile Thr His Ala
1               5                   10                  15
Ala Thr Thr Val Ala Ile Ala Asn Gly Val Asn Cys Pro Lys Gln Pro
            20                  25                  30
Gln Ala Pro Pro Ser Ser Thr Ala Ala Arg Arg Leu Val Val Pro Ser
        35                  40                  45
Leu Ser Ser Gly Arg Gly Ile Ala Ala Pro Asp Thr Val Ala Leu His
    50                  55                  60
His Ala His Val Val Asp Pro Asn Gln Cys Cys Ser Ile Val Thr Gln
65                  70                  75                  80
His Ile Asn Ala Pro Val Ser Ala Val Trp Ala Val Val Arg Arg Phe
                85                  90                  95
Asp Asn Pro Gln Gly Tyr Lys Asn Phe Val Arg Ser Cys His Val Ile
            100                 105                 110
```

Thr Gly Asp Gly Ile Arg Val Gly Ala Val Arg Glu Val Arg Val Val
        115                 120                 125

Ser Gly Leu Pro Ala Glu Thr Ser Thr Glu Arg Leu Glu Ile Leu Asp
    130                 135                 140

Asp Glu Arg His Val Ile Ser Phe Ser Met Val Gly Asp His Arg
145                 150                 155                 160

Leu Arg Asn Tyr Gln Ser Val Thr Thr Leu His Ala Asn Gly Asn Gly
                165                 170                 175

Thr Leu Val Ile Glu Ser Tyr Val Val Asp Val Pro Gln Gly Asn Thr
            180                 185                 190

Lys Glu Glu Thr Cys Val Phe Val Asp Thr Ile Val Arg Cys Asn Leu
        195                 200                 205

Gln Ser Leu Ala Gln Ile Ala Glu Asn Arg Thr Asn Asn Cys Glu His
    210                 215                 220

Thr Ala Gln His Cys
225

<210> SEQ ID NO 105
<211> LENGTH: 191
<212> TYPE: PRT
<213> ORGANISM: Glycine max

<400> SEQUENCE: 105

Met Asn Gly Ile Gly Asn Asp Gly Gly Gly Leu Ser Asn Val Glu
1               5                   10                  15

Met Glu Tyr Ile Arg Arg His His Arg His Glu Pro Gly Glu Asn Gln
            20                  25                  30

Cys Gly Ser Ala Leu Val Lys His Ile Arg Ala Pro Val Pro Gln Val
        35                  40                  45

Trp Ser Leu Val Arg Arg Phe Asp Gln Pro Gln Lys Tyr Lys Pro Phe
    50                  55                  60

Val Ser Arg Cys Val Val Arg Gly Asn Leu Glu Ile Gly Ser Leu Arg
65                  70                  75                  80

Glu Val Asp Val Lys Ser Gly Leu Pro Ala Thr Thr Ser Thr Glu Arg
                85                  90                  95

Leu Glu Leu Leu Asp Asp Asn Glu His Leu Leu Ser Ile Arg Ile Ile
            100                 105                 110

Gly Gly Asp His Arg Leu Arg Asn Tyr Ser Ser Ile Met Ser Leu His
        115                 120                 125

Pro Glu Ile Ile Asp Gly Arg Pro Gly Thr Leu Val Ile Glu Ser Phe
    130                 135                 140

Val Val Asp Val Pro Glu Gly Asn Thr Lys Asp Glu Thr Cys Tyr Phe
145                 150                 155                 160

Val Glu Ala Leu Ile Lys Cys Asn Leu Lys Ser Leu Ala Asp Val Ser
                165                 170                 175

Glu Gly Ile Ala Val Gln Asp Arg Thr Glu Pro Ile Asp Arg Ile
            180                 185                 190

<210> SEQ ID NO 106
<211> LENGTH: 169
<212> TYPE: PRT
<213> ORGANISM: Glycine max

<400> SEQUENCE: 106

Met Val Ala Arg His His Ala His Ala Val Gly Pro Asn Gln Cys Cys
1               5                   10                  15

Ser Phe Val Ile Gln Ala Ile Asp Ala Pro Val Ser Ala Val Trp Pro
            20                  25                  30

Val Val Arg Arg Phe Asp Asn Pro Gln Ala Tyr Lys His Phe Val Lys
        35                  40                  45

Ser Cys His Val Val Ala Ala Gly Gly Ala Gly Asp Gly Gly Ile
50                  55                  60

His Val Gly Ala Leu Arg Glu Val Arg Val Val Ser Gly Leu Pro Ala
65                  70                  75                  80

Val Ser Ser Thr Glu Arg Leu Glu Ile Leu Asp Asp Glu Arg His Val
                85                  90                  95

Met Ser Phe Ser Val Val Gly Gly Asp His Arg Leu Arg Asn Tyr Arg
                100                 105                 110

Ser Val Thr Thr Leu His Gly Asp Gly Ser Asn Gly Gly Thr Val Val
                115                 120                 125

Ile Glu Ser Tyr Val Val Asp Ile Pro Ala Gly Asn Thr Lys Glu Glu
130                 135                 140

Thr Cys Val Phe Val Asp Thr Ile Val Arg Cys Asn Leu Gln Ser Leu
145                 150                 155                 160

Ala Gln Met Ala Glu Asn Met Gly Ser
                165

<210> SEQ ID NO 107
<211> LENGTH: 210
<212> TYPE: PRT
<213> ORGANISM: Glycine max

<400> SEQUENCE: 107

Met Thr Ile Leu Pro His Ser Asn Asn Lys Ser Ser Asn His Lys Phe
1               5                   10                  15

Ile Ala His Gln Asn Tyr Met Ala Ser Glu Thr His His Val Gln
            20                  25                  30

Gly Leu Thr Pro Glu Glu Leu Thr Lys Leu Glu Pro Ile Ile Lys Lys
        35                  40                  45

Tyr His Leu Phe Glu Gln Ser Pro Asn Thr Cys Phe Ser Ile Ile Thr
50                  55                  60

Tyr Arg Ile Glu Ala Pro Ala Lys Ala Val Trp Pro Phe Val Arg Ser
65                  70                  75                  80

Phe Asp Asn Pro Gln Lys Tyr Lys His Phe Ile Lys Gly Cys Asn Met
                85                  90                  95

Arg Gly Asp Gly Gly Val Gly Ser Ile Arg Glu Val Thr Val Val Ser
                100                 105                 110

Gly Leu Pro Ala Ser Thr Ser Thr Glu Arg Leu Glu Ile Leu Asp Asp
                115                 120                 125

Asp Lys His Val Leu Ser Phe Arg Val Val Gly Gly Glu His Arg Leu
130                 135                 140

Lys Asn Tyr Arg Ser Val Thr Ser Val Asn Glu Phe Asn Lys Glu Gly
145                 150                 155                 160

Lys Val Tyr Thr Ile Val Leu Glu Ser Tyr Ile Val Asp Ile Pro Glu
                165                 170                 175

Gly Asn Thr Glu Glu Asp Thr Lys Met Phe Val Asp Thr Val Val Lys
                180                 185                 190

Leu Asn Leu Gln Lys Leu Gly Val Val Ala Met Ala Ser Ser Met His
            195                 200                 205

Gly Gln

<210> SEQ ID NO 108
<211> LENGTH: 193
<212> TYPE: PRT
<213> ORGANISM: Glycine max

<400> SEQUENCE: 108

Met Asn Arg Ile Gly Asn Gly Gly Gly Gly Gly Gly Leu Ser Asn
1               5                   10                  15

Val Glu Met Glu Tyr Ile Arg Arg His His Arg His Glu Pro Gly Glu
            20                  25                  30

Asn Gln Cys Gly Ser Ala Leu Val Lys His Ile Arg Ala Pro Val Pro
        35                  40                  45

Gln Val Trp Ser Leu Val Arg Arg Phe Asp Gln Pro Gln Lys Tyr Lys
    50                  55                  60

Pro Phe Ile Ser Arg Cys Val Val Arg Gly Asn Leu Glu Ile Gly Ser
65                  70                  75                  80

Leu Arg Glu Val Asp Val Lys Ser Gly Leu Pro Ala Thr Thr Ser Thr
                85                  90                  95

Glu Arg Leu Glu Leu Leu Asp Asp Asn Glu His Ile Leu Ser Ile Arg
            100                 105                 110

Ile Ile Gly Gly Asp His Arg Leu Arg Asn Tyr Ser Ser Ile Met Ser
        115                 120                 125

Leu His Pro Glu Ile Ile Asp Gly Arg Pro Gly Thr Leu Val Ile Glu
    130                 135                 140

Ser Phe Val Val Asp Val Pro Glu Gly Asn Thr Lys Asp Glu Thr Cys
145                 150                 155                 160

Tyr Phe Val Glu Ala Leu Ile Lys Cys Asn Leu Lys Ser Leu Ala Asp
                165                 170                 175

Val Ser Glu Gly Leu Ala Val Gln Asp Cys Thr Glu Pro Ile Asp Arg
            180                 185                 190

Ile

<210> SEQ ID NO 109
<211> LENGTH: 188
<212> TYPE: PRT
<213> ORGANISM: Glycine max

<400> SEQUENCE: 109

Met Ala Ser Glu Thr His His His Val Gln Gly Leu Thr Pro Glu Glu
1               5                   10                  15

Leu Thr Gln Leu Glu Pro Ile Ile Lys Lys Tyr His Leu Phe Glu Ala
            20                  25                  30

Ser Ser Asn Lys Cys Phe Ser Ile Ile Thr His Arg Ile Glu Ala Pro
        35                  40                  45

Ala Ser Ser Val Trp Pro Leu Val Arg Asn Phe Asp Asn Pro Gln Lys
    50                  55                  60

Tyr Lys His Phe Ile Lys Gly Cys Asn Met Lys Gly Asp Gly Ser Val
65                  70                  75                  80

Gly Ser Ile Arg Glu Val Thr Val Val Ser Gly Leu Pro Ala Ser Thr
                85                  90                  95

Ser Thr Glu Arg Leu Glu Ile Leu Asp Asp Asp Lys His Val Leu Ser
            100                 105                 110

Phe Arg Val Val Gly Gly Glu His Arg Leu Gln Asn Tyr Arg Ser Val
        115                 120                 125

```
Thr Ser Val Asn Glu Phe His Lys Glu Gly Lys Val Tyr Thr Ile Val
        130                 135                 140

Leu Glu Ser Tyr Ile Val Asp Ile Pro Glu Gly Asn Thr Glu Glu Asp
145                 150                 155                 160

Thr Lys Met Phe Val Asp Thr Val Val Lys Leu Asn Leu Gln Lys Leu
                165                 170                 175

Gly Val Val Ala Met Ala Ser Ser Met Asn Gly Arg
            180                 185
```

<210> SEQ ID NO 110
<211> LENGTH: 177
<212> TYPE: PRT
<213> ORGANISM: Glycine max

<400> SEQUENCE: 110

```
Met Leu Pro Asn Asn Pro Ser Thr Ile Val Pro Asp Ala Val Ala Arg
1               5                   10                  15

His His Thr His Val Val Ser Pro Gln Gln Cys Cys Ser Ala Val Val
            20                  25                  30

Gln Glu Ile Ala Ala Pro Val Ser Thr Val Trp Ser Val Val Arg Arg
        35                  40                  45

Phe Asp Asn Pro Gln Ala Tyr Lys His Phe Val Lys Ser Cys His Val
    50                  55                  60

Ile Leu Gly Asp Gly Asp Val Gly Thr Leu Arg Glu Val His Val Ile
65                  70                  75                  80

Ser Gly Leu Pro Ala Ala Val Ser Thr Glu Arg Leu Asp Val Leu Asp
                85                  90                  95

Asp Glu Arg His Val Ile Gly Phe Ser Met Val Gly Gly Asp His Arg
            100                 105                 110

Leu Phe Asn Tyr Arg Ser Val Thr Thr Leu His Pro Arg Ser Ala Ala
        115                 120                 125

Gly Thr Val Val Val Glu Ser Tyr Val Val Asp Val Pro Pro Gly Asn
    130                 135                 140

Thr Thr Glu Asp Thr Arg Val Phe Val Asp Thr Ile Leu Arg Cys Asn
145                 150                 155                 160

Leu Gln Ser Leu Ala Lys Phe Ala Glu Asn Leu Thr Lys Leu His Gln
                165                 170                 175

Arg
```

<210> SEQ ID NO 111
<211> LENGTH: 185
<212> TYPE: PRT
<213> ORGANISM: Glycine max

<400> SEQUENCE: 111

```
Met Asn Gly Gly Glu Ser Tyr Gly Ala Ile Glu Thr Gln Tyr Ile Arg
1               5                   10                  15

Arg His His Lys His Glu Pro Arg Glu Asn Gln Cys Thr Ser Ala Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Met Gln Gly Asp Leu Gly Ile Gly Ser Val Arg Glu Val Asn Val Lys
65                  70                  75                  80
```

```
Ser Gly Leu Pro Ala Thr Thr Ser Thr Glu Arg Leu Glu Gln Leu Asp
                85                  90                  95

Asp Glu Glu His Ile Leu Gly Ile Arg Ile Val Gly Asp His Arg
            100                 105                 110

Leu Arg Asn Tyr Ser Ser Ile Ile Thr Val His Pro Glu Val Ile Asp
            115                 120                 125

Gly Arg Pro Gly Thr Met Val Ile Glu Ser Phe Val Asp Val Pro
            130                 135             140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
                165                 170                 175

Gln Gly Arg Thr Asn Pro Ile Asn His
            180                 185

<210> SEQ ID NO 112
<211> LENGTH: 191
<212> TYPE: PRT
<213> ORGANISM: Glycine max

<400> SEQUENCE: 112

Met Gly Ile Thr Ile Gly Ile Gln Cys Leu Glu Ile Glu Glu Ile Ser
1               5                   10                  15

Ile Cys Asp Gly Met Phe Cys Tyr Leu Val Asp Phe Val Asp Val Lys
            20                  25                  30

Glu Lys Met Asn Tyr Cys Leu Met Trp Phe Gly Tyr Phe Pro Ser Gln
            35                  40                  45

Val Trp Ser Leu Val Arg Arg Phe Asp Gln Pro Gln Lys Tyr Lys Pro
50                  55                  60

Phe Val Ser Arg Cys Ile Met Gln Gly Asp Leu Gly Ile Gly Ser Val
65                  70                  75                  80

Arg Glu Val Asn Val Lys Ser Gly Leu Pro Ala Thr Thr Ser Thr Glu
                85                  90                  95

Arg Leu Glu Gln Leu Asp Asp Glu Glu His Ile Leu Gly Ile Arg Ile
            100                 105                 110

Val Gly Gly Asp His Arg Leu Arg Asn Tyr Ser Ser Ile Ile Thr Val
            115                 120                 125

His Pro Glu Val Ile Asp Gly Arg Pro Ser Thr Met Val Ile Glu Ser
            130                 135                 140

Phe Val Val Asp Val Pro Asp Gly Asn Thr Arg Asp Glu Thr Cys Tyr
145                 150                 155                 160

Phe Val Glu Ala Leu Ile Arg Cys Asn Leu Ser Ser Leu Ala Asp Val
                165                 170                 175

Ser Glu Arg Met Ala Val Gln Gly Arg Thr Asp Pro Ile Asn His
            180                 185                 190

<210> SEQ ID NO 113
<211> LENGTH: 185
<212> TYPE: PRT
<213> ORGANISM: Artificial Sequence
<220> FEATURE:
<223> OTHER INFORMATION: synthetic PYR/PYL receptor protein

<400> SEQUENCE: 113

Met Asn Gly Gly Glu Ser Tyr Gly Ala Ile Glu Thr Gln Tyr Ile Arg
1               5                   10                  15

Arg His His Lys His Glu Pro Arg Glu Asn Gln Cys Thr Ser Ala Leu
```

```
                20                  25                  30
Val Lys His Ile Arg Ala Pro Val His Leu Val Trp Ser Leu Val Arg
                35                  40                  45
Arg Phe Asp Gln Pro Gln Lys Tyr Lys Pro Phe Val Ser Arg Cys Ile
        50                  55                  60
Met Gln Gly Asp Leu Gly Ile Gly Ser Val Arg Glu Val Asn Val Lys
65                  70                  75                  80
Ser Gly Leu Pro Ala Thr Thr Ser Thr Glu Arg Leu Glu Gln Leu Asp
                85                  90                  95
Asp Glu Glu His Ile Leu Gly Ile Arg Ile Val Gly Gly Asp His Arg
                100                 105                 110
Leu Arg Asn Tyr Ser Ser Ile Ile Thr Val His Pro Glu Val Ile Asp
                115                 120                 125
Gly Arg Pro Ser Thr Met Val Ile Glu Ser Phe Val Asp Val Pro
                130                 135                 140
Asp Gly Asn Thr Arg Asp Glu Thr Cys Tyr Phe Val Glu Ala Leu Ile
145                 150                 155                 160
Arg Cys Asn Leu Ser Ser Leu Ala Asp Val Ser Glu Arg Met Ala Val
                165                 170                 175
Gln Gly Arg Thr Asp Pro Ile Asn His
                180                 185
```

<210> SEQ ID NO 114
<211> LENGTH: 204
<212> TYPE: PRT
<213> ORGANISM: Sorghum bicolor

<400> SEQUENCE: 114

```
Met Glu Thr His Val Glu Arg Ala Leu Arg Ala Thr Leu Thr Glu Ala
1               5                   10                  15
Glu Val Arg Ala Leu Glu Pro Ala Val Arg Glu His His Thr Phe Pro
                20                  25                  30
Ala Gly Arg Val Ala Ala Gly Thr Thr Thr Pro Thr Pro Thr Thr Cys
                35                  40                  45
Thr Ser Leu Val Ala Gln Arg Val Ser Ala Pro Val Arg Ala Val Trp
        50                  55                  60
Pro Ile Val Arg Ser Phe Gly Asn Pro Gln Arg Tyr Lys His Phe Val
65                  70                  75                  80
Arg Thr Cys Ala Leu Ala Ala Gly Asp Gly Ala Ser Val Gly Ser Val
                85                  90                  95
Arg Glu Val Thr Val Val Ser Gly Leu Pro Ala Ser Ser Thr Glu
                100                 105                 110
Arg Leu Glu Val Leu Asp Asp Asp Arg His Ile Leu Ser Phe Arg Val
                115                 120                 125
Val Gly Gly Asp His Arg Leu Arg Asn Tyr Arg Ser Val Thr Ser Val
                130                 135                 140
Thr Glu Phe Gln Pro Gly Pro Tyr Cys Val Val Glu Ser Tyr Ala
145                 150                 155                 160
Val Asp Val Pro Glu Gly Asn Thr Ala Glu Asp Thr Arg Met Phe Thr
                165                 170                 175
Asp Thr Val Val Arg Leu Asn Leu Gln Lys Leu Ala Ala Val Ala Glu
                180                 185                 190
Glu Ser Ala Ala Ala Ala Ala Gly Asn Arg Arg
                195                 200
```

<210> SEQ ID NO 115
<211> LENGTH: 204
<212> TYPE: PRT
<213> ORGANISM: Sorghum bicolor

<400> SEQUENCE: 115

Met Glu Pro His Met Glu Thr Ala Leu Arg Gln Gly Gly Leu Ser Glu
1               5                   10                  15

Leu Glu Gln Arg Glu Leu Glu Pro Val Val Arg Ala His His Thr Phe
            20                  25                  30

Pro Gly Arg Ser Pro Gly Thr Thr Cys Thr Ser Leu Val Thr Gln Arg
        35                  40                  45

Val Asp Ala Pro Leu Ser Ala Val Trp Pro Ile Val Arg Gly Phe Ala
    50                  55                  60

Ala Pro Gln Arg Tyr Lys His Phe Ile Lys Ser Cys Asp Leu Arg Ser
65                  70                  75                  80

Gly Asp Gly Ala Thr Val Gly Ser Val Arg Glu Val Thr Val Val Ser
                85                  90                  95

Gly Leu Pro Ala Ser Thr Ser Thr Glu Arg Leu Glu Ile Leu Asp Asp
            100                 105                 110

Asp Arg His Ile Leu Ser Phe Arg Val Val Gly Gly Asp His Arg Leu
        115                 120                 125

Arg Asn Tyr Arg Ser Val Thr Ser Val Thr Glu Phe His His His
130                 135                 140

Gln Ala Ala Ala Gly Arg Pro Tyr Cys Val Val Val Glu Ser Tyr Val
145                 150                 155                 160

Val Asp Val Pro Glu Gly Asn Thr Glu Glu Asp Thr Arg Met Phe Thr
                165                 170                 175

Asp Thr Val Val Lys Leu Asn Leu Gln Lys Leu Ala Ala Ile Ala Thr
            180                 185                 190

Ser Ser Ala Ala Ala Ala Ser Asn Ser Ser Thr
        195                 200

<210> SEQ ID NO 116
<211> LENGTH: 258
<212> TYPE: PRT
<213> ORGANISM: Sorghum bicolor

<400> SEQUENCE: 116

Met Val Glu Ser Pro Asn Pro Asn Ser Pro Ser Arg Pro Leu Cys Ile
1               5                   10                  15

Lys Tyr Thr Arg Ala Pro Ala Arg His Phe Ser Pro Pro Leu Pro Phe
            20                  25                  30

Ser Ser Leu Ile Ile Ser Ala Asn Pro Ile Glu Pro Lys Ala Met Asp
        35                  40                  45

Lys Gln Gly Ala Gly Gly Asp Val Glu Val Pro Ala Gly Leu Gly Leu
    50                  55                  60

Thr Ala Ala Glu Tyr Glu Gln Leu Arg Ser Thr Val Asp Ala His His
65                  70                  75                  80

Arg Tyr Ala Val Gly Glu Gly Gln Cys Ser Ser Leu Leu Ala Gln Arg
                85                  90                  95

Ile Gln Ala Pro Pro Ala Ala Val Trp Ala Ile Val Arg Arg Phe Asp
            100                 105                 110

Cys Pro Gln Val Tyr Lys His Phe Ile Arg Ser Cys Ala Leu Arg Pro
        115                 120                 125

```
Asp Pro Glu Ala Gly Asp Ala Leu Arg Pro Gly Arg Leu Arg Glu Val
    130                 135                 140

Ser Val Ile Ser Gly Leu Pro Ala Ser Thr Thr Glu Arg Leu Asp
145                 150                 155                 160

Leu Leu Asp Asp Ala Ala Arg Val Phe Gly Phe Ser Ile Thr Gly Gly
                165                 170                 175

Glu His Arg Leu Arg Asn Tyr Arg Ser Val Thr Thr Val Ser Glu Leu
            180                 185                 190

Ala Asp Pro Gly Ile Cys Thr Val Val Leu Ser Tyr Val Val Asp
            195                 200                 205

Val Pro Asp Gly Asn Thr Glu Asp Asp Thr Arg Leu Phe Ala Asp Thr
210                 215                 220

Val Ile Arg Leu Asn Leu Gln Lys Leu Lys Ser Val Ala Glu Ala Asn
225                 230                 235                 240

Ala Ala Ala Ala Ala Ser Phe Val Ser Val Pro Pro Glu Pro
                245                 250                 255

Glu Glu

<210> SEQ ID NO 117
<211> LENGTH: 222
<212> TYPE: PRT
<213> ORGANISM: Sorghum bicolor

<400> SEQUENCE: 117

Met Pro Cys Leu Gln Ala Ser Ser Pro Gly Ser Met Pro His Gln
1               5                   10                  15

His His Gly Arg Val Leu Ala Gly Val Gly Cys Ala Ala Glu Val Ala
            20                  25                  30

Ala Ala Ala Val Ala Ala Thr Ser Pro Ala Ala Gly Met Arg Cys Gly
            35                  40                  45

Ala His Asp Gly Glu Val Pro Ala Glu Ala Ala Arg His His Glu His
        50                  55                  60

Ala Ala Pro Gly Pro Gly Arg Cys Cys Ser Ala Val Val Gln His Val
65                  70                  75                  80

Ala Ala Pro Ala Ser Ala Val Trp Ser Val Val Arg Arg Phe Asp Gln
                85                  90                  95

Pro Gln Ala Tyr Lys Arg Phe Val Arg Ser Cys Ala Leu Leu Ala Gly
            100                 105                 110

Asp Gly Gly Val Gly Thr Leu Arg Glu Val Arg Val Ser Gly Leu
            115                 120                 125

Pro Ala Ala Ser Ser Arg Glu Arg Leu Glu Val Leu Asp Asp Glu Ser
        130                 135                 140

His Val Leu Ser Phe Arg Val Val Gly Gly Glu His Arg Leu Gln Asn
145                 150                 155                 160

Tyr Leu Ser Val Thr Thr Val His Pro Ser Pro Ala Ala Pro Asp Ala
                165                 170                 175

Ala Thr Val Val Val Glu Ser Tyr Val Val Asp Val Pro Pro Gly Asn
            180                 185                 190

Thr Pro Glu Asp Thr Arg Val Phe Val Asp Thr Ile Val Lys Cys Asn
        195                 200                 205

Leu Gln Ser Leu Ala Thr Thr Ala Glu Lys Leu Ala Ala Val
    210                 215                 220

<210> SEQ ID NO 118
<211> LENGTH: 211
```

<212> TYPE: PRT
<213> ORGANISM: Sorghum bicolor

<400> SEQUENCE: 118

Met Val Glu Met Asp Gly Gly Val Gly Val Gly Gly Gly Gln Gln
1               5                   10                  15

Thr Pro Ala Pro Arg Arg Trp Arg Leu Ala Asp Glu Leu Arg Cys Asp
            20                  25                  30

Leu Arg Ala Met Glu Thr Asp Tyr Val Arg Arg Phe His Arg His Glu
        35                  40                  45

Pro Arg Asp His Gln Cys Ser Ser Ala Val Ala Lys His Ile Lys Ala
    50                  55                  60

Pro Val His Leu Val Trp Ser Leu Val Arg Arg Phe Asp Gln Pro Gln
65                  70                  75                  80

Leu Phe Lys Pro Phe Val Ser Arg Cys Glu Met Lys Gly Asn Ile Glu
                85                  90                  95

Ile Gly Ser Val Arg Glu Val Asn Val Lys Ser Gly Leu Pro Ala Thr
            100                 105                 110

Arg Ser Thr Glu Arg Leu Glu Leu Leu Asp Asp Asn Glu His Ile Leu
        115                 120                 125

Ser Val Lys Phe Val Gly Gly Asp His Arg Leu Gln Asn Tyr Ser Ser
    130                 135                 140

Ile Leu Thr Val His Pro Glu Val Ile Asp Gly Arg Pro Gly Thr Leu
145                 150                 155                 160

Val Ile Glu Ser Phe Val Val Asp Val Pro Asp Gly Asn Thr Lys Asp
                165                 170                 175

Glu Thr Cys Tyr Phe Val Glu Ala Leu Leu Lys Cys Asn Leu Lys Ser
            180                 185                 190

Leu Ala Glu Val Ser Glu Arg Gln Val Ile Lys Asp Gln Thr Glu Pro
        195                 200                 205

Leu Asp Arg
    210

<210> SEQ ID NO 119
<211> LENGTH: 216
<212> TYPE: PRT
<213> ORGANISM: Sorghum bicolor

<400> SEQUENCE: 119

Met Pro Tyr Thr Ala Pro Arg Pro Ser Pro Gln Gln His Ser Arg Val
1               5                   10                  15

Thr Gly Gly Gly Ala Lys Ala Ala Ile Val Ala Ala Ser His Gly Ala
            20                  25                  30

Ser Cys Ala Ala Val Pro Ala Glu Val Ala Arg His His Glu His Ala
        35                  40                  45

Ala Arg Ala Gly Gln Cys Cys Ser Ala Val Val Gln Ala Ile Ala Ala
    50                  55                  60

Pro Val Gly Ala Val Trp Ser Val Val Arg Arg Phe Asp Arg Pro Gln
65                  70                  75                  80

Ala Tyr Lys His Phe Ile Arg Ser Cys Arg Leu Val Asp Asp Gly Gly
                85                  90                  95

Gly Gly Ala Gly Ala Gly Ala Gly Ala Thr Val Ala Val Gly Ser Val
            100                 105                 110

Arg Glu Val Arg Val Val Ser Gly Leu Pro Ala Thr Ser Ser Arg Glu
        115                 120                 125

-continued

```
Arg Leu Glu Ile Leu Asp Asp Glu Arg Arg Val Leu Ser Phe Arg Val
    130             135                 140

Val Gly Gly Glu His Arg Leu Ala Asn Tyr Arg Ser Val Thr Thr Val
145             150                 155                 160

His Glu Ala Glu Ala Gly Ala Gly Gly Thr Val Val Val Glu Ser Tyr
            165             170                 175

Val Val Asp Val Pro Pro Gly Asn Thr Ala Asp Glu Thr Arg Val Phe
        180             185                 190

Val Asp Thr Ile Val Arg Cys Asn Leu Gln Ser Leu Ala Arg Thr Ala
        195             200                 205

Glu Arg Leu Ala Leu Ala Leu Ala
    210             215
```